US007811973B2

(12) United States Patent
Burioni et al.

(10) Patent No.: US 7,811,973 B2
(45) Date of Patent: Oct. 12, 2010

(54) PHAGE DISPLAY TECHNOLOGIES

(75) Inventors: Roberto Burioni, Rimini (IT); Massimo Clementi, Iesi (IT)

(73) Assignee: Ribovax Biotechnologies SA, Petit-Lancy (CH)

( * ) Notice: Subject to any disclaimer, the term of this patent is extended or adjusted under 35 U.S.C. 154(b) by 0 days.

(21) Appl. No.: 11/994,820

(22) PCT Filed: Jul. 6, 2006

(86) PCT No.: PCT/IB2006/001878

§ 371 (c)(1), (2), (4) Date: Jul. 11, 2008

(87) PCT Pub. No.: WO2007/007154

PCT Pub. Date: Jan. 18, 2007

(65) Prior Publication Data

US 2008/0312101 A1    Dec. 18, 2008

(30) Foreign Application Priority Data

Jul. 7, 2005    (WO) ................ PCT/EP2005/007325

(51) Int. Cl.
*C40B 40/02*    (2006.01)
*C40B 50/06*    (2006.01)
*C12N 15/87*    (2006.01)
*A61K 39/00*    (2006.01)

(52) U.S. Cl. ..................... 506/14; 435/320.1; 506/26

(58) Field of Classification Search .................. None
See application file for complete search history.

(56) References Cited

U.S. PATENT DOCUMENTS

2005/0112550 A1*    5/2005    Gershoni et al. ............... 435/5

OTHER PUBLICATIONS

Wang (Dec. 18, 1997 Molecular Immunology vol. 34 p. 609).*
Solomon (May 21, 2004 Protein Expression and Purification vol. 36 p. 226).*
Ryu (Mar. 2004 Plant Molecular Biology vol. 54 p. 489).*
Liang (Nov. 16, 2001 The Journal of Biological Chemistry vol. 277 p. 3593).*
Databadse WPI week 2000367, Derwent Publications Ltd., London, GB, AN 2003-712730, XP002413848 & WO 03/072773 A1 (American Biosciences KK), Sep. 4, 2003.
Den W. et al, "A bidirectional phage display vector for the selection and mass transfer of polyclonal antibody libraries" Journal of Immunological Methods, Elsevier Science Publishers B.V., Amsterdam, NL, vol. 222, No. 1-2, Jan. 1999, pp. 45-57, XP004152426.

* cited by examiner

*Primary Examiner*—Jeffrey S Lundgren
*Assistant Examiner*—Christian Boesen
(74) *Attorney, Agent, or Firm*—Arent Fox LLP

(57)    ABSTRACT

The present invention provides novel technologies for producing and screening fusion proteins on the surface of filamentous phage. In particular, a single vector can be used for generating cell and phage libraries containing a given series of protein sequences fused to either one or other of two phage coat proteins. This approach simplifies and improves the efficiency of the subsequent phage display-based selection of protein-binding molecules having therapeutic or diagnostic utility, such as antibodies, peptides, or epitope-binding regions.

14 Claims, 23 Drawing Sheets

Figure 1

|  |  | SpeI |  | SfiI |  |  |  |  |  |  |  |  |  |  |
|---|---|---|---|---|---|---|---|---|---|---|---|---|---|---|
|  |  | act | agt | ggc | cag | gcc | ggc | cag | ggt | ggc | ggt | ggc | tct | cca | ttc | 42 |
|  |  | T | S | G | Q | A | G | Q | G | G | G | G | S | P | F | 14 |

DIS Linker2

| gtt | tgt | gaa | tat | caa | ggc | caa | tcg | tct | gac | ctg | cct | caa | cct | 84 |
|---|---|---|---|---|---|---|---|---|---|---|---|---|---|---|
| V | C | E | Y | Q | G | Q | S | S | D | L | P | Q | P | 28 |

| cct | gtc | aat | gct | ggc | ggc | ggc | tct | ggt | ggt | ggt | tct | ggt | ggc | 126 |
|---|---|---|---|---|---|---|---|---|---|---|---|---|---|---|
| P | V | N | A | G | G | G | S | G | G | G | S | G | G | 42 |

| ggc | tct | gag | ggt | ggt | ggc | tct | gag | ggt | ggc | ggt | tct | gag | ggt | 168 |
|---|---|---|---|---|---|---|---|---|---|---|---|---|---|---|
| G | S | E | G | G | G | S | E | G | G | G | S | E | G | 56 |

| ggc | ggc | tct | gag | gga | ggc | ggt | tcc | ggt | ggt | ggc | tct | ggt | tct | 210 |
|---|---|---|---|---|---|---|---|---|---|---|---|---|---|---|
| G | G | S | E | G | G | G | S | G | G | G | S | G | S | 70 |

| ggt | gat | ttt | gat | tat | gaa | aag | atg | gca | aac | gct | aat | aag | ggg | 252 |
|---|---|---|---|---|---|---|---|---|---|---|---|---|---|---|
| G | D | F | D | Y | E | K | M | A | N | A | N | K | G | 84 |

| gct | atg | acc | gaa | aat | gcc | gat | gaa | aac | gcg | cta | cag | tct | gac | 294 |
|---|---|---|---|---|---|---|---|---|---|---|---|---|---|---|
| A | M | T | E | N | A | D | E | N | A | L | Q | S | D | 98 |

| gct | aaa | ggc | aaa | ctt | gat | tct | gtc | gct | act | gat | tac | ggt | gct | 336 |
|---|---|---|---|---|---|---|---|---|---|---|---|---|---|---|
| A | K | G | K | L | D | S | V | A | T | D | Y | G | A | 112 |

| gct | atc | gat | ggt | ttc | att | ggt | gac | gtt | tcc | ggc | ctt | gct | aat | 378 |
|---|---|---|---|---|---|---|---|---|---|---|---|---|---|---|
| A | I | D | G | F | I | G | D | V | S | G | L | A | N | 126 |

| ggt | aat | ggt | gct | act | ggt | gat | ttt | gct | ggc | tct | aat | tcc | caa | 420 |
|---|---|---|---|---|---|---|---|---|---|---|---|---|---|---|
| G | N | G | A | T | G | D | F | A | G | S | N | S | Q | 140 |

| atg | gct | caa | gtc | ggt | gac | ggt | gat | aat | tca | cct | tta | atg | aat | 462 |
|---|---|---|---|---|---|---|---|---|---|---|---|---|---|---|
| M | A | Q | V | G | D | G | D | N | S | P | L | M | N | 154 |

| aat | ttc | cgt | caa | tat | tta | cct | tcc | ctc | cct | caa | tcg | gtt | gaa | 504 |
|---|---|---|---|---|---|---|---|---|---|---|---|---|---|---|
| N | F | R | Q | Y | L | P | S | L | P | Q | S | V | E | 168 |

| tgt | cgc | cct | ttt | gtc | ttt | ggc | gct | ggt | aaa | cca | tat | gaa | ttt | 546 |
|---|---|---|---|---|---|---|---|---|---|---|---|---|---|---|
| C | R | P | F | V | F | G | A | G | K | P | Y | E | F | 182 |

| tct | att | gat | tgt | gac | aaa | ata | aac | tta | ttc | cgt | ggt | gtc | ttt | 588 |
|---|---|---|---|---|---|---|---|---|---|---|---|---|---|---|
| S | I | D | C | D | K | I | N | L | F | R | G | V | F | 196 |

| gcg | ttt | ctt | tta | tat | gtt | gcc | acc | ttt | atg | tat | gta | ttt | tct | 210 |
|---|---|---|---|---|---|---|---|---|---|---|---|---|---|---|
| A | F | L | L | Y | V | A | T | F | M | Y | V | F | S | 630 |

|  |  |  |  |  |  |  |  |  |  |  | NheI |  |  |
|---|---|---|---|---|---|---|---|---|---|---|---|---|---|
| acg | ttt | gct | aac | ata | ctg | cgt | aat | aag | gag | tct | taa | gctagc | 672 |
| T | F | A | N | I | L | R | N | K | E | S |  |  | 221 |

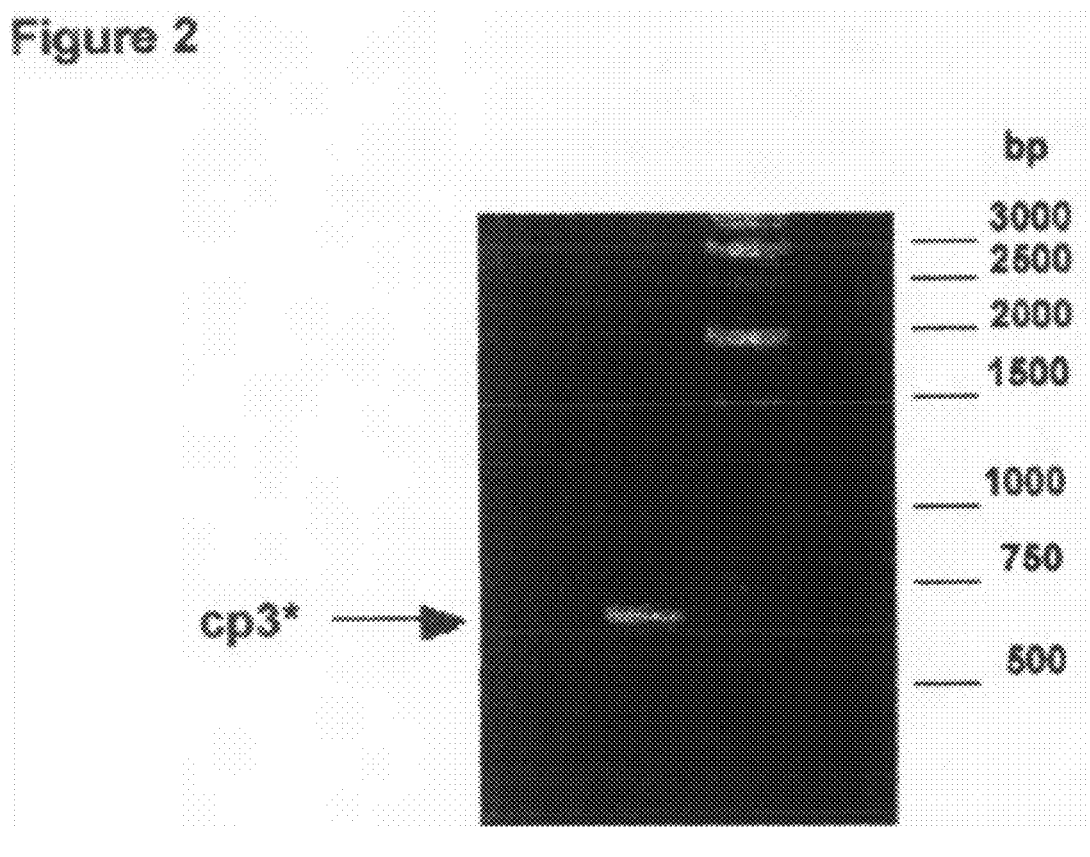

```
    XhoI                              SpeI
5'  TCGAGTATCCATATGATGTTCCAGATTATGCTA  3'
    3' CATAGGTATACTACAAGGTCTAATACGATGATC  5'
```

B)

```
<---------------------------PelB--------------------------
atg aaa tac cta ttg cct acg gca gcc gct gga ttg tta tta ctc   45
 M   K   Y   L   L   P   T   A   A   A   G   L   L   L   L   15
------------PelB-------------------------------------->  <-HA tag
gct gcc caa cca gcc atg gcc cag gtg aaa ctg ctc gag tat cca   90
 A   A   Q   P   A   M   A   Q   V   K   L   L   E   Y   P   30
-----HA tag---------------->  <-----------DIS linker2------
tat gat gtt cca gat tat gct act agt ggc cag gcc ggc cag ggt  135
 Y   D   V   P   D   Y   A   T   S   G   Q   A   G   Q   G   45
--DIS linker2->
ggc ggt ggc tct cca ttc gtt tgt gaa tat caa ggc caa tcg tct  180
 G   G   G   S   P   F   V   C   E   Y   Q   G   Q   S   S   60
gac ctg cct caa cct cct gtc aat gct ggc ggc ggc tct ggt ggt  225
 D   L   P   Q   P   P   V   N   A   G   G   G   S   G   G   75
ggt tct ggt ggc ggc tct gag ggt ggt ggc tct gag ggt ggc ggt  270
 G   S   G   G   G   S   E   G   G   G   S   E   G   G   G   90
tct gag ggt ggc ggc tct gag gga ggc ggt tcc ggt ggt ggc tct  315
 S   E   G   G   G   S   E   G   G   G   S   G   G   G   S  105
ggt tcc ggt gat ttt gat tat gaa aag atg gca aac gct aat aag  360
 G   S   G   D   F   D   Y   E   K   M   A   N   A   N   K  120
ggg gct atg acc gaa aat gcc gat gaa aac gcg cta cag tct gac  405
 G   A   M   T   E   N   A   D   E   N   A   L   Q   S   D  135
gct aaa ggc aaa ctt gat tct gtc gct act gat tac ggt gct gct  450
 A   K   G   K   L   D   S   V   A   T   D   Y   G   A   A  150
atc gat ggt ttc att ggt gac gtt tcc ggc ctt gct aat ggt aat  495
 I   D   G   F   I   G   D   V   S   G   L   A   N   G   N  165
ggt gct act ggt gat ttt gct ggc tct aat tcc caa atg gct caa  540
 G   A   T   G   D   F   A   G   S   N   S   Q   M   A   Q  180
gtc ggt gac ggt gat aat tca cct tta atg aat aat ttc cgt caa  585
 V   G   D   G   D   N   S   P   L   M   N   N   F   R   Q  195
tat tta cct tcc ctc cct caa tcg gtt gaa tgt cgc cct ttt gtc  630
 Y   L   P   S   L   P   Q   S   V   E   C   R   P   F   V  210
ttt ggc gct ggt aaa cca tat gaa ttt tct att gat tgt gac aaa  675
 F   S   A   G   K   P   Y   E   F   S   I   D   C   D   K  225
ata aac tta ttc cgt ggt gtc ttt gcg ttt ctt tta tat gtt gcc  720
 I   N   L   F   R   G   V   F   A   F   L   L   Y   V   A  240
acc ttt atg tat gta ttt tct acg ttt gct aac ata ctg cgt aat  765
 T   F   M   Y   V   F   S   T   F   A   N   I   L   R   N  255
aag gag tct                                                  774
 K   E   S                                                   258
```

Figure 4
A)
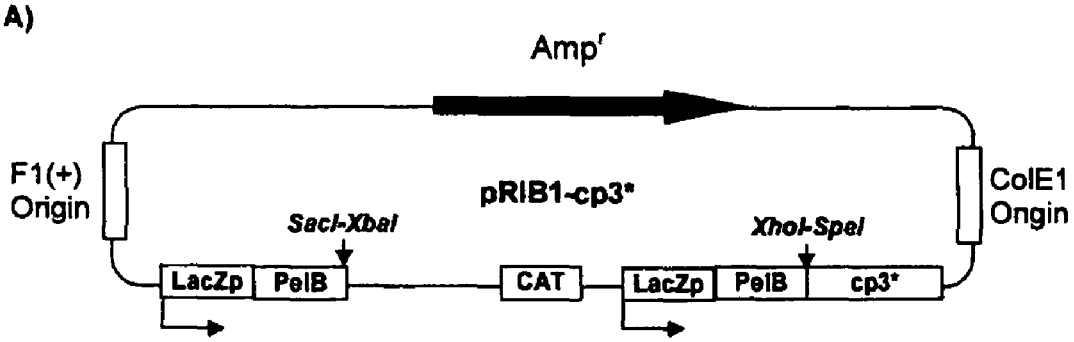
B)
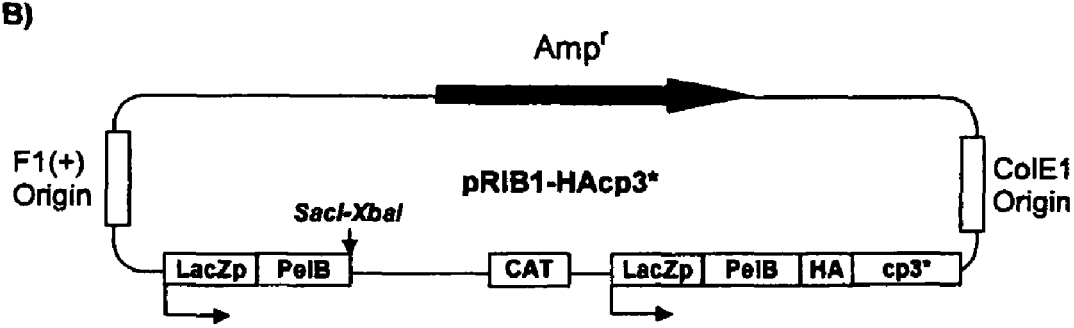
C)
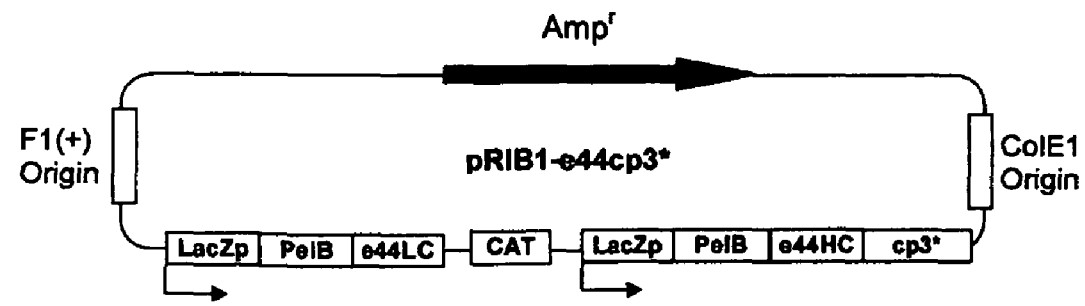

Figure 5
A)
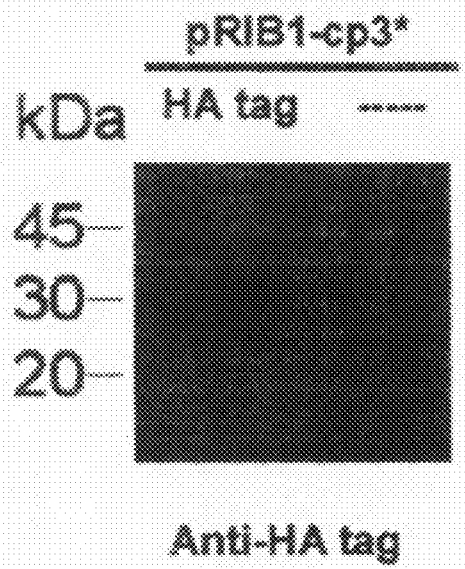
B)
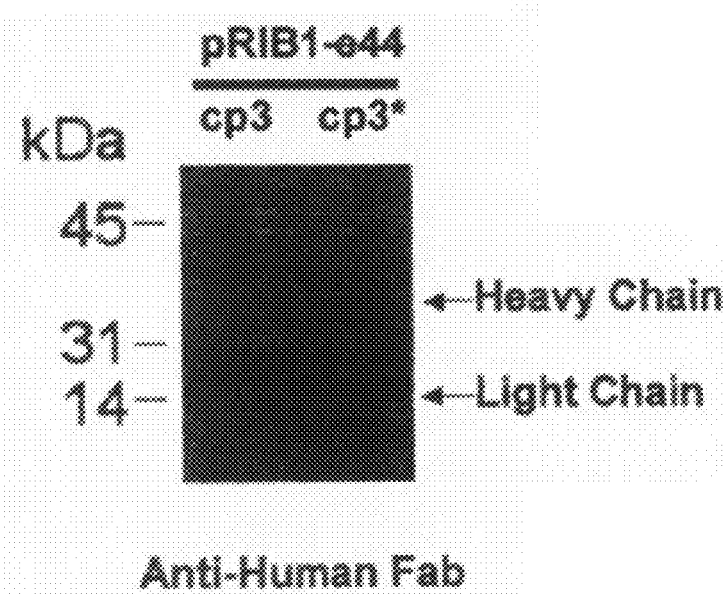

A)

```
    SpeI           SfiI
   act agt ggc cag gcc ggc cag ggt ggc ggt ggc tct    36
    T   S   G   Q   A   G   Q   G   G   G   G   S    12
                          DI8 Linker2 gct gag ggt gac gat ccc gca aaa gcg gcc ttt aac    72
    A   E   G   D   D   P   A   K   A   A   F   N    24 tcc ctg caa gcc tca gcg acc gaa tat atc ggt tat   108
    S   L   Q   A   S   A   T   E   Y   I   G   Y    36 gcg tgg gcg atg gtt gtt gtc att gtc ggc gca act   144
    A   W   A   M   V   V   V   I   V   G   A   T    48 atc ggt atc aag ctg ttt aag aaa ttc acc tcg aaa   180
    I   G   I   K   L   F   K   K   F   T   S   K    60

NheI
   gca agc tga gctagc                                 195
    A   S                                              62
```

```
<------------------------PelB------------------------
atg aaa tac cta ttg cct acg gca gcc gct gga ttg tta tta ctc   45
 M   K   Y   L   L   P   T   A   A   A   G   L   L   L   L    15

-----------PelB------------------------------------> <-HA tag
gct gcc caa cca gcc atg gcc cag gtg aaa ctg ctc gag tat cca   90
 A   A   Q   P   A   M   A   Q   V   K   L   L   E   Y   P    30

-----HA tag---------------> <-----------DIS linker2-------
tat gat gtt cca gat tat gct act agt ggc cag gcc ggc cag ggt  135
 Y   D   V   P   D   Y   A   T   S   G   Q   A   G   Q   G    45

--DIS linker2->
ggc ggt ggc tct gct gag ggt gac gat ccc gca aaa gcg gcc ttt  180
 G   G   G   S   A   E   G   D   D   P   A   K   A   A   F    60 aac tcc ctg caa gcc tca gcg acc gaa tat atc ggt tat gcg tgg  225
 N   S   L   Q   A   S   A   T   E   Y   I   G   Y   A   W    75 gcg atg gtt gtt gtc att gtc ggc gca act atc ggt atc aag ctg  270
 A   M   V   V   V   I   V   G   A   T   I   G   I   K   L    90 ttt aag aaa ttc acc tcg aaa gca agc                          297
 F   K   K   F   T   S   K   A   S                            99
```

Figure 8
A)
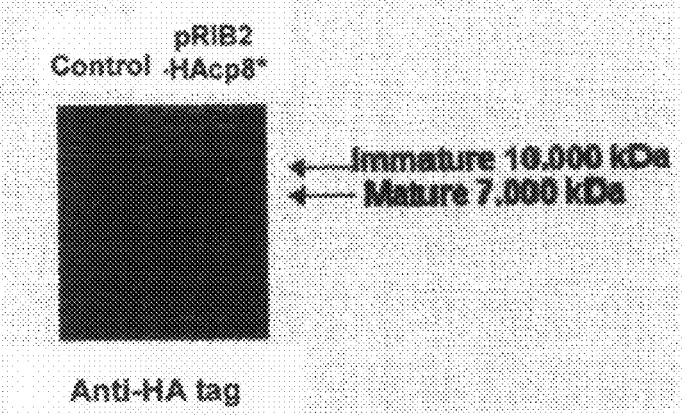
B)
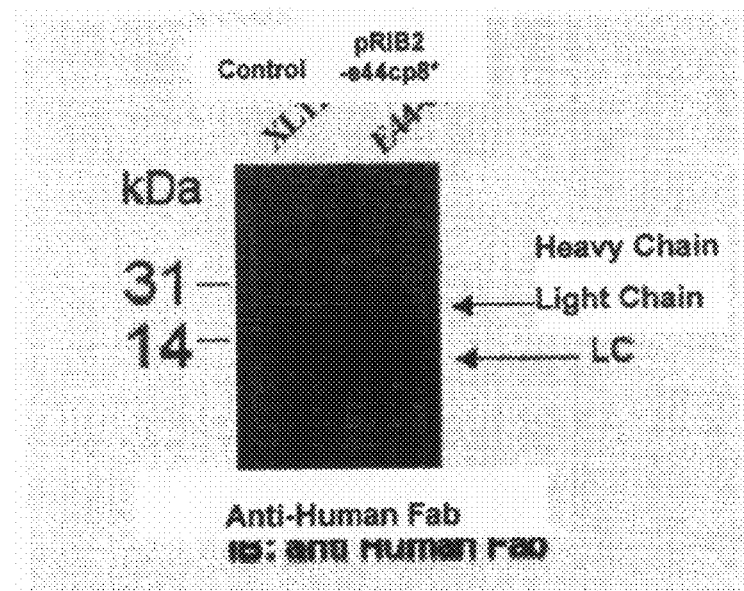

Figure 9
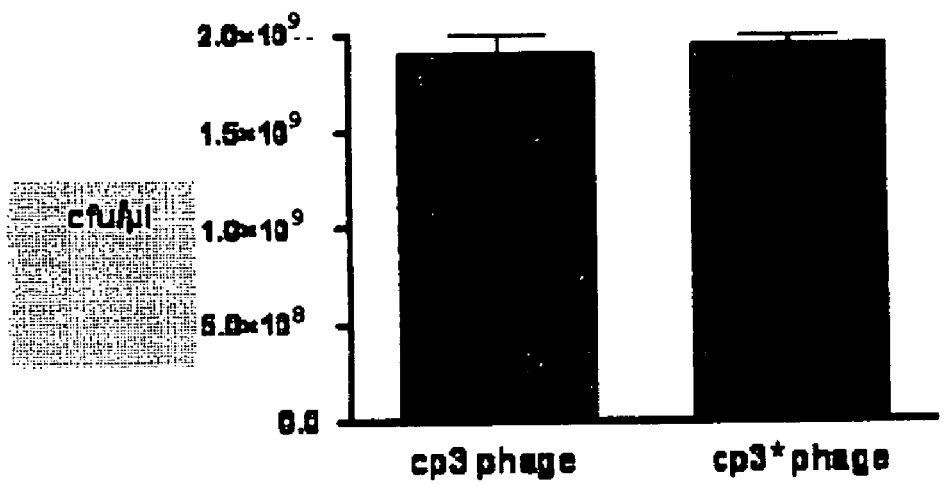
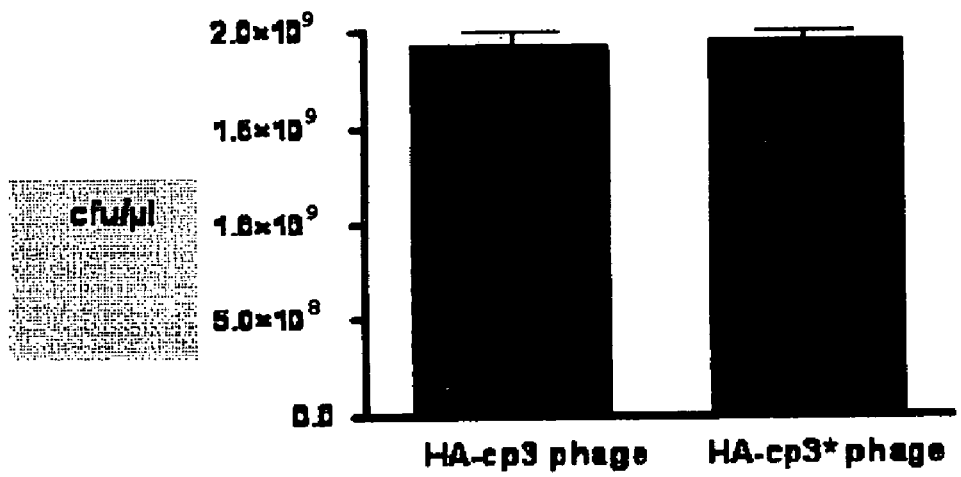
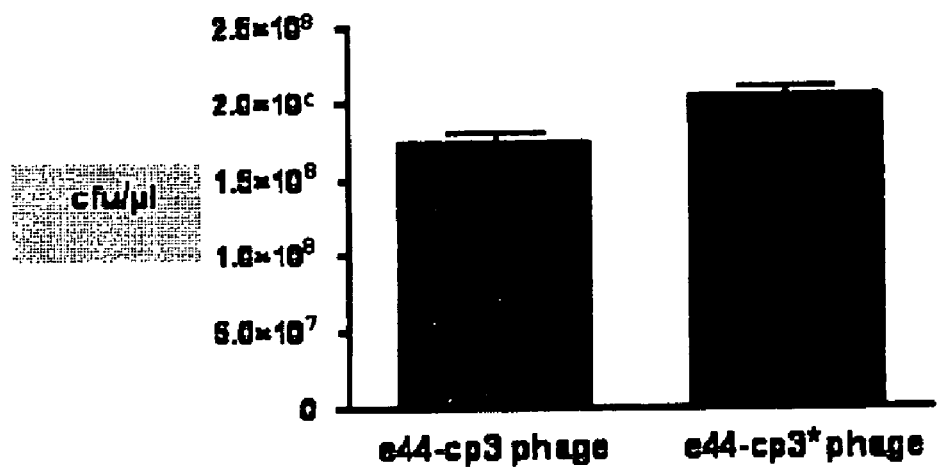

Figure 10
A)
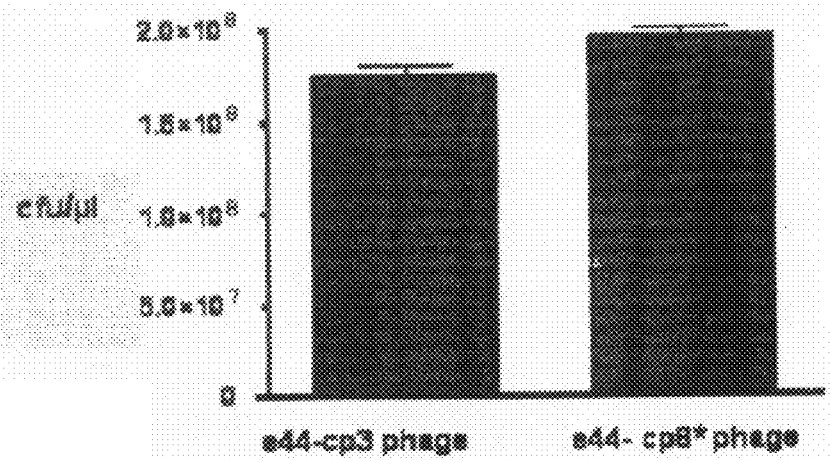
B)
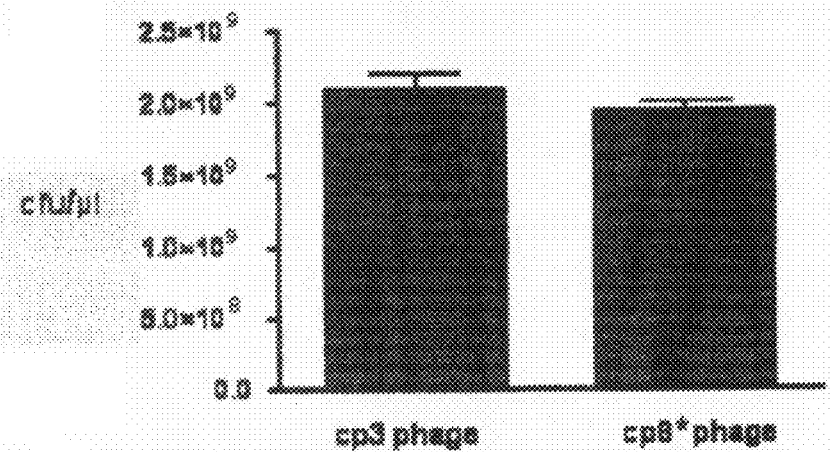
C)
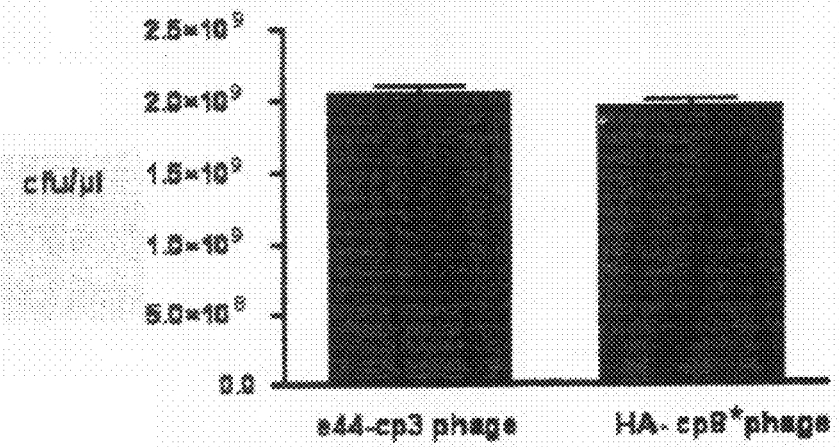

Figure 11
A)
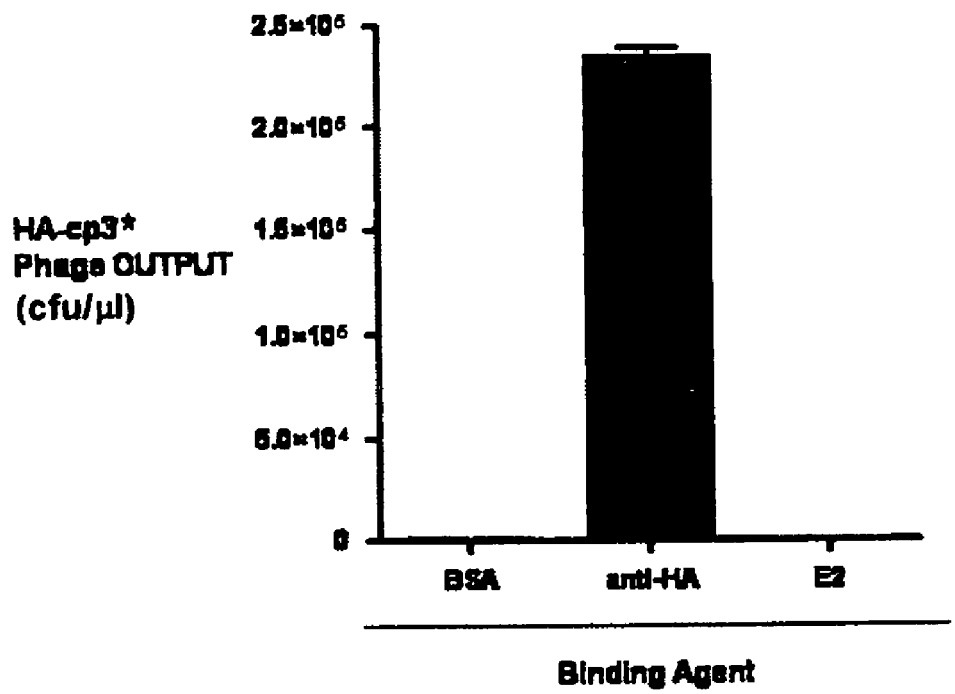
B)
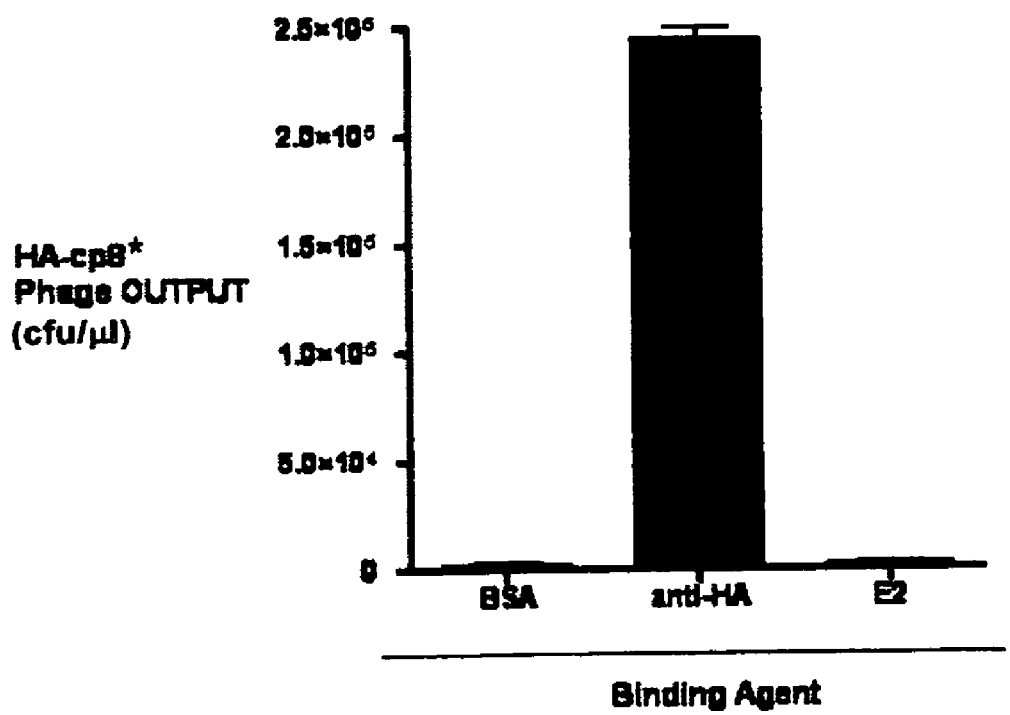

Figure 12
A)
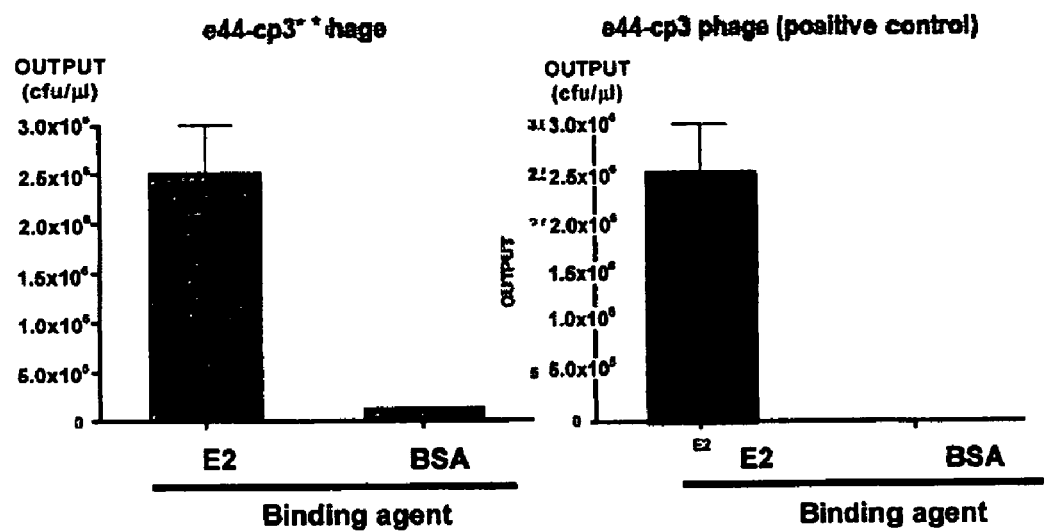
B)
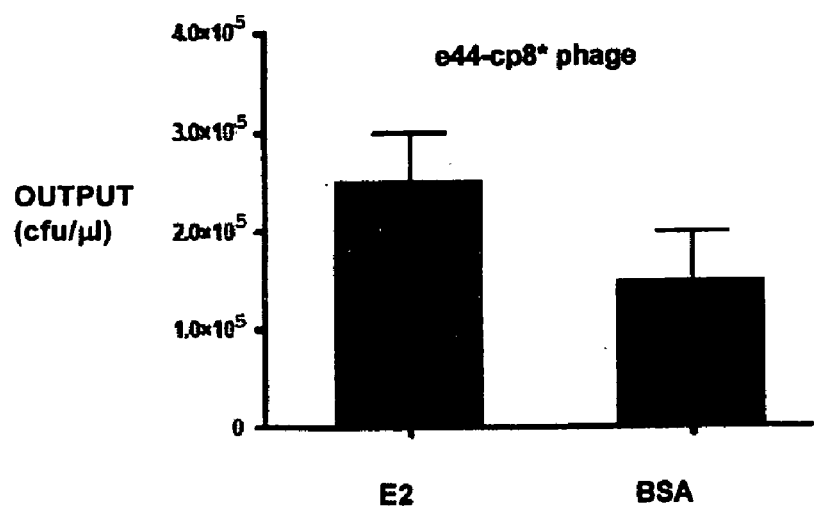

Figure 14
A)
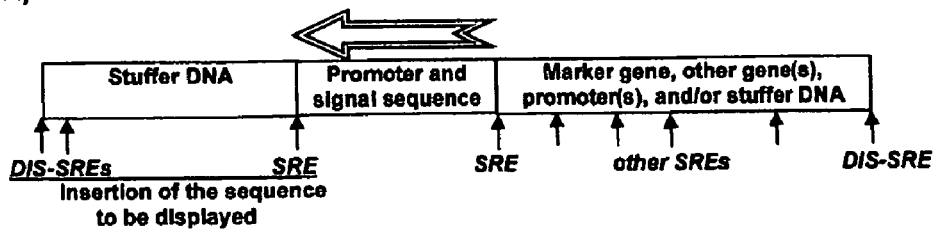
B)
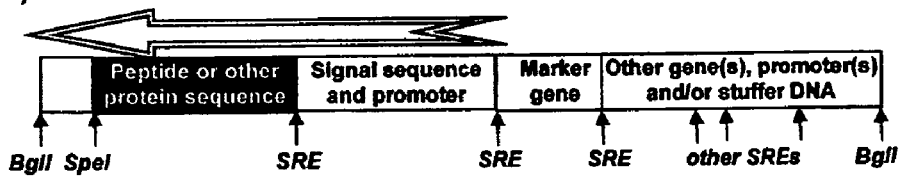
C)
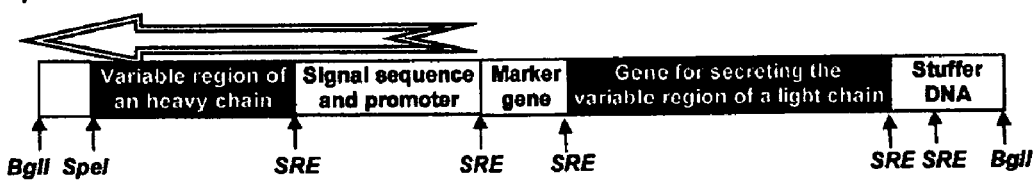
D)
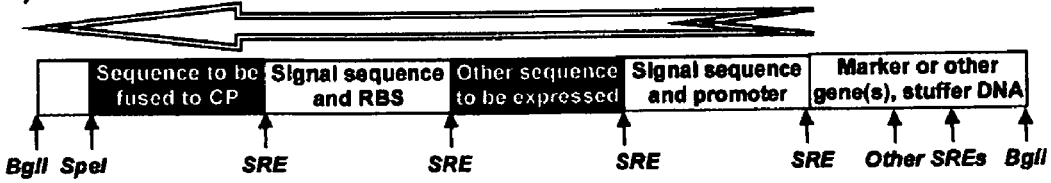

Figure 16

```
  1 TTAAGACTCC TTATTACGCA GTATGTTAGC AAACGTAGAA AATACATACA TAAAGGTGGC
    AATTCTGAGG AATAATGCGT CATACAATCG TTTGCATCTT TTATGTATGT ATTTCCACCG
    stop  S  E    K  N  R    L  I  N  A    F  T  S    F  V  Y    M  F  T  A 61 AACATATAAA AGAAACGCAA AGACACCACG GAATAAGTTT ATTTTGTCAC AATCAATAGA
    TTGTATATTT TCTTTGCGTT TCTGTGGTGC CTTATTCAAA TAAAACAGTG TTAGTTATCT
     V  Y  L    L  F  A    F  V  G  R    F  L  N    I  K  D    C  D  I  S 121 AAATTCATAT GGTTTACCAG CGCTAAAGAC AAAAGGGCGA CATTCAACCG ATTGAGGGAG
    TTTAAGTATA CCAAATGGTC GCGATTTCTG TTTTCCCGCT GTAAGTTGGC TAACTCCCTC
     F  E  Y    P  K  G    A  S  F  V    F  P  R    C  E  V    S  Q  P  L 181 GGAAGGTAAA TATTGACGGA AATTATTCAT TAAAGGTGAA TTATCACCGT CACCGACTTG
    CCTTCCATTT ATAACTGCCT TTAATAAGTA ATTTCCACTT AATAGTGGCA GTGGCTGAAC
     S  P  L    Y  Q  R    F  N  M    L  P  S    N  D  G    D  G  V  Q 241 AGCCATTTGG GAATTAGAGC CAGCAAAATC ACCAGTAGCA CCATTACCAT TAGCAAGGCC
    TCGGTAAACC CTTAATCTCG GTCGTTTTAG TGGTCATCGT GGTAATGGTA ATCGTTCCGG
     A  M  Q    S  N  S    G  A  F  D    G  T  A    G  N  G    N  A  L  G 301 GGAAACGTCA CCAATGAAAC CATCGATAGC AGCACCGTAA TCAGTAGCGA CAGAATCAAG
    CCTTTGCAGT GGTTACTTTG GTAGCTATCG TCGTGGCATT AGTCATCGCT GTCTTAGTTC
     S  V  D    G  I  F    G  D  I  A    G  Y    D  T  A    V  S  D  L 361 TTTGCCTTTA GCGTCAGACT GTAGCGCGTT TTCATCGGCA TTTTCGGTCA TAGCCCCCTT
    AAACGGAAAT CGCAGTCTGA CATCGCGCAA AAGTAGCCGT AAAAGCCAGT ATCGGGGGAA
     K  G  K    A  D  S    Q  L  A  N    E  D  A    N  E  T    M  A  G  K 421 ATTAGCGTTT GCCATCTTTT CATAATCAAA ATCACCGGAA CCAGAGCCAC CACCGGAACC
    TAATCGCAAA CGGTAGAAAA GTATTAGTTT TAGTGGCCTT GGTCTCGGTG GTGGCCTTGG
     N  A  N    A  M  K    E  Y  D  F    D  G  S    G  S  G    G  G  S  G 481 GCCTCCCTCA GAGCCGCCAC CCTCAGAACC GCCACCCTCA GAGCCACCAC CCTCAGAGCC
    CGGAGGGAGT CTCGGCGGTG GGAGTCTTGG CGGTGGGAGT CTCGGTGGTG GGAGTCTCGG
     G  G  E    S  G  G    G  E  S  G    G  G  E    S  G  G    G  E  S  G 541 GCCACCAGAA CCACCACCAG AGCCGCCGCC AGCATTGACA GGAGGTTGAG GCAGGTCAGA
    CGGTGGTCTT GGTGGTGGTC TCGGCGGCGG TCGTAACTGT CCTCCAACTC CGTCCAGTCT
     G  G  S    G  G  G    S  G  G    A  N  V    P  P  Q    P  L  D  S
                                                         DD-DIS linker2
601 CGATTGGCCT TGATATTCAC AAACGAATGG AGAGCCACCT CCACCCTGGC CGGCCTGGCC
                                                          BglI
    GCTAACCGGA ACTATAAGTG TTTGCTTACC TCTCGGTGGA GGTGGGACCG GCCGGACCGG
     S  Q  G    Q  Y  E    C  V  F  P    S  G  G    G  G  Q    G  A  Q  G
    cp8*
    ───▶     DD-DIS linker2
     T  S  G    Q  A  G    Q    G  G  G    G  S  A  E    G  D  D    P  A  K
661 ACTAGT GCC AGGCCGGCCA GGGTGGAGGT GGCTCTGCTG AGGGTGACGA TCCCGCAAAA
    SpeI    BglI
    TGATCA CGG TCCGGCCGGT CCCACCTCCA CCGAGACGAC TCCCACTGCT AGGGCGTTTT
         S  T
    ◀─── cp3*

A  A  F  N    S  L  Q    A  S  A    T  E  Y  I    G  Y  A    W  A  M
721 GCGGCCTTTA ACTCCCTGCA AGCCTCAGCG ACCGAATATA TCGGTTATGC GTGGGCGATG
    CGCCGGAAAT TGAGGGACGT TCGGAGTCGC TGGCTTATAT AGCCAATACG CACCCGCTAC

V  V  V  I    V  G  A    T  I  G    I  K  L  F    K  K  F    T  S  K
781 GTTGTTGTCA TTGTCGGCGC AACTATCGGT ATCAAGCTGT TTAAGAAATT CACCTCGAAA
    CAACAACAGT AACAGCCGCG TTGATAGCCA TAGTTCGACA AATTCTTTAA GTGGAGCTTT

A  S  stop
841 GCAAGCTGA
    CGTTCGACT
```

Figure 17

```
         BglI                        LacZp
   1 GGCCGGCCTG GCCGCGCAAC GCAATTAATG TGAGTTAGCT CACTCATTAG GCACCCCAGG
                             LacZp
  61 CTTTACACTT TATGCTTCCG GCTCGTATGT TGTGTGGAAT TGTGAGCGGA TAACAATTTC
       LacZp                          PelB starting Met
 121 ACACAAATTC TAAACTAGCT TAAGGAGACA GTCATAATGA AATACCTATT GCCTACGGCA
                                          SacI
 181 GCCGCTGGAT TGTTATTACT CGCTGCCCAA CCAGCCATGG CCGAGCTCCA GATGACCCAG
                XbaI
 241 TCTCCTTCCA CCCTCTAGAA CGCGTTAGTA AATACCTGTG ACGGAAGATC ACTTCGCAGA
 301 ATAAATAAAT CCTGGTGTCC CTGTTGATAC CGGGAAGCCC TGGGCCAACT TTTGGCGAAA
 361 ATGAGGCGTT GATCGGCACG TAAGAGGTTC CAACTTTCAC CATAATGAAA TAAGATCACT
                                                             CAT starting Met
 421 ACCGGGCGTA TTTTTTGAGT TGTCGAGATT TTCAGGAGCT AAGGAAGCTA AAATGGAGAA
 481 AAAAATTACT GGATATACCA CCGTTGATAT ATCCCAATGG CATCGTAAAG AACATTTTGA
 541 GGCATTTCAG TCAGTTGCTC AATGTACCTA TAACCAGACC GTTCAGCTGG ATATTACGGC
 601 CTTTTTAAAG ACCGTAAAGA AAAATAAGCA CAAGTTTTAT CCGGCCTTTA TTCACATTCT
 661 TGCCCGCCTG ATGAATGCTC ATCCGGAATT ACGTATGGCA ATGAAAGACG GTGAGCTGGT
 721 GATATGGGAT AGTGTTCACC CTTGTTACAC CGTTTTCCAT GAGCAAACTG AAACGTTTTC
 781 ATCGCTCTGG AGTGAATACC ACGACGATTT CCGGCAGTTT CTACACATAT ATTCGCAAGA
 841 TGTGGCGTGT TACGGTGAAA ACCTGGCCTA TTTCCCTAAA GGGTTTATTG AGAATATGTT
                                                       CAT stop codon
 901 TTTCGTCTCA GCCAATCCCT GGGGGAGTTC ACCAGTTTTG ATTTAAACGT GGCCAATATG
 961 GACAACTTCT TCGCCCCCGT TTTCACCATG GGCAAATATT ATACGCAAGG CGACAAGGTG
1021 CTGATGCCGC TGGCGATTCA GGTTCATCAT GCCGTTTGTG ATGGCTTCCA TGTCGGCAGA
1081 ATGCTTAATG AATTACAACA GTACTGCGAT GAGTGGCAGG GCGGGGCGTA ATTTTTTTAA
1141 GGCAGTTATT GGTGCCCTTA AACGCCTGGT GCTACGCCT GAATAAGTGA TAATAAGCGG
1201 ATGAATGGCA GAAATTCGAA AGCAAATTCG ACCCGGTCGT CGGTTCAGGG CAGGGTCGTT
1261 AAATAGCCGC TTATGTCTAT TGCTGGTTTA CCGGTTTATT GACTACCGGA AGCAGTGTGA
1321 CCGTGTGCTT CTCAAATGCC TGAGGCCAGT TTGCTCAGGC TCTCCCCGTG GAGGTAATAA
1381 TTGACGATAT GATCCTTTTT TTCTGATCAA AAGTGCTCAT CATTGGTTAC TAACGCGTCC
1441 ATGGGGCGGA GAATGGGCCG GAACTGGGCG GAGTTAGGGG CGGGATGGGC AGAGTCCATG
1501 GCTGACTAAT TTTTTTTATT TATGCAGAGG CCGAGGCCGC GGCCTCTGAG CTATTCCAGA
                      StuI
1561 AGTAGTGAGG AGGCTTTTTT GGAGGCCTAG GCTTTTGCAA AAAGCTCCCG GGAGCTTGGA
                                                                  LacZp
1621 TCGGGCTGCA GGAATTCACG ACAGGTTTCC CGACTGGAAA GCGGGCAGTG AGCGCAACGC
           LacZp
1681 AATTAATGTG AGTTAGCTCA CTCATTAGGC ACCCAGGCT TTACACTTTA TGCTTCCGGC
           LacZp
1741 TCGTATGTTG TGTGGAATTG TGAGCGGATA ACAATTTCAC ACAAATTCTA AACTAGCTTA
         PelB starting Met
1801 AGGAGACAGT CATAATGAAA TACCTATTGC CTACGGCAGC CGCTGGATTG TTATTACTCG
                                             XhoI
1861 CTGCCCAACC AGCCATGGCC CAGGTGAAAC TGCTCGAGTA TCCATATGAT GTTCCAGATT
        SpeI    BglI
1921 ATGCTACTAG TGGCCAGGCC GGCC
```

Figure 18

```
              BglI                          LacZp
    1 GGCCGGCCTG GCCGCGCAAC GCAATTAATG TGAGTTAGCT CACTCATTAG GCACCCCAGG
                    LacZp
   61 CTTTACACTT TATGCTTCCG GCTCGTATGT TGTGTGGAAT TGTGAGCGGA TAACAATTTC
       LacZp                              PelB starting Met
  121 ACACAAATTC TAAACTAGCT TAAGGAGACA GTCATAATGA AATACCTATT GCCTACGGCA
                                                        SacI
  181 GCCGCTGGAT TGTTATTACT CGCTGCCCAA CCAGCCATGG CCGAGCTCCA GATGACCCAG
                    XbaI
  241 TCTCCTTCCA CCCTCTAGAC ATGATAAGAT ACATTGATGA GTTTGGACAA ACCACAACTA 301 GAATGCAGTG AAAAAAATGC TTTATTTGTG AAATTTGTGA TGCTATTGCT TTATTTGTAA
                                                   ZEO stop codon
  361 CCATTATAAG CTGCAATAAA CAAGTTTCGA GGTCGAGTGT CAGTCCTGCT CCTCGGCCAC

421 GAAGTGCACG CAGTTGCCGG CCGGGTCGCG CAGGGCGAAC TCCCGTCCCC ACGGCTGCTC

481 GCCGATCTCG GTCATGGCCG GCCCGGAGGC GTCCCGGAAG TTCGTGGACA CGACCTCCGA

541 CCACTCGGCG TACAGCTCGT CCAGGCCGCG CACCCACACC CAGGCCAGGG TGTTGTCCGG

601 CACCACCTGG TCCTGGACCG CGCTGATGAA CAGGGTCACG TCGTCCCGGA CCACACCGGC

661 GAAGTCGTCC TCCACGAAGT CCCGGGAGAA CCCGAGCCGG TCGGTCCAGA ACTCGACCGC
                                                    ZEO starting Met
  721 TCCGGCGACG TCGCGCGCGG TGAGCACCGG AACGGCACTG GTCAACTTGG CCATGGTTTA 781 GTTCCTCACC TTGTCGTATT ATACTATGCC GATATACTAT GCCGATGATT AATTGTCAAC
       StuI
  841 AAGGCCTAGG CTTTTGCAAA AAGCTCCCGG GAGCTTGGAT CGGGCTGCAG GAATTCACGA
                                                            LacZp
  901 CAGGTTTCCC GACTGGAAAG CGGGCAGTGA GCGCACGCA ATTAATGTGA GTTAGCTCAC
           LacZp
  961 TCATTAGGCA CCCCAGGCTT TACACTTTAT GCTTCCGGCT CGTATGTTGT GTGGAATTGT
         LacZp                                       PelB starting Met
 1021 GAGCGGATAA CAATTTCACA CAAATTCTAA ACTAGCTTAA GGAGACAGTC ATAATGAAAT 1081 ACCTATTGCC TACGGCAGCC GCTGGATTGT TATTACTCGC TGCCCAACCA GCCATGGCCC
              XhoI                                 SpeI       BglI
 1141 AGGTGAAACT GCTCGAGTAT CCATATGATG TTCCAGATTA TGCTACTAGT GGCCAGGCCG

1201 GCC
```

Figure 20
A)
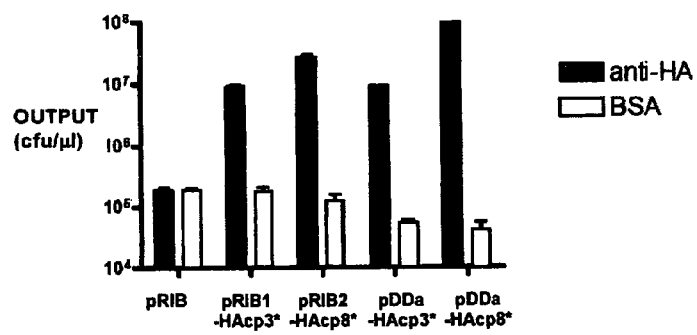
B)
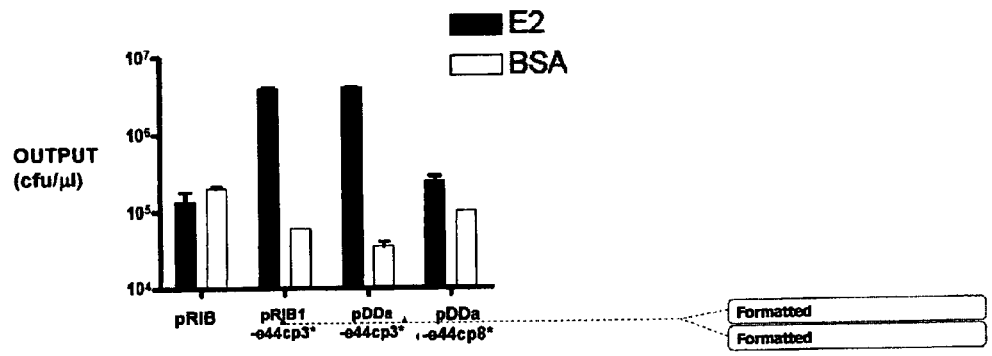

Figure 21
A)
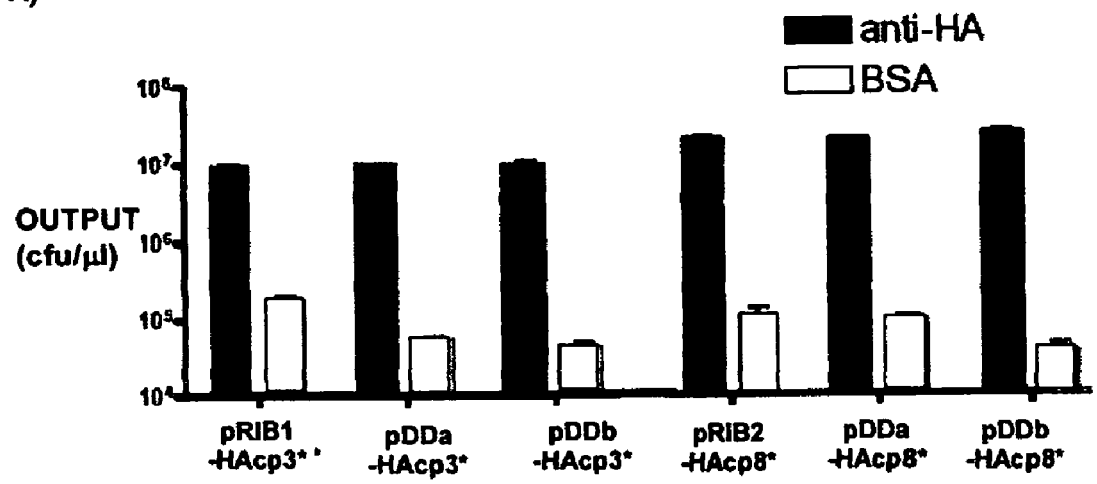
B)
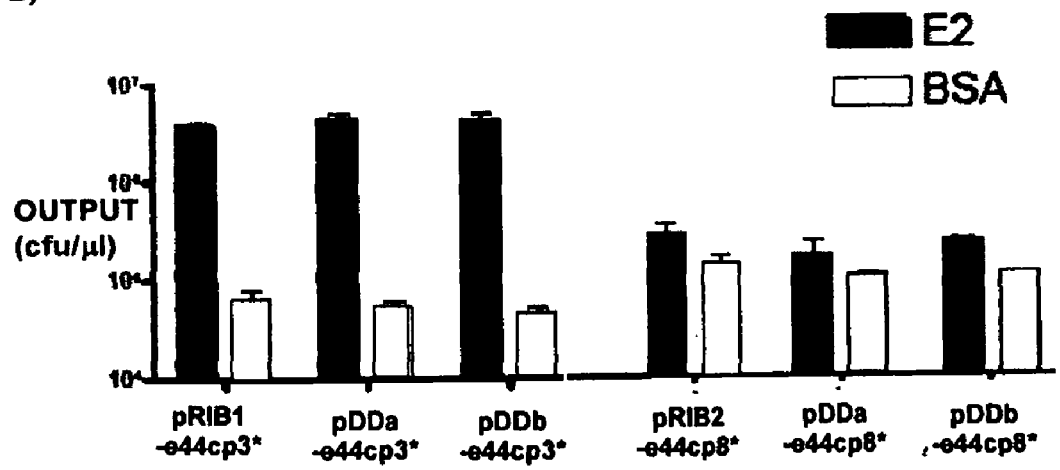

Figure 22
A)
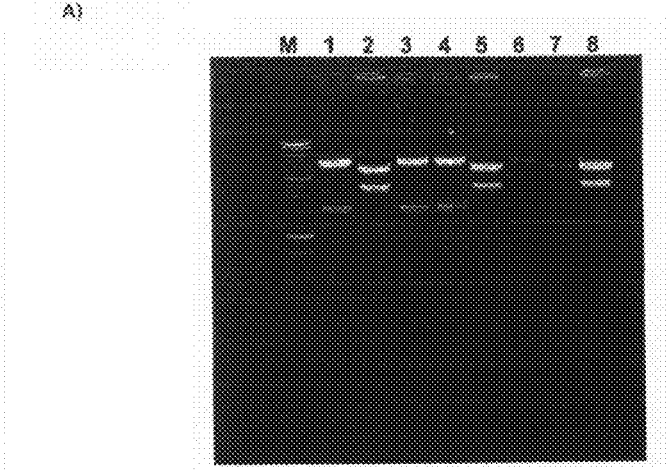
B)
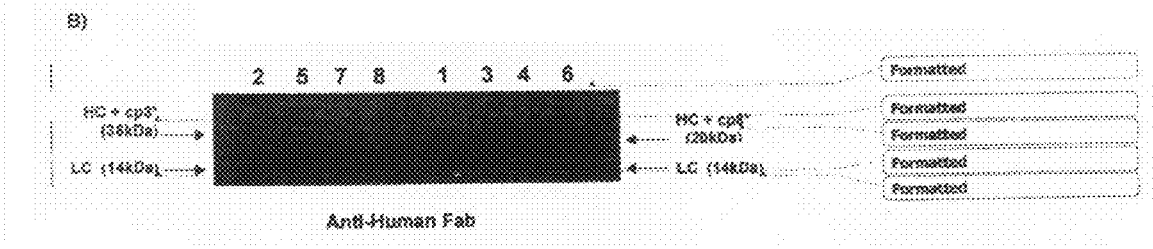

SEQUENCE LISTING

```
<160> NUMBER OF SEQ ID NOS: 56

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
actagtggcc aggccggcc                                                 19

<210> SEQ ID NO 2
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(36)

<400> SEQUENCE: 2 act agt ggc cag gcc ggc cag ggt ggc ggt ggc tct                      36
Thr Ser Gly Gln Ala Gly Gln Gly Gly Gly Gly Ser
 1               5                  10

<210> SEQ ID NO 3
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Thr Ser Gly Gln Ala Gly Gln Gly Gly Gly Gly Ser
 1               5                  10

<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
gccggcctgg ccactagtgg ccaggccggc                                     30

<210> SEQ ID NO 5
<211> LENGTH: 66
```

<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 5

```
agagccacct ccaccctggc cggcctggcc actagtggcc aggccggcca gggtggaggt    60
ggctct                                                               66
```

<210> SEQ ID NO 6
<211> LENGTH: 672
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: CDS
<222> LOCATION: (1)..(663)

<400> SEQUENCE: 6

```
act agt ggc cag gcc ggc cag ggt ggc ggt ggc tct cca ttc gtt tgt      48
Thr Ser Gly Gln Ala Gly Gln Gly Gly Gly Gly Ser Pro Phe Val Cys
 1               5                  10                  15 gaa tat caa ggc caa tcg tct gac ctg cct caa cct cct gtc aat gct      96
Glu Tyr Gln Gly Gln Ser Ser Asp Leu Pro Gln Pro Pro Val Asn Ala
                20                  25                  30 ggc ggc ggc tct ggt ggt ggt tct ggt ggc ggc tct gag ggt ggt ggc     144
Gly Gly Gly Ser Gly Gly Gly Ser Gly Gly Gly Ser Glu Gly Gly Gly
            35                  40                  45 tct gag ggt ggc ggt tct gag ggt ggc ggc tct gag gga ggc ggt tcc     192
Ser Glu Gly Gly Gly Ser Glu Gly Gly Gly Ser Glu Gly Gly Gly Ser
        50                  55                  60 ggt ggc ggc tct ggt tct ggt gat ttt gat tat gaa aag atg gca aac     240
Gly Gly Gly Ser Gly Ser Gly Asp Phe Asp Tyr Glu Lys Met Ala Asn
65                  70                  75                  80 gct aat aag ggg gct atg acc gaa aat gcc gat gaa aac gcg cta cag     288
Ala Asn Lys Gly Ala Met Thr Glu Asn Ala Asp Glu Asn Ala Leu Gln
                85                  90                  95 tct gac gct aaa ggc aaa ctt gat tct gtc gct act gat tac ggt gct     336
Ser Asp Ala Lys Gly Lys Leu Asp Ser Val Ala Thr Asp Tyr Gly Ala
            100                 105                 110 gct atc gat ggt ttc att ggt gac gtt tcc ggc ctt gct aat ggt aat     384
Ala Ile Asp Gly Phe Ile Gly Asp Val Ser Gly Leu Ala Asn Gly Asn
        115                 120                 125 ggt gct act ggt gat ttt gct ggc tct aat tcc caa atg gct caa gtc     432
Gly Ala Thr Gly Asp Phe Ala Gly Ser Asn Ser Gln Met Ala Gln Val
    130                 135                 140 ggt gac ggt gat aat tca cct tta atg aat aat ttc cgt caa tat tta     480
Gly Asp Gly Asp Asn Ser Pro Leu Met Asn Asn Phe Arg Gln Tyr Leu
145                 150                 155                 160 cct tcc ctc cct caa tcg gtt gaa tgt cgc cct ttt gtc ttt ggc gct     528
Pro Ser Leu Pro Gln Ser Val Glu Cys Arg Pro Phe Val Phe Gly Ala
                165                 170                 175 ggt aaa cca tat gaa ttt tct att gat tgt gac aaa ata aac tta ttc     576
Gly Lys Pro Tyr Glu Phe Ser Ile Asp Cys Asp Lys Ile Asn Leu Phe
            180                 185                 190 cgt ggt gtc ttt gcg ttt ctt tta tat gtt gcc acc ttt atg tat gta     624
Arg Gly Val Phe Ala Phe Leu Leu Tyr Val Ala Thr Phe Met Tyr Val
        195                 200                 205 ttt tct acg ttt gct aac ata ctg cgt aat aag gag tct taagctagc      672
Phe Ser Thr Phe Ala Asn Ile Leu Arg Asn Lys Glu Ser
    210                 215
```

Phe Ser Thr Phe Ala Asn Ile Leu Arg Asn Lys Glu Ser
    210                 215                 220

<210> SEQ ID NO 7
<211> LENGTH: 221
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Thr Ser Gly Gln Ala Gly Gln Gly Gly Gly Ser Pro Phe Val Cys
 1               5                  10                  15

Glu Tyr Gln Gly Gln Ser Ser Asp Leu Pro Gln Pro Val Asn Ala
                20                  25                  30

Gly Gly Gly Ser Gly Gly Gly Ser Gly Gly Gly Ser Glu Gly Gly Gly
                35                  40                  45

Ser Glu Gly Gly Gly Ser Glu Gly Gly Ser Glu Gly Gly Ser
 50                  55                  60

Gly Gly Gly Ser Gly Ser Gly Asp Phe Asp Tyr Glu Lys Met Ala Asn
 65                  70                  75                  80

Ala Asn Lys Gly Ala Met Thr Glu Asn Ala Asp Glu Asn Ala Leu Gln
                85                  90                  95

Ser Asp Ala Lys Gly Lys Leu Asp Ser Val Ala Thr Asp Tyr Gly Ala
                100                 105                 110

Ala Ile Asp Gly Phe Ile Gly Asp Val Ser Gly Leu Ala Asn Gly Asn
                115                 120                 125

Gly Ala Thr Gly Asp Phe Ala Gly Ser Asn Ser Gln Met Ala Gln Val
                130                 135                 140

Gly Asp Gly Asp Asn Ser Pro Leu Met Asn Asn Phe Arg Gln Tyr Leu
145                 150                 155                 160

Pro Ser Leu Pro Gln Ser Val Glu Cys Arg Pro Phe Val Phe Gly Ala
                165                 170                 175

Gly Lys Pro Tyr Glu Phe Ser Ile Asp Cys Asp Lys Ile Asn Leu Phe
                180                 185                 190

Arg Gly Val Phe Ala Phe Leu Leu Tyr Val Ala Thr Phe Met Tyr Val
                195                 200                 205

Phe Ser Thr Phe Ala Asn Ile Leu Arg Asn Lys Glu Ser
    210                 215                 220

<210> SEQ ID NO 8
<211> LENGTH: 195
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(186)

<400> SEQUENCE: 8 act agt ggc cag gcc ggc cag ggt ggc ggt ggc tct gct gag ggt gac    48
Thr Ser Gly Gln Ala Gly Gln Gly Gly Gly Ser Ala Glu Gly Asp
 1               5                  10                  15 gat ccc gca aaa gcg gcc ttt aac tcc ctg caa gcc tca gcg acc gaa    96
Asp Pro Ala Lys Ala Ala Phe Asn Ser Leu Gln Ala Ser Ala Thr Glu
                20                  25                  30 tat atc ggt tat gcg tgg gcg atg gtt gtt gtc att gtc ggc gca act   144

```
Tyr Ile Gly Tyr Ala Trp Ala Met Val Val Val Ile Val Gly Ala Thr
        35                  40                  45 atc ggt atc aag ctg ttt aag aaa ttc acc tcg aaa gca agc tgagctagc      195
Ile Gly Ile Lys Leu Phe Lys Lys Phe Thr Ser Lys Ala Ser
    50                  55                  60

<210> SEQ ID NO 9
<211> LENGTH: 62
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Thr Ser Gly Gln Ala Gly Gln Gly Gly Gly Ser Ala Glu Gly Asp
1               5                   10                  15

Asp Pro Ala Lys Ala Ala Phe Asn Ser Leu Gln Ala Ser Ala Thr Glu
            20                  25                  30

Tyr Ile Gly Tyr Ala Trp Ala Met Val Val Val Ile Val Gly Ala Thr
        35                  40                  45

Ile Gly Ile Lys Leu Phe Lys Lys Phe Thr Ser Lys Ala Ser
    50                  55                  60

<210> SEQ ID NO 10
<211> LENGTH: 849
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (661)..(846)

<400> SEQUENCE: 10
ttaagactcc ttattacgca gtatgttagc aaacgtagaa aatacataca taaaggtggc      60
aacatataaa agaaacgcaa agacaccacg gaataagttt attttgtcac aatcaataga     120
aaattcatat ggtttaccag cgctaaagac aaaagggcga cattcaaccg attgagggag     180
ggaaggtaaa tattgacgga aattattcat taaaggtgaa ttatcaccgt caccgacttg     240
agccatttgg gaattagagc cagcaaaatc accagtagca ccattaccat tagcaaggcc     300
ggaaacgtca ccaatgaaac catcgatagc agcaccgtaa tcagtagcga cagaatcaag     360
tttgccttta gcgtcagact gtagcgcgtt ttcatcggca ttttcggtca tagcccccct     420
attagcgttt gccatctttt cataatcaaa atcaccggaa ccagagccac caccggaacc     480
gcctccctca gagccgccac cctcagaacc gccaccctca gagccaccac cctcagagcc     540
gccaccagaa ccaccaccag agccgccgcc agcattgaca ggaggttgag gcaggtcaga     600
cgattggcct tgatattcac aaacgaatgg agagccacct ccaccctggc cggcctggcc     660 act agt ggc cag gcc ggc cag ggt gga ggt ggc tct gct gag ggt gac      708
Thr Ser Gly Gln Ala Gly Gln Gly Gly Gly Gly Ser Ala Glu Gly Asp
1               5                   10                  15 gat ccc gca aaa gcg gcc ttt aac tcc ctg caa gcc tca gcg acc gaa      756
Asp Pro Ala Lys Ala Ala Phe Asn Ser Leu Gln Ala Ser Ala Thr Glu
            20                  25                  30 tat atc ggt tat gcg tgg gcg atg gtt gtt gtc att gtc ggc gca act      804
Tyr Ile Gly Tyr Ala Trp Ala Met Val Val Val Ile Val Gly Ala Thr
        35                  40                  45 atc ggt atc aag ctg ttt aag aaa ttc acc tcg aaa gca agc tga           849
Ile Gly Ile Lys Leu Phe Lys Lys Phe Thr Ser Lys Ala Ser
    50                  55                  60
```

```
Ile Gly Ile Lys Leu Phe Lys Lys Phe Thr Ser Lys Ala Ser
 50              55                  60
```

<210> SEQ ID NO 11
<211> LENGTH: 1944
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11

| | | | | | |
|---|---|---|---|---|---|
| ggccggcctg | gccgcgcaac | gcaattaatg | tgagttagct | cactcattag | gcaccccagg | 60 |
| ctttacactt | tatgcttccg | gctcgtatgt | tgtgtggaat | tgtgagcgga | taacaatttc | 120 |
| acacaaattc | taaactagct | taaggagaca | gtcataatga | ataccctatt | gcctacggca | 180 |
| gccgctggat | tgttattact | cgctgcccaa | ccagccatgg | ccgagctcca | gatgacccag | 240 |
| tctccttcca | ccctctagaa | cgcgttagta | aatacctgtg | acggaagatc | acttcgcaga | 300 |
| ataaataaat | cctggtgtcc | ctgttgatac | cgggaagccc | tgggccaact | tttggcgaaa | 360 |
| atgaggcgtt | gatcggcacg | taagaggttc | caactttcac | cataatgaaa | taagatcact | 420 |
| accgggcgta | ttttttgagt | tgtcgagatt | ttcaggagct | aaggaagcta | aaatggagaa | 480 |
| aaaaattact | ggatatacca | ccgttgatat | atcccaatgg | catcgtaaag | aacattttga | 540 |
| ggcatttcag | tcagttgctc | aatgtaccta | taaccagacc | gttcagctgg | atattacggc | 600 |
| cttttttaaag | accgtaaaga | aaaataagca | caagttttat | ccggccttta | ttcacattct | 660 |
| tgcccgcctg | atgaatgctc | atccggaatt | acgtatggca | atgaaagacg | gtgagctggt | 720 |
| gatatgggat | agtgttcacc | cttgttacac | cgttttccat | gagcaaactg | aaacgttttc | 780 |
| atcgctctgg | agtgaatacc | acgacgattt | ccggcagttt | ctacacatat | attcgcaaga | 840 |
| tgtggcgtgt | tacggtgaaa | acctggccta | tttccctaaa | gggtttattg | agaatatgtt | 900 |
| tttcgtctca | gccaatccct | gggggagttc | accagttttg | atttaaacgt | ggccaatatg | 960 |
| gacaacttct | tcgcccccgt | tttcaccatg | ggcaaatatt | atacgcaagg | cgacaaggtg | 1020 |
| ctgatgccgc | tggcgattca | ggttcatcat | gccgtttgtg | atggcttcca | tgtcggcaga | 1080 |
| atgcttaatg | aattacaaca | gtactgcgat | gagtggcagg | cggggcgta | attttttaa | 1140 |
| ggcagttatt | ggtgccctta | aacgcctggt | tgctacgcct | gaataagtga | taataagcgg | 1200 |
| atgaatggca | gaaattcgaa | agcaaattcg | acccggtcgt | cggttcaggg | cagggtcgtt | 1260 |
| aaatagccgc | ttatgtctat | tgctggttta | ccggtttatt | gactaccgga | agcagtgtga | 1320 |
| ccgtgtgctt | ctcaaatgcc | tgaggccagt | ttgctcaggc | tctcccgtg | gaggtaataa | 1380 |
| ttgacgatat | gatccttttt | ttctgatcaa | aagtgctcat | cattggttac | taacgcgtcc | 1440 |
| atggggcgga | gaatgggccg | gaactgggcg | gagttagggg | cgggatgggc | agagtccatg | 1500 |
| gctgactaat | tttttttatt | tatgcagagg | ccgaggccgc | ggcctctgag | ctattccaga | 1560 |
| agtagtgagg | aggctttttt | ggaggcctag | gcttttgcaa | aaagctcccg | ggagcttgga | 1620 |
| tcgggctgca | ggaattcacg | acaggtttcc | cgactggaaa | gcgggcagtg | agcgcaacgc | 1680 |
| aattaatgtg | agttagctca | ctcattaggc | accccaggct | ttacacttta | tgcttccggc | 1740 |
| tcgtatgttg | tgtggaattg | tgagcggata | acaatttcac | acaaattcta | aactagctta | 1800 |
| aggagacagt | cataatgaaa | tacctattgc | ctacggcagc | cgctggattg | ttattactcg | 1860 |
| ctgcccaacc | agccatggcc | caggtgaaac | tgctcgagta | tccatatgat | gttccagatt | 1920 |
| atgctactag | tggccaggcc | ggcc | | | | 1944 |

<210> SEQ ID NO 12
<211> LENGTH: 1203
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12

| | | |
|---|---|---|
| ggccggcctg gccgcgcaac gcaattaatg tgagttagct cactcattag gcacccagg | 60 |
| ctttacactt tatgcttccg gctcgtatgt tgtgtggaat tgtgagcgga taacaatttc | 120 |
| acacaaattc taaactagct taaggagaca gtcataatga atacctatt gcctacggca | 180 |
| gccgctggat tgttattact cgctgcccaa ccagccatgg ccgagctcca gatgacccag | 240 |
| tctccttcca ccctctagac atgataagat acattgatga gtttggacaa accacaacta | 300 |
| gaatgcagtg aaaaaaatgc tttatttgtg aaatttgtga tgctattgct ttatttgtaa | 360 |
| ccattataag ctgcaataaa caagtttcga ggtcgagtgt cagtcctgct cctcggccac | 420 |
| gaagtgcacg cagttgccgg ccgggtcgcg cagggcgaac tcccgtcccc acggctgctc | 480 |
| gccgatctcg gtcatggccg gcccggaggc gtcccggaag ttcgtggaca cgacctccga | 540 |
| ccactcggcg tacagctcgt ccaggccgcg cacccacacc caggccaggg tgttgtccgg | 600 |
| caccacctgg tcctggaccg cgctgatgaa cagggtcacg tcgtcccgga ccacaccggc | 660 |
| gaagtcgtcc tccacgaagt cccgggagaa cccgagccgg tcggtccaga actcgaccgc | 720 |
| tccggcgacg tcgcgcgcgg tgagcaccgg aacggcactg gtcaacttgg ccatggttta | 780 |
| gttcctcacc ttgtcgtatt atactatgcc gatatactat gccgatgatt aattgtcaac | 840 |
| aaggcctagg cttttgcaaa aagctcccgg gagcttggat cgggctgcag gaattcacga | 900 |
| caggtttccc gactggaaag cgggcagtga gcgcaacgca attaatgtga gttagctcac | 960 |
| tcattaggca ccccaggctt tacactttat gcttccggct cgtatgttgt gtggaattgt | 1020 |
| gagcggataa caatttcaca caaattctaa actagcttaa ggagacagtc ataatgaaat | 1080 |
| acctattgcc tacggcagcc gctggattgt tattactcgc tgcccaacca gccatggccc | 1140 |
| aggtgaaact gctcgagtat ccatatgatg ttccagatta tgctactagt ggccaggccg | 1200 |
| gcc | 1203 |

<210> SEQ ID NO 13
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gacaaaacta gtggccaggc cggccagggt ggcggtggct ctcca     45

<210> SEQ ID NO 14
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gtggtggcta gcttaagact ccttatt     27

-continued

<210> SEQ ID NO 15
<211> LENGTH: 57
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
actagtggcc aggccggcca gggtggcggt ggctctgctg agggtgacga tcccgca        57

<210> SEQ ID NO 16
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
gtggtggcta gctcagcttg ctttcgaggt gaattt                               36

<210> SEQ ID NO 17
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
tcgagtatcc atatgatgtt ccagattatg cta                                  33

<210> SEQ ID NO 18
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
ctagtagcat aatctggaac atcatatgga tac                                  33

<210> SEQ ID NO 19
<211> LENGTH: 774
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(774)

<400> SEQUENCE: 19

```
atg aaa tac cta ttg cct acg gca gcc gct gga ttg tta tta ctc gct          48
Met Lys Tyr Leu Leu Pro Thr Ala Ala Ala Gly Leu Leu Leu Leu Ala
 1               5                  10                  15 gcc caa cca gcc atg gcc cag gtg aaa ctg ctc gag tat cca tat gat          96
Ala Gln Pro Ala Met Ala Gln Val Lys Leu Leu Glu Tyr Pro Tyr Asp
             20                  25                  30 gtt cca gat tat gct act agt ggc cag gcc ggc cag ggt ggc ggt ggc         144
Val Pro Asp Tyr Ala Thr Ser Gly Gln Ala Gly Gln Gly Gly Gly Gly
         35                  40                  45
```

-continued

```
tct cca ttc gtt tgt gaa tat caa ggc caa tcg tct gac ctg cct caa      192
Ser Pro Phe Val Cys Glu Tyr Gln Gly Gln Ser Ser Asp Leu Pro Gln
 50                  55                  60 cct cct gtc aat gct ggc ggc ggc tct ggt ggt ggt tct ggt ggc ggc      240
Pro Pro Val Asn Ala Gly Gly Gly Ser Gly Gly Gly Ser Gly Gly Gly
 65                  70                  75                  80 tct gag ggt ggt ggc tct gag ggt ggc ggt tct gag ggt ggc ggc tct      288
Ser Glu Gly Gly Gly Ser Glu Gly Gly Gly Ser Glu Gly Gly Gly Ser
                 85                  90                  95 gag gga ggc ggt tcc ggt ggt ggc tct ggt tcc ggt gat ttt gat tat      336
Glu Gly Gly Gly Ser Gly Gly Gly Ser Gly Ser Gly Asp Phe Asp Tyr
            100                 105                 110 gaa aag atg gca aac gct aat aag ggg gct atg acc gaa aat gcc gat      384
Glu Lys Met Ala Asn Ala Asn Lys Gly Ala Met Thr Glu Asn Ala Asp
        115                 120                 125 gaa aac gcg cta cag tct gac gct aaa ggc aaa ctt gat tct gtc gct      432
Glu Asn Ala Leu Gln Ser Asp Ala Lys Gly Lys Leu Asp Ser Val Ala
130                 135                 140 act gat tac ggt gct gct atc gat ggt ttc att ggt gac gtt tcc ggc      480
Thr Asp Tyr Gly Ala Ala Ile Asp Gly Phe Ile Gly Asp Val Ser Gly
145                 150                 155                 160 ctt gct aat ggt aat ggt gct act ggt gat ttt gct ggc tct aat tcc      528
Leu Ala Asn Gly Asn Gly Ala Thr Gly Asp Phe Ala Gly Ser Asn Ser
                165                 170                 175 caa atg gct caa gtc ggt gac ggt gat aat tca cct tta atg aat aat      576
Gln Met Ala Gln Val Gly Asp Gly Asp Asn Ser Pro Leu Met Asn Asn
            180                 185                 190 ttc cgt caa tat tta cct tcc ctc cct caa tcg gtt gaa tgt cgc cct      624
Phe Arg Gln Tyr Leu Pro Ser Leu Pro Gln Ser Val Glu Cys Arg Pro
        195                 200                 205 ttt gtc ttt ggc gct ggt aaa cca tat gaa ttt tct att gat tgt gac      672
Phe Val Phe Gly Ala Gly Lys Pro Tyr Glu Phe Ser Ile Asp Cys Asp
210                 215                 220 aaa ata aac tta ttc cgt ggt gtc ttt gcg ttt ctt tta tat gtt gcc      720
Lys Ile Asn Leu Phe Arg Gly Val Phe Ala Phe Leu Leu Tyr Val Ala
225                 230                 235                 240 acc ttt atg tat gta ttt tct acg ttt gct aac ata ctg cgt aat aag      768
Thr Phe Met Tyr Val Phe Ser Thr Phe Ala Asn Ile Leu Arg Asn Lys
                245                 250                 255 gag tct                                                              774
Glu Ser
```

<210> SEQ ID NO 20
<211> LENGTH: 258
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

```
Met Lys Tyr Leu Leu Pro Thr Ala Ala Ala Gly Leu Leu Leu Leu Ala
 1               5                  10                  15

Ala Gln Pro Ala Met Ala Gln Val Lys Leu Leu Glu Tyr Pro Tyr Asp
                20                  25                  30

Val Pro Asp Tyr Ala Thr Ser Gly Gln Ala Gly Gln Gly Gly Gly Gly
            35                  40                  45

Ser Pro Phe Val Cys Glu Tyr Gln Gly Gln Ser Ser Asp Leu Pro Gln
 50                  55                  60

Pro Pro Val Asn Ala Gly Gly Gly Ser Gly Gly Gly Ser Gly Gly Gly
```

```
               65                  70                  75                  80
Ser Glu Gly Gly Gly Ser Glu Gly Gly Gly Ser Glu Gly Gly Gly Ser
                        85                  90                  95

Glu Gly Gly Gly Ser Gly Gly Ser Gly Ser Gly Asp Phe Asp Tyr
            100                 105                 110

Glu Lys Met Ala Asn Ala Asn Lys Gly Ala Met Thr Glu Asn Ala Asp
        115                 120                 125

Glu Asn Ala Leu Gln Ser Asp Ala Lys Gly Lys Leu Asp Ser Val Ala
    130                 135                 140

Thr Asp Tyr Gly Ala Ala Ile Asp Gly Phe Ile Gly Asp Val Ser Gly
145                 150                 155                 160

Leu Ala Asn Gly Asn Gly Ala Thr Gly Asp Phe Ala Gly Ser Asn Ser
                165                 170                 175

Gln Met Ala Gln Val Gly Asp Gly Asp Asn Ser Pro Leu Met Asn Asn
            180                 185                 190

Phe Arg Gln Tyr Leu Pro Ser Leu Pro Gln Ser Val Glu Cys Arg Pro
        195                 200                 205

Phe Val Phe Gly Ala Gly Lys Pro Tyr Glu Phe Ser Ile Asp Cys Asp
    210                 215                 220

Lys Ile Asn Leu Phe Arg Gly Val Phe Ala Phe Leu Leu Tyr Val Ala
225                 230                 235                 240

Thr Phe Met Tyr Val Phe Ser Thr Phe Ala Asn Ile Leu Arg Asn Lys
                245                 250                 255

Glu Ser

<210> SEQ ID NO 21
<211> LENGTH: 297
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(297)

<400> SEQUENCE: 21 atg aaa tac cta ttg cct acg gca gcc gct gga ttg tta tta ctc gct     48
Met Lys Tyr Leu Leu Pro Thr Ala Ala Ala Gly Leu Leu Leu Leu Ala
  1               5                  10                  15 gcc caa cca gcc atg gcc cag gtg aaa ctg ctc gag tat cca tat gat     96
Ala Gln Pro Ala Met Ala Gln Val Lys Leu Leu Glu Tyr Pro Tyr Asp
             20                  25                  30 gtt cca gat tat gct act agt ggc cag gcc ggc cag ggt ggc ggt ggc    144
Val Pro Asp Tyr Ala Thr Ser Gly Gln Ala Gly Gln Gly Gly Gly Gly
         35                  40                  45 tct gct gag ggt gac gat ccc gca aaa gcg gcc ttt aac tcc ctg caa    192
Ser Ala Glu Gly Asp Asp Pro Ala Lys Ala Ala Phe Asn Ser Leu Gln
     50                  55                  60 gcc tca gcg acc gaa tat atc ggt tat gcg tgg gcg atg gtt gtt gtc    240
Ala Ser Ala Thr Glu Tyr Ile Gly Tyr Ala Trp Ala Met Val Val Val
 65                  70                  75                  80 att gtc ggc gca act atc ggt atc aag ctg ttt aag aaa ttc acc tcg    288
Ile Val Gly Ala Thr Ile Gly Ile Lys Leu Phe Lys Lys Phe Thr Ser
                 85                  90                  95 aaa gca agc                                                        297
Lys Ala Ser
```

<210> SEQ ID NO 22
<211> LENGTH: 99
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Met Lys Tyr Leu Leu Pro Thr Ala Ala Ala Gly Leu Leu Leu Leu Ala
 1               5                  10                  15

Ala Gln Pro Ala Met Ala Gln Val Lys Leu Leu Glu Tyr Pro Tyr Asp
            20                  25                  30

Val Pro Asp Tyr Ala Thr Ser Gly Gln Ala Gly Gln Gly Gly Gly Gly
        35                  40                  45

Ser Ala Glu Gly Asp Asp Pro Ala Lys Ala Ala Phe Asn Ser Leu Gln
 50                  55                  60

Ala Ser Ala Thr Glu Tyr Ile Gly Tyr Ala Trp Ala Met Val Val Val
 65                  70                  75                  80

Ile Val Gly Ala Thr Ile Gly Ile Lys Leu Phe Lys Lys Phe Thr Ser
                 85                  90                  95

Lys Ala Ser

<210> SEQ ID NO 23
<211> LENGTH: 109
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
cgcaacgcaa ttaatgtgag ttagctcact cattaggcac cccaggcttt acactttatg        60
cttccggctc gtatgttgtg tggaattgtg agcggataac aatttcaca               109

<210> SEQ ID NO 24
<211> LENGTH: 99
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
aaggagacag tcataatgaa atacctattg cctacggcag ccgctggatt gttattactc        60
gctgcccaac cagccatggc ccaggtgaaa ctgctcgag                            99

<210> SEQ ID NO 25
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Met Lys Tyr Leu Leu Pro Thr Ala Ala Ala Gly Leu Leu Leu Leu Ala
 1               5                  10                  15

Ala Gln Pro Ala Met Ala Gln Val Lys Leu Leu Glu
            20                  25

<210> SEQ ID NO 26

```
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
ccagatgacc cagtctcctt ccaccct                                           27

<210> SEQ ID NO 27
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
ctagagggtg aaggagact gggtcatctg gagct                                   35

<210> SEQ ID NO 28
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
gcgcgtccca ttcgacattc aggctgcgc                                         29

<210> SEQ ID NO 29
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
gcgcagcctg aatgtcgaat gggacgcgc                                         29

<210> SEQ ID NO 30
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
ttctgcgctc ggcacttccg gctggct                                           27

<210> SEQ ID NO 31
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
agccagccgg aagtgccgag cgcagaa                                           27

<210> SEQ ID NO 32
<211> LENGTH: 42
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
ctggctagca aaggccaggc cggccaaaga attcgctctt cc                          42

<210> SEQ ID NO 33
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
agcggaagag cgaattcttt ggccggcctg gcctttgcta gccag                       45

<210> SEQ ID NO 34
<211> LENGTH: 268
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 34
gcgcgtaata cgactcacta tagggcgaat tgggtaccgg ccccccctcg aggtcgacgg       60
tatcgataag cttgatatcg aattcctgca gcccggggga tccactagtt ctagagcggc      120
cgccaccgcg gtggagctcc agcttttgtt ccctttagtg agggttaatt gcgcgcttgg      180
cgtaatcatg gtcatagctg tttcctgtaa attgttatcc gctcacaatt ccacacaaca      240
tacgagccgg aagcatgcta gccagctg                                         268

<210> SEQ ID NO 35
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
gcgcgtaata cgactcacta tagggc                                           26

<210> SEQ ID NO 36
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
cagctggcta gcatgcttcc ggctcgtatg ttgtg                                 35

<210> SEQ ID NO 37
<211> LENGTH: 23
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 37
ccggccaggg tggaggtggc tct                                             23

<210> SEQ ID NO 38
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
agagccacct ccaccctggc cgg                                             23

<210> SEQ ID NO 39
<211> LENGTH: 666
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 39
actagtggcc aggccggcca gggtggaggt ggctctccat tcgtttgtga atatcaaggc     60
caatcgtctg acctgcctca acctcctgtc aatgctggcg gcggtctctgg tggtggttct  120 ggtggcggct ctgagggtgg tggctctgag ggtggcggtt ctgagggtgg cggctctgag   180
ggaggcggtt ccgtggtggg ctctggttcc ggtgattttg attatgaaaa gatggcaaac   240
gctaataagg gggctatgac cgaaaatgcc gatgaaaacg cgctacagtc tgacgctaaa   300
ggcaaacttg attctgtcgc tactgattac ggtgctgcta tcgatggttt cattggtgac   360
gtttccggcc ttgctaatgg taatggtgct actggtgatt ttgctggctc taattcccaa   420
atggctcaag tcggtgacgg tgataattca cctttaatga ataatttccg tcaatattta   480
ccttccctcc ctcaatcggt tgaatgtcgc ccttttgtct ttagcgctgg taaaccatat   540
gaattttcta ttgattgtga caaaataaac ttattccgtg gtgtctttgc gtttcttttta  600 tatgttgcca cctttatgta tgtattttct acgtttgcta acatactgcg taataaggag   660
tcttaa                                                              666

<210> SEQ ID NO 40
<211> LENGTH: 189
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 40
actagtggcc aggccggcca gggtggaggt ggctctgctg agggtgacga tcccgcaaaa     60
gcggccttta actccctgca agcctcagcg accgaatata tcggttatgc gtgggcgatg   120
gttgttgtca ttgtcggcgc aactatcggt atcaagctgt taagaaaatt cacctcgaaa   180
gcaagctga                                                           189

<210> SEQ ID NO 41
<211> LENGTH: 27
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 41
atgtactagt ggccaggccg gccaggg                                          27

<210> SEQ ID NO 42
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
ggaatcctag aattctcagc ttgctttcga ggtgaat                               37

<210> SEQ ID NO 43
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
aatgagtagg ccttgttgac aattaatcat cggcatagt                             39

<210> SEQ ID NO 44
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
aactggatct agacatgata agatacaaca ttgatgagtt tgg                        43

<210> SEQ ID NO 45
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
aatgagtagg ccttgttgac aattaatcat cggcatagt                             39

<210> SEQ ID NO 46
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
aactggatct agacatgata agatacattg atgagtttgg                            40

<210> SEQ ID NO 47
<211> LENGTH: 28
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 47
gagcagccgt ggggacggga gttcgccc                                            28

<210> SEQ ID NO 48
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
gggcgaactc ccgtccccac ggctgctc                                            28

<210> SEQ ID NO 49
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
cagctggcta gcaaaggcca ggccggccaa agaattcgct cttccgctt                     49

<210> SEQ ID NO 50
<211> LENGTH: 849
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (184)..(846)

<400> SEQUENCE: 50
tcagcttgct ttcgaggtga atttcttaaa cagcttgata ccgatagttg cgccgacaat         60
gacaacaacc atcgcccacg cataaccgat atattcggtc gctgaggctt cagggagtt         120 aaaggccgct tttgcgggat cgtcaccctc agcagagcca cctccaccct ggccggcctg        180 gcc act agt ggc cag gcc ggc cag ggt gga ggt ggc tct cca ttc gtt          228
    Thr Ser Gly Gln Ala Gly Gln Gly Gly Gly Gly Ser Pro Phe Val
    1               5                   10                  15 tgt gaa tat caa ggc caa tcg tct gac ctg cct caa cct cct gtc aat          276
Cys Glu Tyr Gln Gly Gln Ser Ser Asp Leu Pro Gln Pro Pro Val Asn
                20                  25                  30 gct ggc ggc ggc tct ggt ggt ggt tct ggt ggc ggc tct gag ggt ggt          324
Ala Gly Gly Gly Ser Gly Gly Gly Ser Gly Gly Gly Ser Glu Gly Gly
            35                  40                  45 ggc tct gag ggt ggc ggt tct gag ggt ggc ggc tct gag gga ggc ggt          372
Gly Ser Glu Gly Gly Gly Ser Glu Gly Gly Gly Ser Glu Gly Gly Gly
        50                  55                  60 tcc ggt ggt ggc tct ggt tcc ggt gat ttt gat tat gaa aag atg gca          420
Ser Gly Gly Gly Ser Gly Ser Gly Asp Phe Asp Tyr Glu Lys Met Ala
    65                  70                  75 aac gct aat aag ggg gct atg acc gaa aat gcc gat gaa aac gcg cta          468
Asn Ala Asn Lys Gly Ala Met Thr Glu Asn Ala Asp Glu Asn Ala Leu
80                  85                  90                  95 cag tct gac gct aaa ggc aaa ctt gat tct gtc gct act gat tac ggt          516
Gln Ser Asp Ala Lys Gly Lys Leu Asp Ser Val Ala Thr Asp Tyr Gly
                100                 105                 110 gct gct atc gat ggt ttc att ggt gac gtt tcc ggc ctt gct aat ggt          564

```
Ala Ala Ile Asp Gly Phe Ile Gly Asp Val Ser Gly Leu Ala Asn Gly
            115                 120                 125 aat ggt gct act ggt gat ttt gct ggc tct aat tcc caa atg gct caa      612
Asn Gly Ala Thr Gly Asp Phe Ala Gly Ser Asn Ser Gln Met Ala Gln
        130                 135                 140 gtc ggt gac ggt gat aat tca cct tta atg aat aat ttc cgt caa tat      660
Val Gly Asp Gly Asp Asn Ser Pro Leu Met Asn Asn Phe Arg Gln Tyr
145                 150                 155 tta cct tcc ctc cct caa tcg gtt gaa tgt cgc cct ttt gtc ttt agc      708
Leu Pro Ser Leu Pro Gln Ser Val Glu Cys Arg Pro Phe Val Phe Ser
160                 165                 170                 175 gct ggt aaa cca tat gaa ttt tct att gat tgt gac aaa ata aac tta      756
Ala Gly Lys Pro Tyr Glu Phe Ser Ile Asp Cys Asp Lys Ile Asn Leu
            180                 185                 190 ttc cgt ggt gtc ttt gcg ttt ctt tta tat gtt gcc acc ttt atg tat      804
Phe Arg Gly Val Phe Ala Phe Leu Leu Tyr Val Ala Thr Phe Met Tyr
        195                 200                 205 gta ttt tct acg ttt gct aac ata ctg cgt aat aag gag tct taa          849
Val Phe Ser Thr Phe Ala Asn Ile Leu Arg Asn Lys Glu Ser
                210                 215                 220
```

<210> SEQ ID NO 51
<211> LENGTH: 221
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

```
Thr Ser Gly Gln Ala Gly Gln Gly Gly Gly Ser Pro Phe Val Cys
  1               5                  10                  15

Glu Tyr Gln Gly Gln Ser Ser Asp Leu Pro Gln Pro Pro Val Asn Ala
             20                  25                  30

Gly Gly Gly Ser Gly Gly Gly Ser Gly Gly Gly Ser Glu Gly Gly Gly
         35                  40                  45

Ser Glu Gly Gly Ser Glu Gly Gly Gly Ser Glu Gly Gly Gly Ser
 50                  55                  60

Gly Gly Gly Ser Gly Ser Gly Asp Phe Asp Tyr Glu Lys Met Ala Asn
 65                  70                  75                  80

Ala Asn Lys Gly Ala Met Thr Glu Asn Ala Asp Glu Asn Ala Leu Gln
             85                  90                  95

Ser Asp Ala Lys Gly Lys Leu Asp Ser Val Ala Thr Asp Tyr Gly Ala
            100                 105                 110

Ala Ile Asp Gly Phe Ile Gly Asp Val Ser Gly Leu Ala Asn Gly Asn
        115                 120                 125

Gly Ala Thr Gly Asp Phe Ala Gly Ser Asn Ser Gln Met Ala Gln Val
    130                 135                 140

Gly Asp Gly Asp Asn Ser Pro Leu Met Asn Asn Phe Arg Gln Tyr Leu
145                 150                 155                 160

Pro Ser Leu Pro Gln Ser Val Glu Cys Arg Pro Phe Val Phe Ser Ala
                165                 170                 175

Gly Lys Pro Tyr Glu Phe Ser Ile Asp Cys Asp Lys Ile Asn Leu Phe
            180                 185                 190

Arg Gly Val Phe Ala Phe Leu Leu Tyr Val Ala Thr Phe Met Tyr Val
        195                 200                 205

Phe Ser Thr Phe Ala Asn Ile Leu Arg Asn Lys Glu Ser
    210                 215                 220
```

<210> SEQ ID NO 52
<211> LENGTH: 62
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Thr Ser Gly Gln Ala Gly Gln Gly Gly Gly Ser Ala Glu Gly Asp
1               5                   10                  15

Asp Pro Ala Lys Ala Ala Phe Asn Ser Leu Gln Ala Ser Ala Thr Glu
            20                  25                  30

Tyr Ile Gly Tyr Ala Trp Ala Met Val Val Ile Val Gly Ala Thr
        35                  40                  45

Ile Gly Ile Lys Leu Phe Lys Lys Phe Thr Ser Lys Ala Ser
    50                  55                  60

<210> SEQ ID NO 53
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Gly Gly Gly Gly Ser
1               5

<210> SEQ ID NO 54
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: This sequence may encompass 1 to 5
      "Gly-Gly-Gly-Gly-Ser" repeating units

<400> SEQUENCE: 54

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 55
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Tyr Pro Tyr Asp Val Pro Asp Tyr Ala
1               5

<210> SEQ ID NO 56
<211> LENGTH: 11
<212> TYPE: DNA
<213> ORGANISM: Artificial Sequence
<220> FEATURE:
<223> OTHER INFORMATION: Description of Artificial Sequence: Synthetic

```
                                        -continued
        oligonucleotide
<220> FEATURE:
<221> NAME/KEY: modified_base
<222> LOCATION: (4)..(8)
<223> OTHER INFORMATION: a, c, t, g, unknown or other

<400> SEQUENCE: 56
gccnnnnngg c                                                                    11
```

PHAGE DISPLAY TECHNOLOGIES

This application is a National Stage entry of International Application No. PCT/IB2006/001878, filed Jul. 6, 2006, the entire specification claims and drawings of which are incorporated herewith by reference.

FIELD OF THE INVENTION

The invention relates to improved phagemid vectors for generating phage display libraries.

BACKGROUND OF THE INVENTION

Phage display-based technologies provide means for cloning, expressing, selecting, and engineering polypeptides with biological functions mediated by their binding to another protein or any other biological target. The iterative process of the affinity-based selection allows the enrichment into relevant clones isolated from large libraries of protein sequences, such as antibodies, epitopes, antigens, bioactive peptides, enzyme inhibitors, enzymes, DNA-binding proteins, isolated protein domains, or ligands for receptors.

In combination with other techniques, phage display technologies, starting from sequences isolated from any kind of nucleic acid-containing material and leading to several types of products (antibodies, enzymes, peptides, etc.), can satisfy a large number of needs for modern biotechnology. Recently, several authors reported not only that functional protein sequences can be obtained using different phage display technologies but also that recombinant phage can be directly used for many applications (such as in diagnostics, for immunization, in proteomics, as antibacterial compounds, in cell transformation, for industrial biotechnology, in nanotechnologies, etc.).

Moreover, the construction of large repertoires of antibody fragments such as variable heavy/light chain heterodimers (or Fabs) and single chain variable regions (or scFv) expressed on the surface of recombinant phage, followed by the affinity-based selection of phage by "panning" on antigens, has been developed as a versatile and rapid method to obtain antibodies having the desired affinity and specificity. This selection process can be subsequently optimized by creating mutant antibody repertoires of the selected phage and sampled for descendents that, for example, bind to antigen under more stringent conditions and with greater affinity.

Phage display technologies take advantage of the small dimension and the adaptability of filamentous phage (such as M13, f1, or Fd), infecting bacterial cells (in particular F-pili bearing *Escherichia coli* cells) and having highly homologous, single stranded genomes. A large number of vectors, libraries, and display formats have been developed, as reviewed in many recent articles (Sidhu et al., 2000; Benhar, 2001; Sidhu, 2001; Szardenings, 2003; Bradbury and Marks, 2004; Hust and Dubel, 2004; Mancini et al., 2004; Pini et al., 2004; Conrad and Scheller, 2005; Hust and Dubel, 2005; Silacci et al., 2005; Smith et al., 2005), and in books ("Phage display: A practical Approach", vol. 266, ed. Clackson and Lowman H, Oxford Univ. Press, 2004; "Phage Display: A laboratory Manual", Burton D R et al., CSHL Press, 2001).

The protein sequences forming the surface of the filamentous phage (called coat proteins) can accommodate and display more or less efficiently heterologous protein sequences that are cloned on their N- or C-terminus forming fusion proteins. Different coat proteins (cp) have been used for this purpose, in particular the minor coat protein (also named as coat protein III/3, g3p, gIIIp, p3, pIII, cpIII, or cp3) and the major coat protein (also named as coat protein VIII/8, g8p, gVIIIp, p8, pVIII, cpVIII, or cp8), but also the other coat proteins cp6, cp7, and cp9 (Gao et al., 1999; Hufton et al., 1999; Kwasnikowski et al., 2005). Depending on the number of copies in which the modified phage protein is present, a distinction can be made between high valency (i.e. when the phage protein is present in a large number of copies, such as for cp8) and low valency (i.e. when the phage protein is present in a few number of copies, such as for cp3, cp6, cp7, or cp9) display, both approaches providing the possibility to select protein sequences binding a specific target.

The fusion of the coat protein with the protein to be displayed can be performed by using either a phage vector or a phagemid vector, providing libraries that can be screened using specific binding agents or targets (O'Connell et al., 2002). In both cases, a coat protein is modified in order to be transcribed and translated into a fusion protein that has a heterologous protein sequence cloned at its N-terminus and exposed by means of a secretion/leader sequence.

When using a phage vector, the DNA coding for the fusion protein is directly cloned into a coat protein of the phage genome, allowing high display levels but with a strong limitation in the size and in the cloning strategy of the heterologous sequence. Several variants to this system have been described, wherein combinations of modified and not modified variants of the same coat protein are present in the same phage vector. Such vectors are defined as type "88", "33", or "8+8" (Enshell-Seijffers et al., 2001; Petrenko and Smith, 2004).

When using a phagemid vector, the construct is smaller and comprises sequences triggering the replication during both bacterial and phage cell cycle but only expressing one (or few) of the coat proteins. The phagemid vectors are more easily manipulated by recombinant DNA technology in order to generate libraries of sequences to be expressed on the surface of phage. However, these vectors can provide the complete phage only when the transformed bacterial cells are later infected with a complete phage (the "helper" phage) that supports the correct replication and packaging of the phage, supplying the wild-type version of the coat proteins needed for the reinfection of recombinant phage and the consequent amplification.

Extensive studies have been made on the possibility to optimize the vectors and the sequences to be used for performing phage display screenings, identifying some constraints in using one coat protein rather another (Makowski, 1993) or differences in how heterologous protein sequences are actually displayed by different coat proteins (Iannolo et al., 1995; Weiss and Sidhu, 2000; Weiss et al., 2000; Roth et al., 2002; Li et al., 2003; Held and Sidhu, 2004).

For example, two or more protein sequences having distinct properties (e.g. one binding an antigen and another binding a ligand present on a solid substrate, or different epitope-binding peptides), were displayed on single bifunctional phage (also named in the literature as "dual display" or "double display" phage). Similar phage can be obtained by cloning each sequence in frame with a different coat protein (or a different variant of the same coat protein) into distinct transcription units in the same phagemid vector, assembled in mono- or bicistronic variants, or by double infecting bacterial cells with two phagemid vectors, each one for a specific fusion coat protein (Bonnycastle et al., 1997; Malik and Perham, 1997; Gao et al., 1999; Gao et al., 2002; Chen et al., 2004; WO 98/05344; WO 95/05454, WO 01/25416). While very efficient, the phage display technologies currently available still have room for improvement, and the choice of the coat protein for the display still remains an important issue.

In fact, the efficiency of the system can be substantially affected by the "fitness" of the protein sequence to be expressed, displayed, and screened using one rather than another specific coat protein sequence, a property that cannot be possible to determine in advance. For example, considering the coat proteins more frequently used for this purpose, cp8 seems more appropriate for selecting peptides or low affinity antibodies, due to the binding capacity enhanced by the multivalency of the cp8 system. In contrast, cp3-based display seems more appropriate for selecting high affinity antibodies, given the low number of copies in which the heterologous protein sequences are present on the phage surface. However, given that the affinity of the antibodies in a library is highly variable and impossible to foresee, other factors can affect the display system such as the proteolytic degradation of the cp3-/cp8-based fusion protein in the periplasmic space of E. coli or recombination events eliminating sequences included in the phagemid vector.

Similar problems, that are even more relevant when considering phage-displayed peptides, has been demonstrated in several articles, clearly indicating the need of constructing at least two distinct phage libraries, starting from the same sample containing the DNA coding for the antibody/peptide repertoire to be displayed, for a full exploitation of the potential of this technique. When looking at literature about the use of cp3 and cp8 for displaying and selecting protein sequences, different properties and/or sequences are reported for protein epitopes and peptides (Rousch et al., 1998; Zwick et al., 1998; Adda et al., 1999; Gao and Zhong, 1999; Yip et al., 2001; Al-bukhari et al., 2002; O'Connor K et al., 20051), antibodies (Kretzschmar and Geiser, 1995), or enzymes (Verhaert et al., 1999). Moreover, mixing two phage libraries, each one generated separately with a different phagemid (Jacobsson et al., 2003), or recloning sequences selected using one coat protein into a library displaying another coat protein (Wang et al., 1997) have also been described. Functional protein sequences were also identified using phage displayed libraries wherein random sequences are cloned without a specific orientation, but are actually transcribed and translated directionally by means of regulatory and coding sequences positioned in 5' and 3' region to the cloning site, within the vector backbone (Zelenetz and Levy, 1990; van Zonneveld et al., 1995; Stratmann and Kang, 2005).

Several patent applications disclose variants of the phage display technology, such as the combined use of cpVII and cpIX (WO 00/71964), the addition of restriction sites into phage vectors (WO 03/093471, WO 03/91425), the use of bidirectional promoters with heavy and light chain sequences positioned head to head in opposite transcriptional orientations (Den et al., 1999), different combinations encoding sequences arranged for mono- or bi-cistronic expression (Kirsch et al., 2005), the introduction of mutations into coat proteins (WO 02/103012; WO 00/06717), or different approaches for library construction, expression, and screening (WO 98/20036; WO 98/14277; WO 97/35196; WO 97/46251; WO 97/47314; WO 97/09446; WO 03/029456). Alternatively, many documents describe cloning systems based on site-specific recombination for assembling protein sequences into phagemids (WO92/20791, WO95/021914, WO97/020923, WO00/31246, WO96/40714; Tsurushita et al., 1996; Sblattero and Bradbury, 2000).

However, none of these documents discloses how to generate, starting from a library of DNA coding for heterologous proteins and a single phagemid, a single phage library allowing the display of the heterologous proteins fused to either one or the other of two coat proteins.

SUMMARY OF THE INVENTION

The present invention provides means for cloning, producing, and screening amino acid sequences as proteins fused with either one of two coat protein on the surface of filamentous phage, using a single phagemid vector and a single cloning and transformation step.

In a first embodiment, the present invention provides phagemid vectors for the bidirectional cloning of a DNA coding for an amino acid sequence to be fused at the N-terminus of either one or the other of two functional coat proteins.

In a second embodiment, the present invention provides phagemid vectors comprising:

a) A DNA coding for a first functional coat protein comprising a first DNA linker at its 5' end; and b) A DNA coding for a second functional coat protein, having the direction of transcription opposite to that of the first functional coat protein, and comprising a second DNA linker at its 5' end;

wherein the first and second DNA linker comprise at least one identical site for a restriction enzyme not present outside said linker in the phagemid vector.

Examples of such phagemids, generically defined as pDD (phagemid for Double Display), are those comprising two separate DNA linkers, also called DIS linkers, each having adjacent SpeI-BglI restriction sites (SEQ ID NO.: 1) at their 5' end, that can be followed by the DNA sequence coding for a protein linker forming a DIS Linker2 (SEQ ID NO.: 2 and SEQ ID NO.: 3). Alternatively, the SpeI-BglI restriction sites can be combined in a single sequence (SEQ ID NO.: 4) that, with the addition of two distinct DNA sequences, each coding for a protein linker downstream and upstream on the two strands, can form a DD-DIS Linker2 (SEQ ID NO.: 5). The DNA linker can be transcribed in frame with the 5' end of the DNA coding for a functional coat protein, and with the 3' end of the DNA coding for a protein sequence to be fused to and displayed by said functional coat protein.

In a third embodiment, the present invention provides phagemid vectors comprising a Double Display expression cassette (DD cassette). Such a vector further comprise a DNA cassette for the cloning, the expression, and the display of at least one protein sequence to be fused at the N-terminus of either one or the other of said functional coat proteins by means of one of said DNA linker.

After being cloned within a pDD vector, the DD cassette becomes operatively linked to either one or the other of the two functional coat proteins, depending on the orientation in which the DD cassette is cloned, and allowing its transcription and translation into a fusion protein comprising a heterologous sequence at its N-terminus by means of the sequences present within the DD cassette.

Similar phagemids are provided by means of pDD vectors comprising the DNA coding for the two functional coat proteins called modified cp3 (cp3*, SEQ ID NO.: 6) and modified cp8 (cp8*, SEQ ID NO.: 8). Examples of such vectors are those comprising cp3*DDcp8* (SEQ ID NO.: 10), DDa cassette (SEQ ID NO.: 11), or DDb cassette (SEQ ID NO.: 12).

The DD cassette can include one or more additional genes, for example, coding for a selection marker gene, a gene altering bacterial metabolism, or a protein sequence interacting with the heterologous protein sequence fused at the N-terminus of either one or the other of two functional coat proteins. Such additional genes are transcribed and translated independently from the orientation in which the DD cassette is inserted and can be oriented in any direction.

In a fourth embodiment, the present invention provides the use of the vector defined above for generating a phage or a cell library, wherein each protein sequence of said library is fused at the N-terminus of either one or the other of two functional coat proteins by means of a DIS linker.

In a fifth embodiment, the present invention provides phage or cell libraries obtained using the vectors defined above, wherein each protein sequence of said library is fused at the N-terminus of either one or the other of two functional coat proteins by means of a DIS linker.

Examples of two functional coat proteins are modified cp3 protein (cp3* protein; SEQ ID NO.: 7) and modified cp8 protein (cp8* protein; SEQ ID NO.: 9).

The libraries can be generated using a DD cassette that can be cloned in any type of vector, or that is already cloned in a pDD vector. In latter case, the library constructed in the DD cassette should be subjected to the digestion with a restriction enzyme cutting within the DIS linker and to the ligation with a pDD vector cut with an enzyme providing compatible ends in order to obtain the bidirectional cloning of the DD cassette.

The library of pDD vectors can be then maintained into the bacterial cells, since the phagemids in the cell library can be replicated using the bacterial origin for replication. Alternatively, the library can be replicated as a phage library, by infecting such bacterial cells with helper phage, and purified in the form of the recombinant phage containing the phagemids and expressing the heterologous protein sequences on their surface, being fused at the N-terminus of either one or the other of two functional coat proteins by means of a DIS linker.

In a sixth embodiment, the present invention provides kits for generating a phage or a cell library wherein each protein sequence of said library is fused at the N-terminus of either one or the other of two functional coat proteins by means of a DIS linker, comprising a vector defined above.

In a seventh embodiment, the present invention provides methods for producing a phage or a cell library wherein each protein sequence of said library is fused at the N-terminus of either one or the other of two functional coat proteins by means of a DIS linker, comprising:

a) inserting a DD cassette in correspondence to the DIS linkers of a phagemid vector for the bidirectional cloning of a DNA coding for an amino acid sequence to be fused at the N-terminus of either one or the other of two functional coat proteins; and b) transforming the cells with the resulting vectors.

The insertion of said DD cassette can be obtained by ligating a DD cassette and a vector that have been digested with BglI and have compatible ends.

Recombinant phage, as well as fusion proteins, obtained by the methods of the invention can be used, in isolated forms or in the form of mixtures, for binding, detecting, neutralizing, and/or altering a ligand, a cell, or a target molecule. This activity of the recombinant phage, or of the fusion proteins, can be detected in vivo and/or in vitro.

In all the embodiments, the heterologous protein sequence that is fused at the N-terminus of either one or the other of two functional coat proteins by means of a DIS linker can be an antibody, an antibody fragment, an epitope, an epitope-binding region, an antigen, an allergen, a bioactive peptide, an enzyme, an enzyme inhibitor, an enzymatic catalytic site, a DNA-binding protein, an isolated protein domain, a ligand for receptors, a receptor, a growth factor, a cytokine, and contiguous or overlapping fragments of a protein sequence of interest.

Further embodiments of the present invention, including isolated recombinant DNA and protein sequences as well as other methods and uses, will be provided in the following description.

DESCRIPTION OF THE FIGURES

FIG. 1: Alignment of the DNA and protein sequence of cp3* DNA (SEQ ID NO.: 6) and protein (SEQ ID NO.: 7). At the 5' end, the DIS linker2 (underlined; SEQ ID NO.: 2 and SEQ ID NO.: 3), including the restriction sites SpeI and SfiI (boxed; SEQ ID NO.: 1) and the sequence coding for the Gly4Ser linker (SEQ ID NO: 53) (for a total of 12 amino acids), is fused in frame with the 5' of the DNA fragment encoding amino acids 216-424 of the coat protein cp3 of *Enterobacteria phage* M13 (protein sequence SWISSPROT Acc. No. P69168; nucleotide sequence GENBANK Acc. No, NC_003287, fragment 2224-2853 including the original stop codon). At the 3' end, a NheI site (boxed) is added by the PCR just after the stop codon (underlined). The nucleotide $A_{523}$ to $G_{523}$ substitution (leading to the $Ser_{175}$ to $Gly_{175}$ substitution) is also boxed.

FIG. 2: Agarose gel electrophoresis showing the cp3* DNA amplification product obtained by using the primers cp3*FW (SEQ ID NO.: 13) and cp3*RW (SEQ ID NO.: 14), and appearing as a band of approximately 680 bp.

FIG. 3: (A) Sequence of the HA tag linker resulting from the annealing of the oligonucleotides HA tag linker FW (SEQ ID NO.: 17) and HA tag linker RW (SEQ ID NO.: 18). The single stranded 5' ends, one compatible with XhoI (CTCGAG) and the other with SpeI (ACTAGT) restriction sites, are underlined. (B) Alignment of the DNA and protein sequence of HAcp3* DNA (SEQ ID NO.: 19) and protein (SEQ ID NO.: 20) sequence. The 221 amino acid cp3* sequence results fused to the PelB leader sequence (SEQ ID NO.: 25) and the HA tag, generating a 258 amino acid protein sequence.

FIG. 4: Schematic representation of the phagemid vectors pRIB1-cp3* (A), pRIB1-HAcp3* (B), and pRIB1-e44 cp3* (C) comprising two LacZ promoter (LacZp) that are operatively linked to PelB leader/secretion sequence. The LacZP-PelB segment is fused in frame with cp3* only (in A), with cp3* further containing HA tag (HA, in B) or e44 heavy chain (e44HC, in C) sequences, or with e44 light chain (e44LC, in C). Other relevant elements, such as ampicillin (Amp') and chloramphenicol resistance (CAT) genes, as well as the cloning sites and replication origins, are indicated.

FIG. 5: Western blots on total cell extracts from *E. Coli* XL1Blue transformed with pRIB1 series of vectors. (A) Expression of HA tag detected using anti-HA tag antibodies in bacterial cells transformed with pRIB1-cp3* (negative control) or pRIB1-HAcp3*. (B) Expression of e44 Fab detected using anti-human Fab antibodies in bacterial cells transformed with pRIB1-e44 cp3 (positive control) or pRIB1-e44 cp3*. The band of e44 heavy chain is slightly higher due to the addition of sequence encoded by the DIS linker2. The amount of light chains is higher since the expression of this protein is not limited by the dimension of the coat protein fused to the heavy chain.

FIG. 7: Alignment of the DNA and protein sequence of HAcp8* (SEQ ID NO.: 21 and SEQ ID NO.: 22). The 62 amino acid cp8* sequence results fused to the PelB leader sequence (SEQ ID NO.: 25) and the HA tag, generating a 99 amino acid protein sequence.

FIG. 8: Western blots on total cell extracts from *E. Coli* XL1Blue transformed with pRIB2 series of vectors. (A) Expression of HA tag detected using anti-HA tag antibodies in bacterial cells not transformed (negative control) or transformed with pRIB2-HAcp8* (the HAcp8* in the mature and in the immature forms can be distinguished). (B) Expression of e44 Fab detected using anti-human Fab antibodies in bacterial cells not transformed (negative control) or transformed with pRIB2-e44 cp8*.

FIG. 9: Production of recombinant phage displaying DIS linker2-modified coat proteins, comparing the colony-forming unit (cfu) per microliter measured for phage expressing normal cp3 (positive control; using pRIB-cp3) or cp3*, as such (using pRIB1-cp3*; A), fused to HA tag (using pRIB-HAcp3 and using pRIB1-HAcp3*; B), or fused to e44 Fab (using pRIB-e44 cp3 and using pRIB1-e44 cp3*; C).

FIG. 10: Production of recombinant phage displaying DIS linker2-containing coat proteins, comparing the colony-forming unit (cfu) per microliter measured for phage expressing the positive controls, normal cp3 as such (using pRIB-cp3) or fused to e44 fab (using pRIB-e44 cp3) compared to those expressing e44 cp8* (using pRIB2-e44 cp8*; A), cp8* (using pRIB2-cp8*; B), or HAcp8* (using pRIB2-HAcp8*; C).

FIG. 11: Panning experiments using recombinant phage expressing HA-cp3* (using pRIB1-HAcp3*; A) or HA-cp8* (using pRIB2-HAcp8*; B) against bovine serum albumin (BSA), anti-HA tag antibody (anti-HA), or Hepatitis C virus E2 protein (E2) as binding agent. The Y axis shows the value of phage that are eluted at the end of the procedure to the binding agent (OUTPUT phage, calculated according to formula III in the text, in cfu/µl).

FIG. 12: Panning experiments using recombinant phage expressing e44-cp3 or e44-cp3* (using pRIB2-e44 cp3*; A) and e44-cp8* (using pRIB2-e44 cp8*; B) against bovine serum albumin (BSA), or Hepatitis C virus E2 protein (E2) as binding agent. The Y axis shows the value of phage that are eluted at the end of the procedure to the binding agent (OUTPUT phage, calculated according to formula III in the text, in cfu/µl)

FIG. 14: Schematic representations of the DD cassettes and of their elements (not in scale). (A) basic features and arrangement of DNA elements, including generic single sites for restriction enzymes (SREs) or single sites for restriction enzymes specific for the DIS linker (DIS-SREs) in a DD cassette; (B) features and arrangement of DNA elements, BglI and SpeI sites, SREs, and a marker gene in a DD cassette for expressing a single peptide or functional protein as a fusion protein with a functional coat protein. (C) Features and arrangement of DNA elements, BglI and SpeI sites, SREs, and of a marker gene in a DD cassette for expressing a Fab wherein the variable region of an heavy chain is expressed as a fusion protein with a functional coat protein and the variable region of a light chain is expressed by a separate gene within the same DD cassette. (D) Features and arrangement of DNA elements, BglI and SpeI sites, SREs, and of a marker gene in a DD cassette for expressing a two sequence in with a single transcript wherein the one starting after the Ribosome Binding Site (RBS) is expressed as a fusion protein with a functional coat. The respective position and number of marker or other genes not expressed as a fusion protein with a functional coat protein, as well as position and number of SREs, are purely exemplary and can be adapted to the specific use of the DD cassette. The arrow on the top of each schematic representation indicates the direction of transcription pointing from the DD cassette to the backbone of the vector and, in the case the DD cassette is cloned in a pDD vector, where is present the functional coat protein that is fused by means of the DIS linker.

FIG. 16: sequence of cp3*DDcp8* (SEQ ID NO.: 10), presenting a DD-DIS linker2 (SEQ ID NO.: 4) including the sequence formed by the double BglI site and the single SpeI site (SEQ ID NO.: 4) that is linked with the DNA sequence encoding cp3* (SEQ ID NO: 50) (in 5' to the DD-DIS linker2; the corresponding protein sequence (SEQ ID NO: 51) is shown below the antisense strand) and the DNA sequence encoding cp8* (SEQ ID NO: 10) (in 3' to the DD-DIS linker2; the corresponding protein sequence (SEQ ID NO: 52) is shown on the sense strand). This sequence is comprised in the pDD-cp3*cp8* of FIGS. 14 and 15.

FIG. 17: sequence of an exemplary DD cassette (DDa cassette; SEQ ID NO.: 11) compatible with a pDD vector, such as the ones designed in FIG. 15 or with pDD-cp3*cp8*, with the relevant restriction sites, the two distinct LacZ promoters (LacZp) and PelB starting codon for the sequence to be cloned between ScaI and XbaI (that is expressed constitutively in the DD cassette) and for the sequence to be cloned between XhoI and SpeI (that is expressed constitutive in the DD cassette when the DD cassette is fused to a functional coat protein by means of a DIS linker), the chloramphenicol resistance gene (CAT) start and stop codons, and the HA tag that is used as stuffer DNA between PelB sequence and DIS linker. The CAT gene can be also cloned in the opposite direction.

FIG. 18: sequence of an exemplary DD cassette (DDb cassette; SEQ ID NO.: 12) compatible with a pDD vector, such as the ones designed in FIG. 15 or pDD-cp3*cp8*, with the relevant restriction sites, the two distinct LacZ promoters (LacZp) and PelB starting codons for the sequence to be cloned between ScaI and XbaI (that is expressed constitutively in the DD cassette) and for the sequence to be cloned between XhoI and SpeI (that is expressed constitutive in the DD cassette when the DD cassette is fused to a functional coat protein by means of a DIS linker), the Zeocin resistance gene (ZEO) start and stop codons, and the HA tag that is used as stuffer DNA between PelB sequence and DIS linker. The ZEO gene can be also cloned in the opposite direction.

FIG. 20: Panning experiments using recombinant phage displaying HA peptide (panel A) or e44 fab (panel B) fused to cp3* or cp8* and panned using anti-HA peptide antibody (anti-HA; panel A) or Hepatitis C virus E2 recombinant protein (E2; panel B) as binding agent. In both cases bovine serum albumin (BSA) was used as negative binding agent. The peptide and fab were expressed using a pDD-cp3*cp8* phagemid including a DD cassette expressing CAF gene, and either pRIB1-based vectors (for cp3* positive control) or pRIB2-based vectors (for cp8* positive control). The pRIB vector, expressing cp3 alone, is provided as negative control. The Y axis shows the value of phage that are eluted at the end of the procedure to the binding agent (OUTPUT phage, calculated according to formula III in the text).

FIG. 21: Panning experiments using recombinant phage displaying HA peptide (panel A) or e44 fab (panel B) fused to cp3* or cp8* and panned using anti-HA peptide antibody (anti-HA; panel A) or Hepatitis C virus E2 recombinant protein (E2; panel B) as binding agent. In both cases bovine serum albumin (BSA) was used as negative binding agent. The peptide and fab were expressed using a pDD-cp3*cp8* phagemid including a DD cassette expressing either CAF or ZEO as selection marker. pRIB1-based vectors (for cp3* positive control) or pRIB2-based vectors (for cp8* positive control) were also used. The Y axis shows the value of phage that are eluted at the end of the procedure to the binding agent (OUTPUT phage, calculated according to formula III in the text).

FIG. 22: Restriction (A) and Western blot (B) analysis of clones randomly chosen from a pDDb-based *E. coli* library. The number identifying each clone is indicated on the top of (A) and it has been maintained in (B). The clones having the same restriction pattern (see FIG. 19) were put aside to each other when preparing the Western blot.

DETAILED DESCRIPTION OF THE INVENTION

Figure 6:
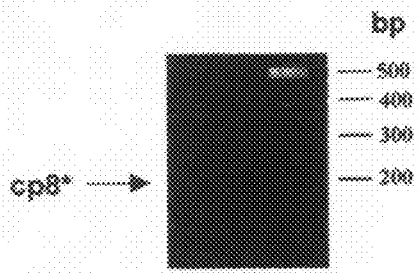
FIG. 6: (A) Alignment of the DNA and protein sequence of cp8* (SEQ ID NO.: 8 and SEQ ID NO.: 9). At the 5' end, the DIS linker2 (underlined; SEQ ID NO.: 2 and SEQ ID NO.: 3), including the restriction sites SpeI and SfiI (boxed; SEQ ID NO.: 1) and the sequence coding for the Gly4Ser linker (SEQ ID NO: 53) (for a total of 12 amino acids) is fused in frame with the 5' of the DNA fragment encoding amino acids 24-73 of the coat protein cp8 of *Enterobacteria phage* (protein sequence SWISSPROT Acc. No. P69541; nucleotide sequence GENBANK Acc. No, NC_003287, fragment 1370-1522 including the original stop codon). At the 3' end, a NheI site is added by the PCR just after the stop codon (underlined). (B) Agarose gel electrophoresis showing the cp8* DNA amplification product obtained by using the primers cp8*FW (SEQ ID NO.: 15) and cp8*RW (SEQ ID NO.: 16), and appearing as a band of approximately 200 bp.

The technical problem underlying the present invention is how to establish a simple and efficient system which enables the expression of an amino acid sequence to be expressed and displayed as a fusion protein with either one of two alternative phage coat proteins in a filamentous phage, without cloning this sequence twice, either in a single or in two phagemid vectors, and/or without infecting bacterial cells twice.

The solution to this technical problem is achieved by constructing phagemid vectors that allow for the bidirectional cloning of a DNA coding for an amino acid sequence to be fused at the N-terminus of either one or the other of two functional coat proteins of recombinant phage.

The basic elements of this vector, generically defined as pDD (phagemid for Double Display) are:

a) A DNA coding for a first functional coat protein comprising a first DNA linker at its 5' end; and b) A DNA coding for a second functional coat protein, having the direction of transcription opposite to that of the first functional coat protein, and comprising a second DNA linker at its 5' end;

wherein the first and second DNA linker comprise at least one identical site for a restriction enzyme not present outside said linker in the phagemid vector.

Specific DNA linker sequences to be included in the vectors of the Invention are hereafter indicated as "DIS linkers" (Display and Insertion Site linkers). The identical site for a restriction enzyme is intended for making the 5' ends of the functional coat proteins compatible to each other, or to the insertion of a DNA fragment having the same site at its extremities, when digested with such enzyme and exposed to a simple ligation reaction (due to the blunt or single stranded, complementary 3'/5' ends).

Moreover, the DIS linker should be designed in a way that it can be transcribed in frame with the 5' end of the DNA coding for a functional coat protein, and with the 3' end of the DNA coding for a protein sequence to be fused to and displayed by said functional coat protein. Thus, the functional coat protein and the protein sequence to be displayed are consequently separated by a protein linker encoded by the DIS linker. This protein linker should not qualitatively alter (e.g. by virtue of its length or of its affinity for a ligand) the properties of both the functional coat protein and of the protein sequence to be displayed.

Similar linkers have been disclosed for phagemid vectors in the literature and can be adapted to the requirement of the invention regarding the restriction site type and position. The examples (FIGS. 1 and 6) show a DIS linker including two restriction sites (SEQ ID NO.: 1) that can be combined with an additional sequence encoding a Gly4Ser linker (SEQ ID NO: 53), the forming DIS linker2 (SEQ ID NO.: 2 and SEQ ID NO.: 3). Particularly preferred linkers are those providing a high degree of mobility to the fusion protein at the point of the linker. An exemplary and preferred linker has the formula $(Gly4Ser)_n$, where n is 1-5 (SEQ ID NO: 54). Linkers adapted to Fab or Scfv have been identified in the literature (Hennecke et al., 1998). The two DIS linkers in the phagemid vectors can be simply compatible (i.e. having one or more identical restriction sites) or identical (i.e. having also identical linker sequence, as in the examples).

The arrangement of DNA sequences coding for the DIS linker and functional coat protein sequences can be achieved according to different criteria and situations presented in the examples and in the figures. The phagemids of the invention can contain two DIS linkers separated by a DNA sequence having variable length and features, but the two DIS linkers can be also directly linked to each other by means of the common restriction site, as shown for DD-DIS linker2 (FIG. 16; SEQ ID NO.: 4: and SEQ ID NO.: 5).

Coat proteins modified with adaptor/linker sequences, including restriction sites similar to those defining the DIS linker, have been disclosed in the prior art (WO 04/078937, WO 03/091425, WO 02/088315, WO 99/29888). However, none of these documents discloses the combination and the physical arrangement of two DIS linkers into a phagemid vector in order to obtain the bidirectional cloning of a protein sequence fused to either one or the other of two functional coat proteins.

Moreover, the presence of the DIS linkers and of the corresponding functional coat proteins cloned in opposite orientation (that is, being each transcribed from a different strand) in a vector allow the construction of phagemid vectors further comprising a DNA cassette for the cloning, the expression, and the display of at least one protein sequence to be fused at the N-terminus of either one or the other of said functional coat proteins by means of one of said DIS linker.

The specific DNA cassette allowing the cloning, the expression, and the display of at least one protein sequence to be fused at the N-terminus of either one or the other of said functional coat proteins by means of one of said DIS linker is hereafter indicated as Double Display expression cassette (DD cassette). Different forms in which a DD cassette can be generated are presented in FIG. 14.

After being cloned within a pDD vector by means of the restriction site common to the DIS linkers present within the vector, the DD cassette becomes operatively linked to either one or the other of the two functional coat proteins, depending on the orientation in which the DD cassette is cloned, allowing its transcription and translation into a fusion protein comprising a heterologous sequence at its N-terminus by means of the sequences present within the DD cassette and of the DIS linker.

Figure 15:
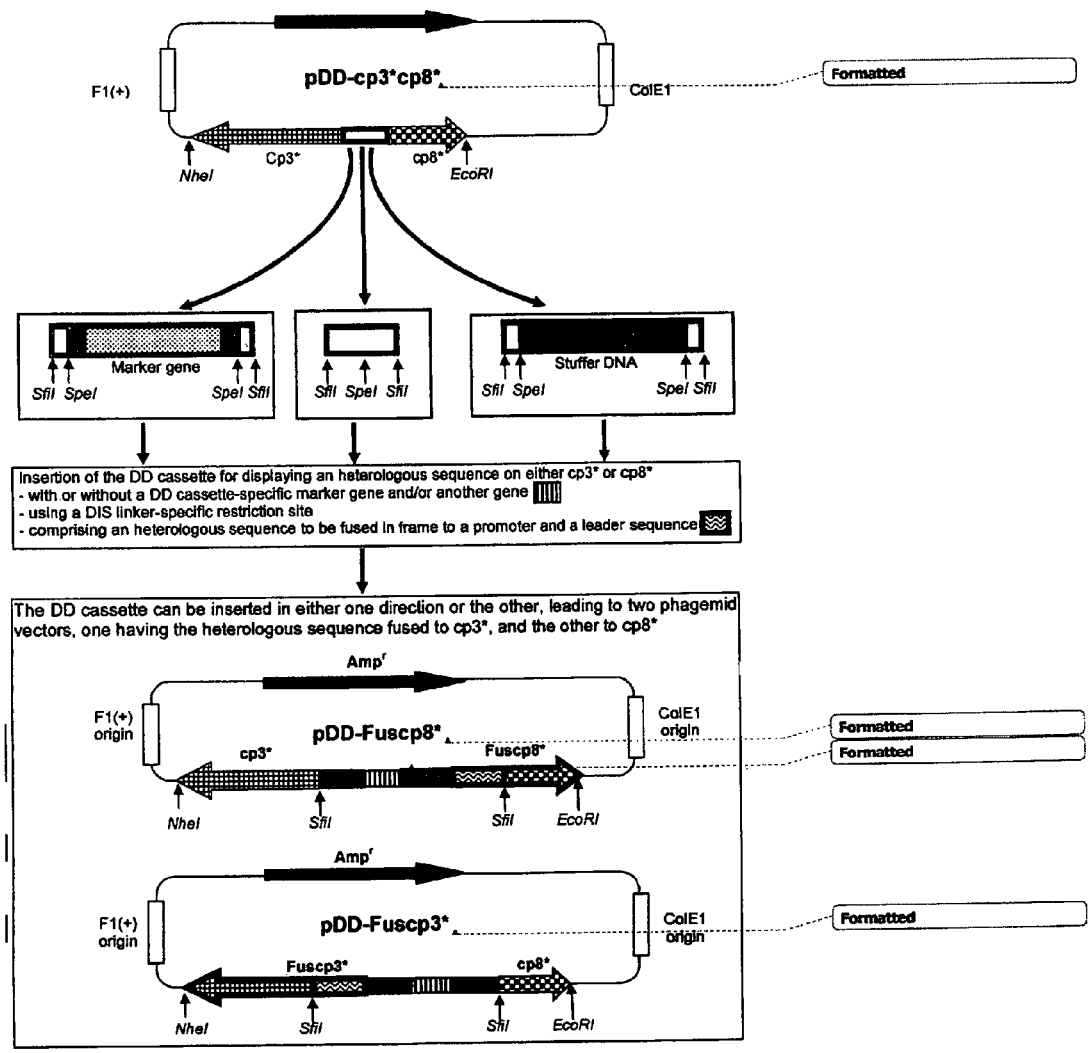
FIG. 15: Structure of the prototype of phagemid vector of the invention including cp3* and cp8* (pDD-cp3*cp8*), that can include different of sequences when empty (e.g., a simple DD-DIS linker, stuffer DNA, or a marker gene). Whatever empty vector is used, the insertion of the DD cassette provides two forms of the pDD vector, one containing the gene for displaying the fusion protein with cp8* (pDD-Fuscp8*) and the other the gene for displaying the fusion protein with cp3* (pDD-Fuscp3*). These recombinant genes are indicated with the thicker line.

In fact, each DNA segments coding for a functional coat protein, being assembled in a pDD vector with divergent sense of transcription but without a proper promoter, requires the correct insertion of a promoter (and of a starting ATG-containing protein sequence to be fused at the 5' end, if missing) in order to be transcribed and translated, that can be provided by a DD cassette. Given the two opposite orientations in which the DD cassette can be inserted, this will be achieved for only one of the functional coat protein in each pDD vector containing a DD cassette (FIG. 15).

Statistically, there are equal chances that the DD cassette is inserted in one sense or the other, and at the same time there are several copies of each DD cassette available in the ligation mixture. Therefore, it is expected that a library constructed with a pDD vector and several DNA fragments based on the same DD cassette (and different for the heterologous protein sequence that is cloned within) will contain at least a pair of pDD vectors having each DD cassette that is cloned in one or the other orientation. Thus, the population of cells recombinant phage that form a library constructed according to the methods of the invention potentially represents a repertoire of heterologous protein sequences in two formats (that is, fused to one or the other functional coat protein).

A "functional coat protein" should be intended as an entire, or a portion of, coat protein of a filamentous phage that is capable of being inserted in the coat of the phage and of displaying a heterologous sequence fused at its N-terminus on the surface of said phage. The coat protein can be one of those encoded by any filamentous phage (e.g., M13, fl, and fd), including cp3, cp7, cp8, or cp9.

As shown in the examples with the DNA coding for the two functional coat proteins called modified cp3 (cp3*, SEQ ID NO.: 6 and SEQ ID NO.: 7) and modified cp8 (cp8*, SEQ ID NO.: 8 and SEQ ID NO.: 9), both first and second sequences of the functional coat proteins cloned in the phagemids of the invention do not contain the sequences necessary for their correct expression at their 5' end (FIGS. 1 and 6). Only after the insertion of a heterologous sequence to be displayed, together with the appropriate regulatory sequences, either the first or the second functional coat protein is actually transcribed and translated into a fusion protein displaying such heterologous sequence.

The examples also show that the DNA coding for cp3* and cp8* can be directly cloned in the opposite orientation and linked to each other by means of a common restriction site, forming a DD-DIS linker2 that is comprised in the resulting sequence called cp3*DDcp8* (FIG. 16; SEQ ID NO.: 10).

Natural, functional variants of these proteins are known, and specific variants of the natural coat proteins active as functional coat proteins are disclosed in the examples. A large number of non-natural coat protein variants has also been expressed and tested for their properties in displaying heterologous protein sequences (Iannolo et al., 1995; Gao C et al., 1999; Petrenko et al., 2002; Weiss et al., 2003; Weiss and Sidhu, 2000; Held and Sidhu, 2004; Kwasnikowski et al., 2005). Any of these alternative non-natural and natural variants of coat protein sequences allowing the display of the protein fused at their N-terminus can be used in the vectors of the invention as functional coat proteins.

Moreover, the functional coat protein may also contain one or more short heterologous sequences (commonly referred to as "tag" sequences) that should be located in a position not affecting the correct expression and display activities. These variants of the functional coat proteins comprise one of the amino acid sequences as defined above and an amino acid sequence that provides additional properties without impairing significantly the protein display activity. Examples of such additional properties provide for an easier detection procedure, an additional binding moiety, or the post-translational modification of the fusion protein (e.g. phosphorylation, endoproteolytic digestion).

Design of the moieties, ligands, and linkers, as well as methods and strategies for the construction, purification, detection and use of fusion proteins are widely discussed in the literature (Nilsson et al., 1997; "Applications of chimeric genes and hybrid proteins" Methods Enzymol. Vol. 326-328, Academic Press, 2000; WO 01/77137).

Such additional protein sequences can be positioned in the phagemid vector within the DIS linker, within one or both functional coat proteins, or between the DIS linker and the N-terminal region of one or both functional coat proteins. Moreover, this additional sequence can be positioned in correspondence of only one or both functional coat protein sequences present in the phagemid of the invention, or it can be different from one to the other coat protein. This approach can help the detection and the isolation of all the phage in the libraries generated according to the methods of the invention in which the functional display cassette (the Double Display expression cassette, or DD cassette) has been inserted in a way that the heterologous protein sequence is fused to a specific functional coat proteins.

Therefore, it is of particular interest to include sequences such as polyhistidine, FLAG, c-Myc, HA tag, proteolytic sites, or any other short tag sequences that can be detected or immobilized by means of specific substrates, enzymes, or antibodies. Different tags (single or in a precise combination) can be present in the phagemid vector, helping the in vivo and/or in vitro identification of the fusion protein, or its purification. Various tag sequences have been tested for different coat proteins (Nakashima et al., 2000). The tag can also allow aqueous two-phase partitioning (Bandmann et al., 2002) or fluorescence-mediated detection (Morino et al., 2001). Similar additional sequences may act as tether between the coat protein and the heterologous sequence to be displayed, as shown for proline-rich tethers that are capable of improving the display on the coat protein (Nakayama et al., 1996).

The term "heterologous protein sequence" indicates that the sequence does not naturally occur as an amino acid or nucleotide sequence of a respective naturally occurring filamentous phage. In the context of a fusion protein, a heterologous sequence does not occur in the same polypeptide sequence as a respective natural polypeptide. The protein sequence under consideration comprises typically at least 5 amino acids.

A "first" and a "second" functional coat proteins should be intended as two different sequences of functional coat proteins, as shown in the examples with modified cp3 protein (cp3* protein; SEQ ID NO.: 7) and modified cp8 protein (cp8* protein, SEQ ID NO.:9). They should be derived from the same or a different phage, and each should correspond to a different coat protein known to be able to display heterologous sequences on the surface of said phage, or the same coat protein modified at the level of sequence in two different manners (e.g. a short and a long version, a natural and a mutated version, a tagged and a non-tagged version, two differently tagged sequences, etc.).

The DNAs encoding the two functional coat proteins physically divide the phagemid vector pDD in two parts (see FIG. 15):

a) the backbone, that is the region comprised between the 3' ends of DNA coding for each of the two functional coat proteins and containing the minimal elements necessary for replication in bacteria and phage, and possibly additional genes such as a first gene for a selection marker;

b) the region comprised between the 5' ends of the DIS linkers at the 5' end of each DNA coding for a functional coat protein, where the DD cassette is cloned or can be cloned by means of DIS linkers.

The literature provides many examples of the minimal elements necessary for replication in bacteria and phage, such as the ColE1 ad the f1(+) origin included in the vectors described in the examples.

The content of the display cassette is determined by the sequence cloned within the restriction sites present in said DIS linkers. When the phagemid vector is devoid of any sequence to be displayed (an "empty" vector), the display cassette can be (FIG. 15):

a) simply absent, being the two DIS sites fused in a single one by virtue of compatible ends of the common restriction sites;

b) consisting of a non-essential, non-coding DNA sequence (commonly referred to as a "stuffer" sequence);

c) comprising the gene for a second selection marker gene (different from the one comprised in the backbone), which is separated from the two DIS linkers by two stuffer DNA sequence positioned at its 5' and 3' ends.

A "selection marker gene" should be intended as a gene that encodes a protein allowing the positive or negative selection of the cell expressing said gene. In the context of the present invention, the gene can encode, for example, a protein allowing the resistance of the bacterial cell transformed with the phagemid vector to an antibiotic, helping the maintenance of the vector. The choice of the specific selection marker for each element of the system (i.e. the backbone, the display cassette, and the double display expression cassette) gives the opportunity to apply appropriate selection criteria for isolating bacteria containing the desired phagemid vector. Typical bacterial drug resistance genes are those that confer resistance to ampicillin, tetracycline, neomycin/kanamycin, zeocin, or cholamphenicol.

A first DNA sequence "operatively linked" to a second DNA sequence should be intended that the two DNA sequences are joined in a way that first DNA sequence (usually, comprising a non-/regulatable promoter or another transcriptional regulatory site) allows, or modifies to some measurable extent, the transcription of the second DNA sequence (e.g. a complete or partially complete open reading frame of a gene). The presence of a promoter sequence operatively linked to a signal sequence and pointing to a specific end of the DD cassette makes the transcription directional from the cassette into the pDD backbone, determining the functional asymmetry of the DD cassette compared to the symmetry of the elements allowing the insertion of the DD cassette.

The use of the pDD vector for displaying heterologous protein sequences is allowed by the substitution of the display cassette in the "empty" vector with an appropriate DD cassette generated by cloning and/or PCR procedures.

A "double display expression cassette" (DD cassette) should be intended as a linear DNA fragment having 5' and 3' ends compatible with a restriction site present in the DIS linkers of the phagemid vector (and generally absent from the rest of said cassette), further comprising at least an inducible or constitutive promoter region operatively linked to a starting ATG-containing, leader sequence, located at one of two ends of the linear fragment and encoding the protein sequence to be displayed at the N-terminus of one or the other functional coat proteins present in the backbone.

As shown in FIG. 14, the DD cassette is formed by the asymmetric juxtaposition of DNA segments having different function, usually separated by one or more sites for restriction enzymes. This asymmetric arrangement is responsible of the specific direction in which the transcription is started from the cassette in direction to the backbone of the vector. When the DD cassette is cloned in a pDD vector, this transcription allows the fusion of DNA encoding the sequence to be displayed to the DNA encoding the functional coat protein in the pDD vector by means of a DIS linker.

Two DD cassettes for expressing peptides and proteins under the control of a LacZ promoter and a PelB signal sequence are provided in the examples under the name of DDa cassette (FIG. 17; SEQ ID NO.: 11) and DDb cassette (FIG. 18; SEQ ID NO.: 12). The specific cassettes differ essentially on the type of marker gene allowing the selection of vectors comprising these sequences. Using the antibiotic resistance, it is possible therefore to select clones in which the pDD vector (or any other vector) contains the DD cassette on the basis of the acquired resistance.

Functional leader/signal sequences are those identified in several prokaryotic genes for locating a protein into the periplasmic space, such as PelB (from *Erwinia carotovora*; described in the examples), MalE4, PhoA4, LamB4, and Lpp4. Improved leader sequences have been also identified (Strobel et al., 2003).

The DD cassette-mediated expression of the fusion protein, which is displayed by means of the leader sequence, is made possible by the presence of a promoter (constitutive or inducible in the bacteria) that is operatively linked in 5' to the starting ATG-containing, leader sequence encoding said protein sequence, within the DD cassette. The 5' end of this promoter is separated from the other end of the DD cassette that may comprise one or more additional genes, by a stuffer DNA sequence.

The literature provides many comparative examples on how to optimize both vector design and culture conditions in order to improve the expression of the displayed protein, and that can be used in adapting the vectors of the invention for specific uses ("Phage display: A practical Approach", vol. 266, ed. Clackson and Lowman H, Oxford Univ. Press, 2004; "Phage Display: A laboratory Manual", Burton D R et al., CSHL Press, 2001; Corisdeo and Wang, 2004; Kirsch et al., 2005; Sidhu et al., 2000; Benhar, 2001; Sidhu, 2001; Szardenings, 2003; Bradbury and Marks, 2004; Hust and Dubel, 2004; Mancini et al., 2004; Pini et al., 2004; Conrad and Scheller, 2005; Hust and Dubel, 2005; Silacci et al., 2005; Smith et al., 2005).

The stuffer DNA between the DIS linkers or in the DD cassette can contain further elements that may be desirable to have in the DD cassette, such as one or more additional genes (i.e. DNA sequences that can be autonomously transcribed and translated into a protein) that may or may not affect the cloning and/or the display process. For example, a further selection marker gene (different from the ones comprised in the backbone and in the display cassette of the empty vector, if present before the cloning) can be integrated in the DD cassette, allowing the selection of phagemid vectors containing the correct DD cassette.

Alternatively, the additional gene can encode another different functional coat protein of the filamentous phage, a protein modifying the metabolism or the physiology of the bacterial cell (Bothmann and Pluckthun, 1998), or a protein interacting with or modulating the activity of the protein to be displayed fused to the functional coat protein by means of the DIS linker. An example of this latter case is represented by an immunoglobulin light chain gene that, once expressed in the bacteria, can heterodimerize with a segment of an immunoglobulin heavy chain fused to the functional coat protein, forming a complete antigen binding site on the surface of the phage. Other heterodimerization partners that can be expressed in this way are those typical of some membrane receptor proteins. However, such additional, complete genes in the DD cassette are intended to be transcribed and translated independently from the orientation in which the DD cassette is inserted, even though their expression can be put under the control of inducible promoter systems.

The DD cassette can be generated, cloned, maintained, and modified in any type of vector, including a pDD vector. The elements cloned in the DD cassette can be arranged in different manners (Hoet et al., 2005; Kirsch et al., 2005; Schoonbroodt et al., 2005) and can also be shuffled exploiting Cre/Lox-based systems in bacteria (Sblattero and Bradbury, 2000), either when the DD cassette is cloned in a phagemid of the invention or when it is inserted in another type of vector. The phagemid vectors of the invention allow the construction of an expression unit consisting of a transcribable and translatable sequence for a fusion protein including either one or other of the two functional coat proteins present in the vector. The promoter, a ribosome binding site (if needed), the start codon, and the leader/secretion sequence is provided by the DD cassette, that can drive accordingly the expression of a mono or bicistonic transcript having the DNA coding for the functional coat protein at its 3' end. The DD cassette can also contain the sequence sufficient to establish the expression of the heterologous sequence as a soluble protein.

The term "promoter" refers to a sequence at which transcription can be initiated by a RNA polymerase. Exemplary prokaryotic promoters include a polymerase binding site and optionally a site for sigma factor. A promoter can be constitutive (i.e. always active) or regulatable (i.e. active only under certain conditions). In E. coli, promoters are between 30-50 base pairs in length. Regulatable promoters can respond to regulatory chemicals such as glucose, lactose, IPTG, cAMP, tryptophan, or other small molecules. Promoters can be regulated by repressors and/or activators and can be also modulated by altering culture conditions (e.g. changing temperature, pH, nutrients, etc.).

Given the fundamental importance of the restriction sites of the DIS linkers in the phagemid vector and in the DD cassette in order to obtain the bidirectional cloning and display process of the invention, their number should be ascertained, in particular in the DD cassette (but also in the pDD backbone if necessary), by preliminar sequencing and/or digesting the DNA. In the case where additional unwanted sites are present, technologies such as PCR mutagenesis (as shown in the examples) allow the modification of these sites without altering qualitatively the activities associated to the original DNA.

An optimization of the DNA sequences to be included in the phagemid vector and coding for the functional coat protein, for the DIS linker, or for the proteins expressed by means of the functional display cassette can be achieved by selecting the DNA sequence in which the codon usage is the most appropriate for the bacterial cells (Rodi et al., 2002). Software and criteria to be applied to for obtaining a codon adaptation and optimization according to the organism expressing the sequence are available and help to choose a DNA sequence that lacks restriction sites potentially dangerous for cloning into the phagemid vector itself or into other expression vectors, once the correct heterologous sequence has been detected (Grote et al., 2005).

The substitution of the DNA cassette in the empty vector (or of another DD cassette) with the desired DD cassette is made possible by the restriction site present only in the two DIS linkers of the phagemid vector and in the 5' and 3' end of the DD cassette which, given the structure of the phagemid vector and the opposite orientations of the two functional coat proteins juxtaposed to the two DIS linkers, can be integrated in two equally possible orientations. Therefore, the protein(s) to be displayed can be joined and expressed in frame with one or the other of said coat protein using the protein sequence encoded by the DIS linker.

Thus, the invention provides means for generating, starting from a single empty vector and a single DD cassette, two distinct display phagemid vectors that can be used to transform bacteria cell cultures. Depending on the further use of the resulting recombinant phage, it can be appropriate to maintain the cell culture, obtained by a single cloning and transformation step, as containing a mixture of transformed cells containing pDD vectors expressing either one or the other fusion protein. Alternatively, single clones in the original mixed cell culture can be analyzed (e.g. by plasmid DNA extraction, followed by DNA sequencing and/or restriction analysis) to identify and propagate separately specific clones that contains only one of two type of pDD vectors having the desired orientation.

Moreover, the choice and the location of the selection marker genes in the phagemid vector (empty or already comprising a DD cassette) allow applying specific culture conditions to select bacterial clones containing the desired phagemid vector.

Once understood the invention, a large variety of phagemid vectors comprising a DD cassette allowing the cloning, expression, and display of at least a protein sequence fused to either one or the other of two functional coat proteins can be generated. In particular, the modular structure and alternative ways for insertion of the DD cassette allows displaying large libraries of protein sequences, as generally required for screening assays based on the phage display system, with the advantage of having the same proteins potentially displayed on two distinct coat proteins in a single phage library generated with a single cloning and transformation process. This approach can considerably increase the opportunities of identifying relevant sequences in a phage library, without repeating the cloning and/or the transformation steps as required so far in the technologies disclosed in the literature, for example in the case of recombinant phage expressing fusion proteins in cp3 or cp8 (Kretzschmar and Geiser, 1995; Wang et al., 1997; Rousch et al., 1998; Zwick et al., 1998; Adda et al., 1999; Verhaert et al., 1999; Yip et al., 2001; Al-bukhari et al., 2002; Jacobsson et al., 2003; O'Connor K et al., 2005). Thus, improved phage display libraries, and greater levels of diversity can be obtained by transforming bacterial cells with phagemid vectors allowing the bidirectional cloning of a DD cassette.

At this scope, the DD cassette contains appropriate restriction sites for cloning a sequence to be displayed in the correct frame between the signal/leader sequences and the site that is used for the insertion in the DIS linker of the pDD vector. If more than one sequence has to be displayed in distinct recombinant phage (as usually happens with repertoires of peptides or antibodies), the panel of DNA fragments to be cloned are ligated within a DD cassette by means of such restriction sites, generating a corresponding double panel of phagemids (that is, having each DNA fragment operatively linked to DNA coding for either one or the other functional coat protein). If the library is constructed in a DD cassette already cloned in a pDD vector (that is, in-frame with a specific functional coat protein), such library should be subjected to the digestion with a restriction enzyme cutting within the DIS linker and to the ligation with a pDD vector cut with an enzyme providing compatible ends in order to obtain the desired bidirectional cloning of the DD cassette.

A "transformed cell" is a cell containing self replicating DNA that is foreign to the cell and that can be introduced by any method (e.g. electroporation, chemical transformation, or infection, including phage infection).

The present invention provides kits and methods for generating phage display libraries in which each single protein sequence is present in the library fused to either one or other of two coat proteins, by making use of a single phagemid vector for bidirectional cloning of a single DD cassette, and applying a single, DIS linker-based cloning and transformation step. The kits may include the sole phagemid vector for bidirectional cloning of the DD cassette, or vectors and primers for generating DD cassettes compatible with the pDD vectors and allowing the correct cloning of cDNA/genomic sequences, PCR amplification products, or any other double stranded synthetic DNA coding for a protein sequence to be displayed using a functional coat protein.

The method for generating a cell or a phage library, wherein each protein sequence of said library is fused at the N-terminus of either one or the other of two functional coat proteins, comprises:

(a) inserting a DD cassette in correspondence of the DNA linkers of a phagemid vector for the bidirectional cloning of a DNA coding for an amino acid sequence to be fused at the N-terminus of either one or the other of two functional coat proteins; and (b) transforming bacterial cells with the resulting vectors.

These steps would apply also to methods for cloning and expressing any specific amino acid sequence on the surface of a filamentous phage, in particular whenever it is desirable to detect the presence of such amino acid sequence into a library.

When using a DIS linker such the one described in the examples, the insertion of the DD cassette can be obtained by ligating a DD cassette and a vector that have been digested with BglI and have compatible ends.

The libraries obtained using the vectors and the methods of the invention can be selected or "panned" using the technologies commonly disclosed in reviews (Mancini et al., 2004; Pini et al., 2004; Rhyner et al., 2004) or those improved methods described in recent articles for choosing the more appropriate strategy and format (Lou et al., 2001; Vanhercke et al., 2005).

The invention provides novel phagemid vectors that contain both a phage origin of replication and a phage-independent origin. Phagemids do not include a complete set of phage genes, e.g., sufficient number of genes to produce phage particles. Cells that harbor phagemid can produce phage-like particles that contain the phagemid genome when the cells are infected by a "helper" phage that carries requisite phage genes not present in the phagemid. The phagemid vector needs an helper phage in order to infect bacterial cells.

Apart from the one disclosed in the examples, other appropriate helper phage, together with bacterial culture condition and E. Coli strains supporting their use, can be identified in the literature (Rondot et al., 2001; Baek et al., 2002; Intasai et al., 2003; Kramer et al., 2003; Soltes et al., 2003; Ravn et al., 2004). In general, the helper phage should support the infection and the propagation of the recombinant phage whatever the orientation in which the DD cassette is inserted, unless it is desired to allow the infection and the propagation of only one type of recombinant phage (i.e. that display proteins fused to only a specific functional coat protein).

The sequence to be included in the DD cassette and to fused to the N-terminus of either one or the other functional coat protein sequence present in pDD vector by means of a DIS linker can be any sequence of interest known to be interacting with a ligand or a target molecule such as antibodies (including fragments like Fabs, ScFV, and any other epitope-binding fragment or derivative), epitopes, epitope-binding regions, antigens, allergens, bioactive peptides, enzymes, enzyme inhibitors, enzymatic catalytic sites, DNA-binding proteins, isolated protein domains, ligands for receptors, receptors, growth factors, cytokines, and contiguous or overlapping fragments of the protein sequence of interest.

In the case of proteins to be displayed that are formed by two distinct protein sequences (such as the variable regions of an heavy and a light chain of an immunoglobulin forming a fab), one of the sequences is cloned in the DD cassette to be fused to a functional coat protein, while the other one is cloned and autonomously expressed by a complete, separate gene cloned within the DD cassette as well, or in the backbone of pDD vector.

The DD cassette should allow the correct transcription and translation of a DNA sequence to be fused on a functional coat protein that has been either previously cloned and/or amplified from other vectors, cDNA libraries, or genomic libraries, or nucleic acids generated by chemical synthesis. In particular, the DNA should encode for protein having therapeutic or diagnostic interest, such as mammalian proteins, and more preferably for human proteins, or for human pathogenic organisms (e.g. virus). The source for DNA encoding human proteins can be any human cell and tissue but, given the extensive use of phage display technologies to identify immunity-related proteins (such as antibodies or antigens), the preferred source of human DNA and cDNA are either cells expressing antigens having diagnostic or therapeutic interest (e.g. cancer cells) or antibody-producing cells that can be isolated from blood, bone marrow, tonsils, or cancers (such as tumors-infiltrating lymphocytes, total peripheral blood lymphocytes, circulating memory B cells). These cells can be isolated from specific individuals (naive or antigen-exposed) and can be previously selected by any appropriate criteria (e.g. B cells expressing antibodies having the IgG isotype or expressing CD27 on the surface).

Phagemid vectors prepared in accordance with the present invention can be used to simultaneously express a large number of protein sequences, such as those encoded in cDNA libraries derived from cells or tissues, in a phage or cell library fused to either one or the other of two coat proteins, taking advantage of the fact that different proteins can be better expressed and/or better displayed in one of the two possible conformations determined by the bidirectional cloning process. Moreover, the phage can be detected using antibodies against the coat proteins themselves (Dente et al., 1994; Bhardwaj et al., 1995).

The vectors of the invention can also be used to reproduce other more complex strategies involving the formation of complexes between two differentially deleted coat proteins that can be mediated by the interaction of heterologous protein sequences, such as in SIP (Hennecke et al., 1998; Cebe and Geiser, 2000). Alternatively, the vector of the invention can be adapted to generate "landscape" recombinant phage (Petrenko et al., 2002), or bifunctional phage (Gao et al., 1999; Chen et al., 2004) wherein display of one category of protein sequences can be achieved to either one or the other functional coat proteins.

The libraries of phage produced according to the methods of the invention can be screened using any screening assay known to be applicable with phage. For example, the phage can be exposed to a purified antigen, soluble or immobilized (e.g. on a plate or on beads) or exposed to whole cells, tissues, or animals, in order to identify phage that adhere to targets present in complex structures, and in particular in physiologically or therapeutically relevant locations (e.g. binding to cancer cells or to endothelium in vivo or in vitro) for target identification/validation. The selection of the phage made against these antigens can be considered as a positive selection (i.e. for detecting molecules binding to specific ligands) or as a negative selection (i.e. for eliminating phage binding to certain ligands).

Then, the selected phagemid vectors in which a heterologous sequence has been cloned, expressed, and specifically isolated on the basis of its binding for a specific ligand, can be extracted from the bacterial cells, and sequenced, PCR-amplified, and/or recloned into another appropriate vector, for example for the large scale recombinant production in bacterial, plant, yeast, or mammalian cells.

The vectors, the methods, and the libraries of the invention can be adapted to any of the known uses of phage display, once the sequences to be displayed are provided in a format that can be correctly cloned and expressed by means of the functional double display cassette. The sequences can be derived from large cDNA/ESTs libraries, or even genome-/proteome-wide libraries that are screened for identifying relevant Open Reading Frames or families of protein domains and sequences (Rosander et al., 2002; Jacobsson et al., 2003; Faix et al., 2004). In addition to antibodies, phage display technologies can be used to detect bioactive peptide selection, when the selection is coupled to an appropriate assay for the biological activity or computational modelling (Pastor et al., 2004; Falciani et al., 2005).

Libraries of non-random or random peptides displayed by bacteriophage can be screened to select phage expressing peptides that specifically bind antibodies, so that the peptide sequence motifs expressed by the phage allow the definition of allergens, antiidiotypes, B- or T-cell epitopes, or vaccines (Zhong et al., 1997; Davies et al., 2000; De Berardinis et al., 2000; Goletz et al., 2002). Alternatively, "sandwich" assays are based on the cloning and the expression of only the variable chain on the phage, meanwhile the antigen and one variable chain are provided into solution, in order to take advantage of the antigen-driven stabilization of the variable light and heavy chain complex (Watanabe et al., 2002).

Further manipulation of the phage can be made during the selection process for various reasons. For example, mixtures of antibody and antigen expressing phage can be incubated in solution and the immune complexes are precipitated with Protein G or Protein A bound to Sepharose beads. The precipitated phage can then be used for inducing infection of *E. Coli* or for measuring interactions by ELISA, so that it is possible to quantify the phage precipitated by determining the number of plaques produced (Al-bukhari et al., 2002).

A more general analysis of the biological activities of a protein sequence expressed and screened using phage display technologies can be performed by using whole cells or tissues to which the libraries are exposed. The relevant recombinant phage are then selected on the basis of their binding (or absence of binding) to complex structures such as the surface of human cells having specific features, including tumor cells, helping the identification of novel markers and therapeutic targets (Edwards et al., 2000; Landon and Deutscher, 2003; Mutuberria et al., 2004; Shukla and Krag, 2005). Alternatively, the interaction can also be not associated only to the binding of the phage to the cells but to its internalization, allowing the identification of cell-specific peptides or antibodies having this specific activity (Legendre and Fastrez, 2002; Florea et al., 2003 Elrick et al., 2005).

The detection of the interaction with the specific ligand can be performed by applying the usual panning methods, or by applying more sophisticated biophysical technologies for assessment of interactions between the displayed protein and its binding partner, such as fluorescence-based spectroscopy or microscopy (Lagerkvist et al., 2001; Jaye et al., 2004), phosphatase reaction (Han et al., 2004), or other high-throughput technologies (Paus et al., 2003; Rhyner et al., 2004; Steukers et al., 2006). In general, the success of a panning approach is also dependent on the dimension of the screened library since, as shown for many libraries displaying antibody fragments, protein with higher affinity for a target are found in libraries having a larger number of distinct sequences cloned within them (Hust and Dubel, 2005).

In general, the recombinant phage or fusion proteins obtained by the methods of invention can be directly used for binding, detecting, neutralizing, and/or altering a ligand, a cell, or a target molecule, wherein said recombinant phage or fusion proteins are in isolated forms or in the forms of mixtures.

Once that one or more protein sequences, displayed as a fusion protein with either one or the other of the selected coat protein cloned and arranged into a phagemid vector according to the invention, have been selected following one or more panning cycles, the associated recombinant phage and the relevant DNA sequence can be isolated and characterized according to the methods known in the art (e.g. separated from the phagemid vector using restriction enzymes, directly sequenced, and/or amplified by PCR). These sequences can be then transferred into more appropriate vectors for further modification and/or expression into prokaryotic or eukaryotic host cells, as described in many books and reviews on how to clone and produce recombinant proteins, including some titles in the series "A Practical Approach" published by Oxford University Press ("DNA Cloning 2: Expression Systems", 1995; "DNA Cloning 4: Mammalian Systems", 1996; "Protein Expression", 1999; "Protein Purification Techniques", 2001).

The DNA sequence coding for the displayed and selected protein sequence, once inserted into a suitable episomal or non-homologously or homologously integrating vectors, can be introduced in the appropriate host cells by any suitable means (transformation, transfection, conjugation, protoplast fusion, electroporation, calcium phosphate precipitation, direct microinjection, etc.) to transform them. Factors of importance in selecting a particular plasmid or viral vector include: the ease with which recipient cells that contain the vector, may be recognized and selected from those recipient cells which do not contain the vector; the number of copies of the vector which are desired in a particular host; and whether it is desirable to be able to "shuttle" the vector between host cells of different species.

The vectors should allow the expression of the fusion protein in the prokaryotic or eukaryotic host cell under the control of transcriptional initiation/termination regulatory sequences, which are chosen to be constitutively active or inducible in said cell. A cell line substantially enriched in such cells can be then isolated to provide a stable cell line. For eukaryotic hosts (e.g. yeasts, insect or mammalian cells), different transcriptional and translational regulatory sequences may be employed, depending on the nature of the host. They may be derived from viral sources, such as adenovirus, bovine papilloma virus, Simian virus or the like, where the regulatory signals are associated with a particular gene which has a high level of expression. Examples are the TK promoter of the Herpes virus, the SV40 early promoter, the yeast gal4 gene promoter, etc. Transcriptional initiation regulatory signals may be selected which allow for repression and activation, so that expression of the genes can be modulated. The cells which have been stably transformed by the introduced DNA can be selected by also introducing one or more markers which allow for selection of host cells which contain the expression vector. The marker may also provide for phototrophy to an auxotropic host, biocide resistance, e.g. antibiotics, or heavy metals such as copper, or the like. The selectable marker gene can either be directly linked to the DNA gene sequences to be expressed, or introduced into the same cell by co-transfection. Additional transcriptional regulatory elements may also be needed for optimal expression.

Host cells may be either prokaryotic or eukaryotic. Preferred are eukaryotic hosts, e.g. mammalian cells, such as human, monkey, mouse, insect (using baculo virus-based expression systems) and Chinese Hamster Ovary (CHO) cells, because they provide post-translational modifications to protein molecules, including correct folding or glycosylation at correct sites. Also yeast cells can carry out post-translational peptide modifications including glycosylation. A number of recombinant DNA strategies exist which utilize strong promoter sequences and high copy number of plasmids that can be utilized for production of the desired proteins in yeast. Yeast recognize leader sequences in cloned mammalian gene products and secrete peptides bearing leader sequences (i.e., pre-peptides). For long-term, high-yield production of a recombinant polypeptide, stable expression is preferred. For example, cell lines which stably express the polypeptide of interest may be transformed using expression vectors which may contain viral origins of replication and/or endogenous expression elements and a selectable marker gene on the same or on a separate vector. Following the introduction of the vector, cells may be allowed to grow for 1-2 days in an enriched media before they are switched to selective media. The purpose of the selectable marker is to confer resistance to selection, and its presence allows growth and recovery of cells that successfully express the introduced sequences. Resistant clones of stably transformed cells may proliferate using tissue culture techniques appropriate to the cell type. A cell line substantially enriched in such cells can be then isolated to provide a stable cell line.

Mammalian cell lines available as hosts for expression are known in the art and include many immortalized cell lines available from the American Type Culture Collection (ATCC) including, but not limited to, Chinese hamster ovary (CHO), HeLa, baby hamster kidney (BHK), monkey kidney (COS), C127, 3T3, BHK, HEK 293, Per.C6, Bowes melanoma and human hepatocellular carcinoma (for example Hep G2) cells and a number of other cell lines. In the baculovirus system, the materials for baculovirus/insect cell expression systems are commercially available in kit form (e.g. commercialized by Invitrogen).

In the case of phage expressing immunoglobulin variable chains, in particular human immunoglobulin variable chains, an important modification is the conversion of the selected Fab or scFV into a full immunoglobulin protein having a preferred isotype and constant region. This kind of modification allows, for example, generating full human monoclonal antibodies of all isotypes constructed from phage display library-derived single-chain Fv or Fabs and expressing in mammalian or insect cells (Ames et al., 1995; Mahler et al., 1997; Persic et al., 1997; Boel et al., 2000; Liang et al., 2001; Guttieri et al., 2003). The proteins selected using the vectors and the methods of the invention can be then cloned and expressed in other vectors allowing, for example, the fusion to another display scaffold such as the maltose-binding protein (Zwick et al., 1998) or their expression and selection not as isolated recombinant proteins but as a mixture of recombinant proteins (Sharon et al., 2005; Meijer et al., 2006). In the case of peptides (and of proteins below 100 amino acids) displayed and selected according to the invention, these sequences are short enough to be produced using chemical synthesis technologies, such as solid phase synthesis and liquid phase synthesis. As a solid phase synthesis, for example, the amino acid corresponding to the carboxy-terminus of the peptide to be synthesized is bound to a support which is insoluble in organic solvents, and by alternate repetition of reactions, one wherein amino acids with their amino groups and side chain functional groups protected with appropriate protective groups are condensed one by one in order from the carboxy-terminus to the amino-terminus, and one where the amino acids bound to the resin or the protective group of the amino groups of the peptides are released, the peptide chain is thus extended in this manner. The purified peptides can also include other chemical groups introduced during synthesis or they can be further modified to form dendrimers (Pini et al., 2005).

Purification of the recombinant proteins can be carried out by any one of the methods known for this purpose, i.e. any conventional procedure involving extraction, precipitation, chromatography, electrophoresis, or the like. A further purification procedure that may be used in preference for purifying the protein of the invention is affinity chromatography using monoclonal antibodies or affinity groups, which bind the target protein and which are produced and immobilized on a gel matrix contained within a column. Impure preparations containing the proteins are passed through the column. The protein will be bound to the column by heparin, protein A, protein G, or by the specific antibody while the impurities will pass through. After washing, the protein is eluted from the gel by a change in pH or ionic strength. Alternatively, HPLC (High Performance Liquid Chromatography) can be used. The elusion can be carried using a water-acetonitrile-based solvent commonly employed for protein purification.

Phage-displayed protein sequences identified by the methods of the invention can find several other applications, such as immunodetection, the study of T cell/MHC-related activities (Matsushita et al., 2001; Zhao et al., 2001; Kurokawa et al., 2002; Li et al., 2005), and B or T cell epitope-mapping of biologically active antibodies or proteins (Bugli et al., 2001;

Dromey et al., 2004; Di Niro et al., 2005). Combinatorial libraries generated according to the methods of the invention can be also used for protein engineering, by expressing in each phage a sequence variant of a protein and then screening the phage to identify those expressing fusion protein variants having higher affinity for a receptor, a ligand, an antigen, or an enzymatic substrate (Heinis et al., 2001; Schooltink and Rose-John, 2005) as well as the detection of protective or pathogenic human antibodies (Ditzel, 2000). Alternatively, these variants can be selected on the basis of their stability to proteolysis (Bai and Feng, 2004). The phage display technology can be also used for characterizing proteins recognizing non-protein targets such as fatty acids (Gargir et al., 2002), plant hormones (Suzuki et al., 2005), DNA (Nilsson et al., 2000), or glycans (van de Westerlo et al., 2002; Ravn et al., 2004).

The examples describe the design of constructs and experiments for establishing the phage display technology of the invention by making use of DNA sequences encoding two coat proteins (cp3 and cp8) that have been amplified and mutated at the N-terminus using a DIS linker2 containing a rare cutting restriction enzyme site and a Gly4Ser (SEQ ID NO: 53) based sequence. Phagemid vectors expressing separately the N-terminal modified cp3 and cp8 proteins (cp3* and cp8*) have been generated. The production of cells and recombinant phage correctly expressing heterologous sequences (a peptide or human Fab) fused at the N-terminus of either cp3* or cp8* DNA coding sequence has been demonstrated. The expression of the modified phage protein-peptide fusion protein does not affect phage production, assembly and infectivity. The system has been validated demonstrating that affinity selection of phage expressing the modified proteins performed on the basis of the binding characteristics of the fused peptide and antibody is efficient, showing the correct assembly of the Fab molecule in the periplasmic space.

The coat protein sequences modified with the DIS linker can be inserted in the appropriate orientation into a pBluescript-derived scaffold. This basic pDD vector has been ligated with a DD cassette containing a sequence to be displayed (a peptide or antibody variable regions) and an antibiotic resistance marker, allowing the selection of recombinant pDD vectors in which these sequences have been fused at the N-terminus ofeither one or the other of two the functional coat protein.

Other features and advantages of the present invention will become more apparent from the following detailed examples. Additional embodiments of the invention can include any combination of features described herein. The contents of all references, pending patent applications and published patents, cited throughout this application are hereby expressly incorporated by reference.

EXAMPLES

Example 1

Preparation and Expression of a DIS Linker2-Modified DNA Sequence Encoding a Filamentous Phage Coat Protein 3 (cp3*) for Displaying Proteins and Peptides a) Materials & Methods
Production of M13 Helper Double-Stranded DNA.

A commercially available bacteriophage M13 helper (VCSM13, Stratagene, La Jolla, Calif.) was used as a source for isolating its double-stranded replicative form DNA. Into 2 ml of LB medium, 50 µl of a culture of a bacterial strain carrying an F' episome (*E. Coli* XL1 Blue, Stratagene, La Jolla, Calif.) was admixed with $1\times10^{11}$ bacteriophage particles. The admixture was incubated for 4 to 5 hours at 37° C. with constant agitation. The admixture was then centrifuged at 12,000×g for 5 minutes to pellet the infected bacteria. After the supernatant was removed, the bacteria pellet was used in a standard DNA extraction protocol using Qiagen mini prep kit and analysed in 1% agarose gel electrophoresis.

Production of a Gene Encoding a DIS Linker2 N-Terminal Modified cp3 Protein (cp3* Protein)

The PCR reaction for generating the gene encoding cp3* was carried out using the primers cp3*FW and cp3*RW (SEQ ID NO.: 13 and SEQ ID NO.: 14; Table I). The PCR amplification was carried out using Expand High Fidelity (Roche), according to the manufacturer instructions, using 50 pg of template DNA and 300 mM of each primer. The PCR conditions used were: 95° C. for 2 min (1 cycle); 95° C. for 20 sec, 63° C. for 30 sec, 72° C. for 40 sec (35 cycles). After the PCR amplification, 2.5 units of AmpliTaq polymerase (Applied Biosystems, Foster City, Calif.) were added to the PCR reaction, which was incubated for further 20 minutes at 72° C. in order to allow the addition of a single deoxyadenosine, in a template-independent fashion, to the 3'-ends of the amplified fragments. The PCR product was electrophoresed in a 1.5% agarose gel and purified using gel extraction kit (Qiagen).

The cp3* gene was then ligated into pGEM T-Easy vector (Promega), by means of a single deoxyadenosine added at the 3' ends, following the manufacturer instructions. The ligation mixture was used to transform electrocompetent *E. Coli* DH5alpha cells. The day after, 10 white colonies were picked up, inoculated into 4 ml of Luria-Bertani broth (LB; "Molecular Cloning: A Laboratory Manual", Sambrook et al., Cold Spring Harbor Press, NY, 1989), and incubated overnight at 37° C. in constant agitation. The day after, 2 ml of bacteria suspension were used for plasmid DNA extraction/purification using miniprep Qiagen kit. The pGEM T-Easy plasmids carrying cp3* gene were then analysed by restriction endonuclease enzymes. One clone was chosen and sequenced in order to verify the correct nucleotide sequence of the gene encoding cp3*, identifying the mutation $A_{523}$ to $G_{523}$ in the nucleotide sequence produces an amino acidic substitution $Ser_{175}$ to $Gly_{175}$.

The Basic pRIB Vector

The basic pRIB vector comprises elements present in the pBluescript II SK(+) vector (Stratagene, Genbank Acc. No. X52328), including a phage replication origin (F1(+); bp 3-459), a plasmid replication origin (ColE1; bp 1032-1972), and an ampicillin resistance gene ($Amp^r$, bp 1975-2832).

Additional three elements are included in an expression cassette contained in this vector. A first element comprises a promoter of Lac Z operon (SEQ ID NO.: 23), an ATG-containing leader sequence PelB (SEQ ID NO.: 24 and SEQ ID NO.: 25), and a ScaI-XbaI cloning site allowing the insertion of a DNA encoding a protein sequence (e.g. an immunoglobulin light chain), in-frame with the leader sequence (PelB, at the 5' end) and cloned as a fragment ending with a stop codon. The second element is a chloramphenicol resistance gene (CAT). The third element comprises a promoter of Lac Z operon (SEQ ID NO.: 23), an ATG-containing leader sequence PelB, XhoI-SpeI cloning site allowing the insertion of a DNA encoding a protein sequence (e.g. the variable region on an immunoglobulin heavy chain), in-frame with the leader sequence (PelB, at the 5' end) and with a DNA sequence (at the 3' end) encoding a functional coat protein (e.g. cp3*) including the stop codon and that can be cloned using a SpeI-NheI cloning site. In the empty vector, the ScaI- XbaI, SpeI-NheI, and XhoI-SpeI cloning sites are separated by DNA stuffer fragments with compatible ends that are replaced during the cloning steps. For example, a stuffer DNA sequence can be inserted in the ScaI-XbaI cloning site by ligating a synthetic fragment obtained by annealing two oligonucleotides (LCstuffer FW and LCstuffer RW; SEQ ID NO.: 26 and SEQ ID NO.: 27; Table I) that have single stranded ends compatible with such restriction sites.

Construction of the pRIB1 Vectors for the Expression of cp3* and of the Related Fusion Proteins The pRIB1-cp3* vector was constructed using a pRIB basic vector in which the SpeI-NheI fragment encoding cp3* excised from pGEM-T Easy was ligated in the SpeI-NheI cloning site described above. The ligation mixture was used to transform electrocompetent E. Coli DH5alfa cells and The day after, 10 colonies were picked, inoculated into 4 ml LB broth, and incubated overnight at 37° C. in constant agitation. The day after, 2 ml of bacterial suspension were used for plasmid DNA extraction/purification using miniprep Qiagen kit. The plasmids carrying the modified cp3* gene were then analysed by restriction endonuclease enzymes in order to verify the correct cp3* orientation.

The pRIB1-Hacp3* vector was constructed starting from pRIB1-cp3*, which was double digested with XhoI and SpeI and ligated with a double stranded, synthetic DNA sequence encoding the epitope from influenza virus hemagglutinin (HA tag sequence YPYDVPDYA (SEQ ID NO: 55)), and having XhoI and SpeI compatible ends. The HA tag linker was obtained by mixing the oligonucleotides (HA tag linker FW and HA tag linker RW; see sequence in Table I; SEQ ID NO.: 17 and SEQ ID NO.: 18) at a concentration of 1 µM and denaturating them at 95° C. for 5 minutes. The oligonucleotides mixture was then transferred in a 95° C. pre-warmed water and left to cool at room temperature in order to obtain the specific annealing. The ligation mixture, composed by XhoI-SpeI double digested pRIB1-cp3* and the HA tag linker, was used to transform electrocompetent E. Coli DH5alpha cells. The day after, 10 colonies were picked up, inoculated into 4 ml of LB and left o/n at 37° C. in constant agitation. The day after, 2 ml of bacteria suspension were used for plasmid DNA extraction/purification using miniprep Qiagen kit and then analysed by restriction endonuclease enzymes in order to verify the presence of the HA tag. One clone showing the desired characteristics, that is having the HA tag fused in-frame with cp3*, was chosen and used for the expression experiments.

The pRIB1-e44 cp3* vector was constructed using the DNA sequences encoding the heavy and light chain of human monoclonal recombinant Fab (called e44 but identical to e8) isolated from a phage display library for its affinity to the Hepatitis C virus E2 protein (Burioni et al., 1998b). The e44 heavy and light chains were cloned into pRIB1-cp3* using the XhoI-SpeI and the XbaI-ScaI cloning sites, respectively. The transformed E. Coli clone showing the desired characteristics, thus having e44 heavy chain fused in-frame with cp3* and the e44 light chain cloned between the XbaI-ScaI sites, was used for expression experiments. A control vector (pRIB-e44 cp3) was constructed in the same way using a non-modified cp3 sequence (without a DIS linker2).

Control pRIB plasmids that encode for cp3, with or without a fab (e44) or a peptide (HA tag) fused to the N-terminus, have been generated (and named pRIB-cp3, pRIB-HAcp3, pRIB-e44 cp3) on the basis of phagemids available in the literature (Burioni et al., 1997; Burioni et al., 1998).

Analysis of HAcp3* and e44 cp3* Expression Using pRIB1-cp3* Based Plasmids 10 ml of super broth (SB; "Molecular Cloning: A Laboratory Manual", Sambrook et al., Cold Spring Harbor Press, NY, 1989) containing ampicillin (100 µg/ml) was inoculated with the appropriate E. Coli XL1Blue clone (containing pRIB1-cp3*, pRIB1-HAcp3*, pRIB1-e44 cp3*, or pRIB1-e44 cp3), and grown for 8 hours at 37° C. in a rotary shaker. At this point, isopropylthio-β-D galactoside (IPTG, 1 mmol/L; Sigma, Saint Louis, Mich.) was added to the growing bacteria that were further incubated overnight at 30° C. Cells were then harvested by centrifugation, resuspended in 1 ml of phosphate-buffered saline (PBS; "Molecular Cloning: A Laboratory Manual", Sambrook et al., Cold Spring Harbor Press, NY, 1989) and subjected to a freeze-thawing procedure (3 cycles of 37° C. and −80° C., each step for 15 minutes). Cell debris was pelleted by centrifugation at 15000 g at room temperature in a microcentrifuge, and the supernatant was used to quantify the protein content. 20 micrograms of total proteins were loaded into a 12% acrylamide gel ("Molecular Cloning: A Laboratory Manual", Sambrook et al., Cold Spring Harbor Press, NY, 1989) and separated by electrophoresis. The resolved proteins were transferred to nitrocellulose membranes, which were then blocked by a first 1 hour incubation with PBS/0.1% Tween-20 (Sigma) containing 10% milk. The membranes were then washed and incubated with anti-HA tag antibody (HA.11, Covance) diluted 1:1000, or a goat anti-human Fab conjugated to horseradish peroxidase (HRP, Sigma) diluted 1:10000 in PBS/0.1% Tween-20 containing 5% milk. After a second 1-hour incubation, the membranes were washed three times with PBS/0.1% Tween-20. For Fab detection the membrane was subjected directly to enhanced chemiluminescence detection using the Supersignal West Pico chemiluminescent substrate (Pierce). For HA tag detection, the membrane was incubated for further 1 hour with an anti mouse conjugated to horseradish peroxidase in PBS/0.1% Tween-20 (dilution 1:1000). After three washes with PBS/0.1% Tween-20 the membranes were subjected to enhanced chemiluminescence detection using the Supersignal West Pico chemiluminescent substrate (Pierce).

b) Results

The sequence of the natural M13 gene encoding cp3 was modified through PCR amplification in order to be N-terminally truncated and to incorporate a DIS linker2 with the restriction endonuclease sites SpeI and SfiI (at the 5', encoding a 12 amino acid sequence) and a NheI restriction site following the stop codon (at the 3'; FIG. 1). This variant, also known as BAC76618 and containing amino acid 216-424 of Enterobacteria phage M13 cp3 protein (SWISSPROT Acc. No. P69168), lacks the original signal sequence and additional N-terminal structural elements but it is still able to present correctly fusion proteins, as shown in phagemids used for this scope such as pFCAH-E8d (GENBANK Acc. No. AB096107).

The resulting PCR product encoding the N-terminally modified cp3 (cp3*) coding for cp3* protein (221 amino acids; FIG. 2), was then ligated into pGEM T-Easy and sequenced. The amplified segment contains a mutation $A_{523}$ to $G_{523}$ in the nucleotide sequence producing an amino acidic substitution $Ser_{175}$ to $Gly_{175}$ having no effect on protein location or activity as tested in the present patent application.

The basic pRIB vector comprises elements present in the well known pBluescript II SK(+) vector that are sufficient for plasmid and phage replication, as well as an antibiotic resistance gene. This vector further contains an expression cassette with an additional marker gene (cloramphenicol resistance gene) and two transcriptional units. Both transcriptional units include the promoter of lac operon, an ATG-containing leader sequence PelB, and specific cloning sites allowing the insertion of a DNA encoding a protein sequence. In particular, one of such sites allows the fusion with a DNA sequence encoding a functional coat protein to be used for expressing heterologous protein sequences on the surface of recombinant phage (e.g. cp3*).

The resulting pRIB1-cp3* was then used for generating a series of pRIB1 vectors in which the DNA encoding either a well characterized peptide antigen (HA tag) or a human Fab, called e44 and characterized as binding the HCV protein E2 (Burioni R et al., 1998a), has been fused in frame with cp3* (FIG. 3). The resulting vectors pRIB1-HAcp3* and pRIB1-e44 cp3* (FIG. 4) have been then used to characterize the cp3* properties for phage display applications, as compared to the corresponding control phagemids pRIB1-cp3* and pRIB-e44.

The expression of the cp3*-based fusion proteins was verified by Western blot of total protein extract prepared with bacterial clones containing pRIB1-cp3*, pRIB1-HAcp3*, pRIB-e44 cp3 or pRIB1-e44 cp3* and analyzed with anti-HA tag (FIG. 5A) or anti-human Fab (FIG. 5B). The Western blots show that both HA tag and e44 fab are correctly expressed in bacteria as fusion protein with cp3* using pRIB1-cp3* vectors.

c) Conclusion

The cp3 protein sequence modified with the DIS linker2 (cp3*) can be cloned and expressed in a phagemid vector allowing the correct expression of cp3*-based fusion protein in bacteria.

Example 2

Preparation and Expression of a DIS Linker2-Modified DNA Sequence Encoding a Filamentous Phage Coat Protein 8 (cp8*) for Displaying Proteins and Peptides a) Materials & Methods Production of a Gene Encoding a DIS Linker2 N-Terminal Modified cp8 Protein (cp8* Protein), Related Vectors Expressing cp8*-Based Fusion Proteins, and their Analysis The production of cp8* starting from a commercially available bacteriophage M13 helper and the cloning strategy are identical to those indicated in Example 1 for cp3*. The PCR was carried out using the primers cp8*FW and cp8*RW (SEQ ID NO.: 15 and SEQ ID NO.: 16; Table I). The PCR conditions used were: 95° C. for 2 min (1 cycle); 95° C. for 20 sec, 63° C. for 30 sec, 72° C. for 40 sec (35 cycles). The PCR amplification was carried out using Expand High Fidelity (Roche) according to the manual instructions. The DNA template (obtained from VCSM13) and the primers concentration used were the same described for the cp3* PCR amplification. After the PCR amplification, 2.5 units of AmpliTaq polymerase were added and the reaction was incubated for further 20 minutes at 72° C. The PCR product was electrophoresed in a 1.5% agarose gel and purified using gene extraction kit (Qiagen).

The modified cp8* gene was then ligated into pGEM-T easy vector and clones were then analysed by restriction endonuclease enzymes and sequenced in order to verify the correct cp8* sequence.

The pRIB2-cp8* vector was constructed using a pRIB1-cp3* that was digested with SpeI-NheI and ligated with the cp8* derived from pGEM-T Easy excised with SpeI-NheI digestion. The ligation mixture was used to transform electrocompetent E. coli DH5alfa cells as indicated in Example 1. Consequently, also pRIB2-HAcp8* and pRIB2-e44 cp8* were generated starting from pRIB2-cp8*, and using the same cloning strategy described above for pRIB1-HAcp3* and pRIB1-e44 cp3*

The Western blot on whole cell extracts analysis for detecting HAcp8* and e44 cp8* was performed as described above for HAcp3* and e44 cp3* b) Results

The approach for modifying the N-terminus of cp8 with the DIS linker2 and to generate the related phagemid vectors was the same used for modifying cp3 (see example 1). This variant, containing amino acid 24-73 of Enterobacteria phage M13 cp8 protein (SWISSPROT Acc. No. P69541), lacks only the original signal sequence. The sequence of the M13 gene encoding cp8 was modified through PCR amplification (cp8*, 62 amino acids: FIG. 6A), generating a PCR product (FIG. 6B) that was then used to construct the pRIB2-cp8* vector and a series of vectors in which cp8*-based fusion protein containing HA tag (FIG. 7) or human Fab e44 have been cloned.

Similarly to cp3*-based fusion proteins, the expression of the cp8*-based fusion proteins was verified by Western blot of total protein extract prepared with bacterial clones containing, pRIB2-HAcp8*, pRIB2-e44 cp8*, or without any phagemid vector, and analyzed with anti-HA tag (FIG. 8A) or anti-human Fab antibodies (FIG. 8B). The Western blots show that both HA tag and e44 Fab are correctly expressed in bacteria as fusion protein with cp8* using pRIB2-cp8* vectors.

c) Conclusions

The cp8 protein sequence modified with the DIS linker2 (cp8*) can be cloned and expressed in a phagemid vector allowing the correct expression of cp8*-based fusion protein in bacteria.

Example 3

Functional Validation of Phage Displaying Cp3* or Cp8* Fused to a Peptide or an Antibody a) Materials & Methods Amplification of the Phagemids The following methods were performed as described in the literature ("Molecular Cloning: A Laboratory Manual", Sambrook et al., Cold Spring Harbor Press, NY, 1989). Electrocompetent E. coli XL1-Blue cells were electroporated (0.2 cm E. coli Pulser cuvette, 2.5 Kv) with 50 ng of the phagemid vector (pRIB1-cp3, pRIB-HAcp3, pRIB-e44 cp3, pRIB1-cp3*, pRIB1-HAcp3*, pRIB1-e44 cp3*, pRIB2-cp8*, pRIB2-HAcp8*, or pRIB2-e44 cp8*).

Each cuvette was flushed immediately with 1 ml and then with 2 ml of SOC medium (Sodium chloride 0.5 g/L, Tryptone 20.0 g/L, Yeast extract 5.0 g/L, KCl 2.5 mMol, pH adjusted to 7.0 with NaOH: after autoclaving, 5 ml of a 2 M MgCl2 sterile solution and 20 ml of a 1 M sterile glucose solution for 1 liter of medium are added just before use) at room temperature. The 3 ml culture was transferred into a 50 ml polypropylene tube and shaken at 250 rpm for 1 hour at 37° C. 1 µl and 10 µl from each culture were withdrawn to calculate the transformation efficiency: they were plated on LB agar plate added with Ampicillin (Amp; 100 µg/ml) and Tetracyclin (Tet; 10 µg/ml) and the plated were incubated at 37° C. overnight. The remaining content of each tube was transferred into a bottle containing 20 ml of SB added with 4 µl of low-concentration Amp (20 µg/ml) and 40 µl of Tet (10 µg/ml) and was incubated and shaken at 250 rpm for 1 hour at 37° C. Each culture was brought up to 100 ml with SB+50 µl of high-concentration Amp (50 µg/ml)+200 µl of Tet (10 µg/ml) and incubated for another hour at 37° C.

Helper Phage Superinfection

VCSM13 Helper phage (Stratagene, $10^{12}$ plaque-forming units [pfu]) was added to each liquid culture that was further incubated for 2 hours at 37° C. at 250 rpm. Kanamicin (70 µg/ml) was added and the cultures were incubated and shaken overnight at 250 rpm at 30° C.

Polyethylene Glycol (PEG)-Mediated Phage Precipitation 50 ml of bacteria from each culture were pelleted by centrifugation at 4000 rpm (2700 g) in a JA10 rotor (Beckman) for 30 minutes at 4° C. Each supernatant was transferred to a clean tube containing 10 ml of 20% PEG (polyethylene glycol, wt 8000; Sigma)/2.5M NaCl solution. The solution was mixed thoroughly by inverting the tube gently 3-4 times. The mixtures were then incubated for at least 30 minutes on ice. Each phage sample was pelleted by centrifuging at 15000 rpm for 40 minutes at 4° C. The supernatant was discarded, being careful not to disturb the pellet. The residual supernatant was removed by aspirating with a 1 ml pipettor. The pellet was resuspended in 1 ml of 1% BSA/PBS (1 g of bovine serum albumin dissolved into 100 ml PBS and pH adjusted to pH 7.4) and it was transferred to 1.5 ml tube.

XL-1Blue Cells Infection with Resuspended Phage

One colony of E. coli XL1-Blue was inoculated into a 100 ml bottle containing 30 ml of SB added with Tet (10 µg/ml) and the culture was incubated at 37° C. 2 ml from the bacterial culture at the mid-log phase ($OD_{600}=\approx0.6$) were infected with 1 µl of each phage (1:100 diluted) (iii) and the cells were incubated and shaken for 20 minutes at 37° C. Each infected culture was brought up to 10 ml (ii) with SB and it was 1:1000 diluted (i). 10 µl and 100 µl from each culture were plated on LB agar plates added with Amp (100 µg/ml) and Tet (10 µg/ml). The plates were incubated overnight at 37° C.

Phage CFU Determination

When the colonies were of optimal size (clearly visible on the plate), they were counted and the cfu/µl was calculated using the formula (I):

(Counted colonies/plated volume)×$10^3$(i)×$10^4$(ii)×$10^2$(iii).

Phage-antigen Binding Assay

Series of two wells into a 96-well high binding capacity ELISA plate (Costar) were coated with 0.3 µg of different test proteins: a commercial murine anti-HA tag monoclonal antibody (HA.11, Covance; dissolved in 25 µl of PBS), or recombinant E2 protein prepared as described in literature (Lesniewski et al., 1995) dissolved in ECB buffer, (Env Coating Buffer, 0.1 M sodium bicarbonate, pH 8.6). The wells for the negative controls were prepared by adding 50 µl of 1% BSA/PBS. The plate was incubated overnight at 4° C. The coating reaction was blocked by adding 180 µl of 1% BSA/PBS and was incubated at 37° C. for 2 hours. The BSA/PBS solution was aspirated from each well of the ELISA plate and 70 µl of the resuspended phage (generated using the protocol provided above for the phagemid vectors pRIB1-HAcp3*, pRIB1-e44 cp3*, pRIB2-e44 cp8*, pRib2-HAcp8*) was added to each well and the plate was incubated for 2 hours at 37° C. The content of the wells was aspirated and transferred to separate tubes (named as INPUT) and stored at 4° C. The plate was washed 10 times with PBS/Tween-20 (PBS containing 0.5% (v/v) Tween-20, Sigma) prewarmed at 56° C. Each well was then eluted with 50 µl of panning elution buffer (0.1M HCl pH 2.2). The content of both wells with the same antigen was mixed (named as OUTPUT) and transferred into a clean tube containing 12 µl of panning neutralization buffer (1M Tris base, pH 9.1).

The set of samples were collected:
Set 1:
OUTPUT pRIB1-HAcp3* against anti-HA
OUTPUT pRIB2-HAcp8* against anti-HA
OUTPUT pRIB1-HAcp3* against BSA
OUTPUT pRIB2-HAcp8* against BSA
OUTPUT pRIB1-HAcp3* against E2
OUTPUT pRIB2-HAcp8* against E2
Set 2:
OUTPUT pRIB1-e44 cp3* against E2
OUTPUT pRIB-e44 cp3 against E2
OUTPUT pRIB1-e44 cp3* against BSA
OUTPUT pRIB-e44 cp3 against BSA
Set 3:
OUTPUT pRIB-e44 cp3 against E2
OUTPUT pRIB2-e44 cp8* against E2
OUTPUT pRIB-e44 cp3 against BSA
OUTPUT pRIB2-e44 cp8* against BSA OUTPUT and INPUT phage were quantified using 2 ml from the bacterial culture at the mid-log phase ($OD_{600}=\approx0.6$), that were infected by the INPUT and OUTPUT phage described above. The infected cells were incubated and shaken for 20 minutes at 37° C. The cells were infected with all the output and 1 µl of INPUT (1:100 diluted) (iii). Each infected culture was brought up to 10 ml (ii) with SB and the following volumes from each culture were plated on LB agar plates added with Amp (100 µg/ml) and Tet (10 µg/ml): 10 µl and 100 µl of INPUT infected culture 1:1000 diluted (i) 1 µl and 10 µl of OUTPUT infected culture not diluted. The plates were incubated overnight at 37° C.

When the colonies were of optimal size, they were counted and the phage cfu/µl was calculated using the following formula (II) for INPUT phage:

(Counted colonies/plated volume)×$10^3$(i)×$10^4$(ii)×$10^2$(iii)

The colonies of optimal size for OUTPUT phage were counted and the phage cfu/µl was calculated using the following formula (III):

(Counted colonies/plated volume)×$10^4$(ii)

b) Results

A comparative analysis of the efficiency by which recombinant phage expressing cp3*- or cp8*-based fusion proteins infect cells and display the heterologous protein was performed.

The electroporation efficiency was the same for both the transformation reactions (using the corresponding positive control, cp3-based vector) in all the experiments. The cfu/µl values obtained with pRIB1-cp3*, pRIB1-HAcp3*, and pRIB1-e44 cp3* vectors were the same of the positive control phage, demonstrating that the sequence modification in cp3* did not affect the correct phage assembly, leading to the correct expression of the phage proteins (FIG. 9). This evidence was confirmed also for pRIB2-based vectors (FIG. 10).

A more functional assay was performed for assessing enrichment and selection when panning the cp3*- or cp8*-based phage against a specific binding agent (such as an antibody or a viral protein) immobilized on an ELISA plate.

A high enrichment in pRIB1-HAcp3* and pRIB2-HAcp8* phage was obtained using a commercial monoclonal antibody against HA tag with respect to the negative control proteins (BSA; E2 protein of HCV), demonstrating that phage having HA tag fused to cp3* or cp8* were correctly displaying the peptide and can be efficiently selected against a specific binding agent (FIG. 11).

A similar level of enrichment in pRIB2-e44 cp3* or pRIB1-e44 cp8* phage was obtained using the E2 protein of HCV (the antigen specifically recognized by e44 Fab). confirming again that phage were correctly displaying the antibody and could efficiently selected against the correct antigen (FIG. 12). When compared to a control antigen (BSA), the phage expressing e44 cp3* shown a selectivity against the specific antigen comparable to that of phage expressing e44 cp3, while e44 cp8* was less efficient, provably due the known non-specific binding effects observed for other fabs expressed on the high valency cp8 protein.

c) Conclusions

The cp3*- and cp8*-expressing phagemid vectors can be used for displaying proteins and identifying specific binding agents, including peptides and antibody fragments, on the surface of recombinant phage.

Example 4

Construction of pDD-cp3*cp8* and of DD Cassettes Compatible with pDD-cp3*cp8* a) Materials & Methods

Construction of pDD-cp3*cp8* Backbone

Figure 13:
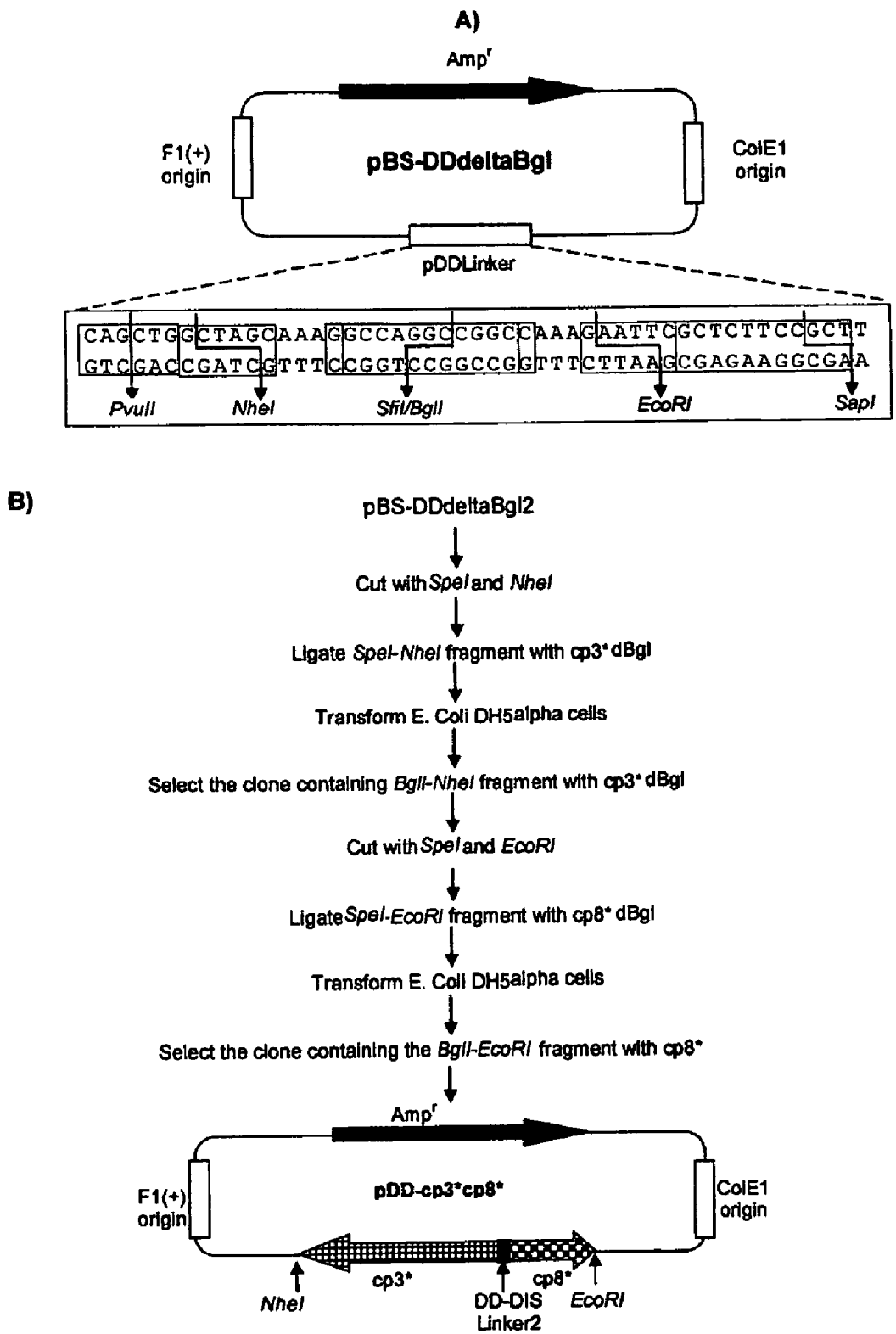
FIG. 13: (A) Structure of the pBS-DDdeltaBgl phagemid vector in which a pDD linker (SEQ ID NO: 49), comprising the restriction sites needed for further manipulation, has been cloned. (B) Flowchart showing the cloning strategy for modifying pBS-DDlinker2 (derived from pBS-DDdeltaBgl) into pDD-cp3*cp8*, that is schematically represented. The DD-DIS linker2 is across the 5' ends of the DNA encoding the two modified coat protein sequences cloned in the opposite directions.

Even though SfiI may cut with low efficiency its single site in DIS linker2, a vector can be also linearized with another restriction enzyme named BglI that recognizes the same SfiI core sequence (GCCnnnnnGGC (SEQ ID NO: 56); see FIG. 13A).

However, since two other BglI sites are already present in the pBlueScript II (SK+), the original sequence of the pBlueScript II (SK+) was modified in two rounds of site-directed mutagenesis using 2 set of primers, named Mut BglIA FW and RW (SEQ ID NO.: 28 and SEQ ID NO.: 29; Table I) and Mut BglIB FW and RW (SEQ ID NO.: 30 and SEQ ID NO.: 31; Table I), in order to remove two BglI sites present in the original DNA sequence. The resulting vector (pBS-deltaBglI) was modified by deleting a 0.5 kb fragment containing the MCS and LacZ sequence comprised between the PvuII and SapI restriction sites and by ligating between these sites a synthetic linker obtained by annealing two oligonucleotides (pDD linker FW and pDD linker RW; SEQ ID NO.: 32 and SEQ ID NO.: 33; Table I) carrying compatible ends (blunt at one side, with a single stranded 5' end having the sequence AGC at the other side). After overnight incubation at 4° C., 10 μl of the ligation mixture were used for transforming E. Coli XL-1 Blue competent cells. The day after, 10 colonies were picked up and used for mini prep DNA extraction in order to verify the presence of the synthetic linker. One clone showing the right restriction pattern was chosen, sequenced, and named pBS-DddeltaBgl.

This plasmid was used for the production of pDD-cp3*cp8* backbone. At this scope pBS-DDdeltaBgl was digested with EcoRI and NheI and ligated with a synthetic linker named pDD Linker2 (SEQ ID NO.: 34) carrying relevant restriction sites (SpeI, in particular) and compatible ends. The synthetic pDD Linker2 was generated by PCR amplification of pBlueScript II using primers pDD Linker2 FW and RW (SEQ ID NO.: 35 and SEQ ID NO.: 36; Table I). After PCR amplification, pDD Linker2 was digested with EcoRI and NheI and cloned into pBS-DDdeltaBgl. The ligation mixture obtained was incubated overnight at 4° C. and then used to transform E. Coli XL-1 Blue cells. The day after, 10 colonies were picked up and used for mini-prep DNA extraction in order to verify the correct insertion of pDD Linker2 carrying the SpeI site.

Such plasmid (called pBS-DDdeltaBgl2) was used for generating pDD-cp3*cp8* using DNA sequences encoding cp3* and cp8* that have been obtained from pRIB1-cp3* and pRIB2-cp8* but that were previously modified by site-directed mutagenesis for eliminating unwanted restriction sites. In fact, the DIS linker2 originally present in these sequences contains a BglI restriction site in addition to the one comprised in the SfiI site, without changing the encoded amino acid (a glycine). The C to A substitution (in position 27 of DIS linker2, SEQ ID NO.: 2) was removed in cp3* and cp8* using the primers deltaBglIlinker FW and RW (SEQ ID NO.: 37 and SEQ ID NO.: 38; Table I) generating the DNA encoding cp3* and cp8* now called cp3*dBgl (SEQ ID NO.: 39) and cp8*dBgl (SEQ ID NO.: 40). In addition, an EcoRI was inserted in 5' to cp8*dbgl using the primers cp8* FW new and cp8* RW (SEQ ID NO.: 39 and SEQ ID NO.: 40; Table 1).

The pBS-DDdeltaBgl2 plasmid was digested first with SpeI and NheI and then ligated with cp3*dBgII fragment carrying compatible ends. The ligation mixture obtained was incubated overnight at 4° C. and then used to transform E. Coli DH5alpha cells. The day after, 10 colonies were picked up and used for mini-prep DNA extraction in order to verify the correct insertion of cp3*dBgl. The plasmid that was extracted from one positive clone was then digested with EcoRI and SpeI and ligated with a cp8*dBgII fragment carrying compatible ends. The day after, 10 colonies were picked up and used for mini-prep DNA extraction in order to verify the correct insertion of cp8*dBgl, leading to pDD-cp3*cp8*.

Construction of DD Cassette Expressing CAT (DDa Cassette)

The vector pRIB1-HAcp3* was first modified in order to insert a BglI site in 5' to the ScaI and XbaI cloning site by a round of site-directed mutagenesis using the Bglup FW and RW (SEQ ID NO.: 43 and SEQ ID NO.: 44). The resulting plasmid, named pRIB1-DDa, was digested with BglI and the fragment carrying this cassette (SEQ ID NO.: 11) was ligated into pDD-cp3*cp8* digested with BglI. The ligation mixture obtained was incubated overnight at 4° C. and then used to transform E. Coli DH5alpha cells that were grown on LB agar plates added with Cloramphenicol (20 μg/ml). The day after, 10 colonies were picked up randomly and used for mini-prep DNA extraction in order to verify the insertion of the DDa cassette in either one or the other direction by NheI and XbaI digestion, and consequently the vectors pDDa-cp3* and pDDa-cp8* expressing CAT resistance.

Construction of DD Cassette Expressing the Resistance to Zeocin (ZEO; DDb Cassette)

The Zeocin resistance gene was PCR amplified using primer Zeo FW and RW (SEQ ID NO.: 45 and SEQ ID NO.: 46; Table I) from pSVZeo plasmid (Invitrogen). The PCR fragment was cloned into pGEMTeasy. Because a BglI site was present in the gene a round of site-directed mutagenesisis was performed using primer ZeodeltaBgl FW and RW (SEQ ID NO.: 47 and SEQ ID NO.: 48; Table I). The modified ZEO gene was then digested with StuI and XbaI and cloned in the corresponding site of pDDa-cp3*, obtaining pDDb-cp3*. The corresponding pDDb-cp8* vector was obtained by digesting pDDb-cp3* with BglI and relegating the two fragments. Clones having the BglI fragment corresponding to DDb cassette in one or the other direction were identified by NheI and XbaI digestion of the plasmid DNA extracted from randomly chosen colonies. The clones containing the plasmids pDDb-cp3* and pDDb-cp8* were selected in the usual medium for bacterial cells added with Zeocin (10 μg/ml).

Site-directed mutagenesis was performed in all the constructions using a commercial kit (QuickChange Site-Directed mutagenesis kit: Stratagene #200518). These primers introduce single nucleotide substitutions in the relevant sites that can be easily checked by enzymatic digestion or sequencing and that do not alter other features of the vector. Other technologies for plasmid DNA extraction and digestion, DNA fragment purification and ligation, and cell transformation were performed as described in the literature.

The plasmid DNA extractions were performed using a miniprep kit (Qiagen) The ligation mixture have been used to transform electrocompetent E. Coli DH5alfa cells, in order to have enough colonies to pick and characterize.

b) Results

The previous examples above show that the modification in the sequence of two functional coat proteins due to the insertion of a DIS linker (DIS linker2, in particular) still provide fully functional coat proteins. The sequences coding for cp3* and cp8* can be assembled into a phagemid vector of the invention (pDD) according to the strategy summarized in FIG. 13.

The basic vector pDD-cp3*cp8* was generated by modifying pBlueScript II (SK+) vector and introducing synthetic linkers that allow the sequential cloning of cp3* and cp8* positioned in opposite direction and having their 5' ends separated by a DD-DIS linker (DD-DIS linker2). Specific restriction sites were added or deleted during the construction to make the cloning process effective.

The vector pDD-cp3*cp8* (FIG. 13) is a backbone vector for proceeding to the bidirectional cloning of a protein sequence to be displayed as a fusion protein with either cp3* (becoming a plasmid conceptually identical to pRIB1 series of vectors) or cp8*(becoming a plasmid conceptually identical to pRIB2 series of vectors), depending in which direction a DD cassette having 5' and 3' ends compatible with the BglI-linearized vector and possibly including other elements.

This plasmid represent a backbone into which a DD cassette can be inserted for expressing a protein either as a cp3*- or a cp8*-containing fusion protein. The DD cassette can be formed by combining different type of sequences in an asymmetric manner (FIG. 14), so that one end of the cassette, provided with the full DIS linker, can mediate the fusion and the transcription of a sequence in frame with one of the two functional coat proteins in the pDD backbone. The rest of the sequence can provide other functions not depending on the orientation in which the DD cassette is inserted.

The basic vector pDD-cp3*cp8* (and in general any vector presenting the same assembly of functional coat proteins coding sequences separated by a DD-DIS linker shown in FIGS. 14, 15, and 16) can be further modified by inserting a stuffer DNA or a marker gene, so that the insertion of the DD cassette can be associated to the deletion or addition of a marker gene, facilitating the selection of clones in which the DD cassette is inserted (FIG. 15).

Two types of DD cassettes, called DDa and DDb cassette (FIGS. 17 and 18) were produced starting from pRIB1-HAcp3', inserting a BglI site and maintaining HA as a stuffer DNA in the position nearby the DIS linker that will be used for cloning the protein sequence to be displayed. The two cassette differ for the marker gene positioned between the 5' end of the promoter used for transcribing the fusion protein and a couple of restriction sites that are used to clone any other sequence of interest (e.g. a variable region of a light chain when expressing a fab) in the DD cassette. This marker gene (CAT or ZEO) can be cloned in the DD cassette with the same orientation of the other transcription units in the DD cassette (i.e. pointing to the end of the DD cassette where the DIS linker is formed for expressing the fusion protein) or may have the opposite orientation (with advantage to avoid read-through transcriptional activities from the other promoters).

Figure 19:
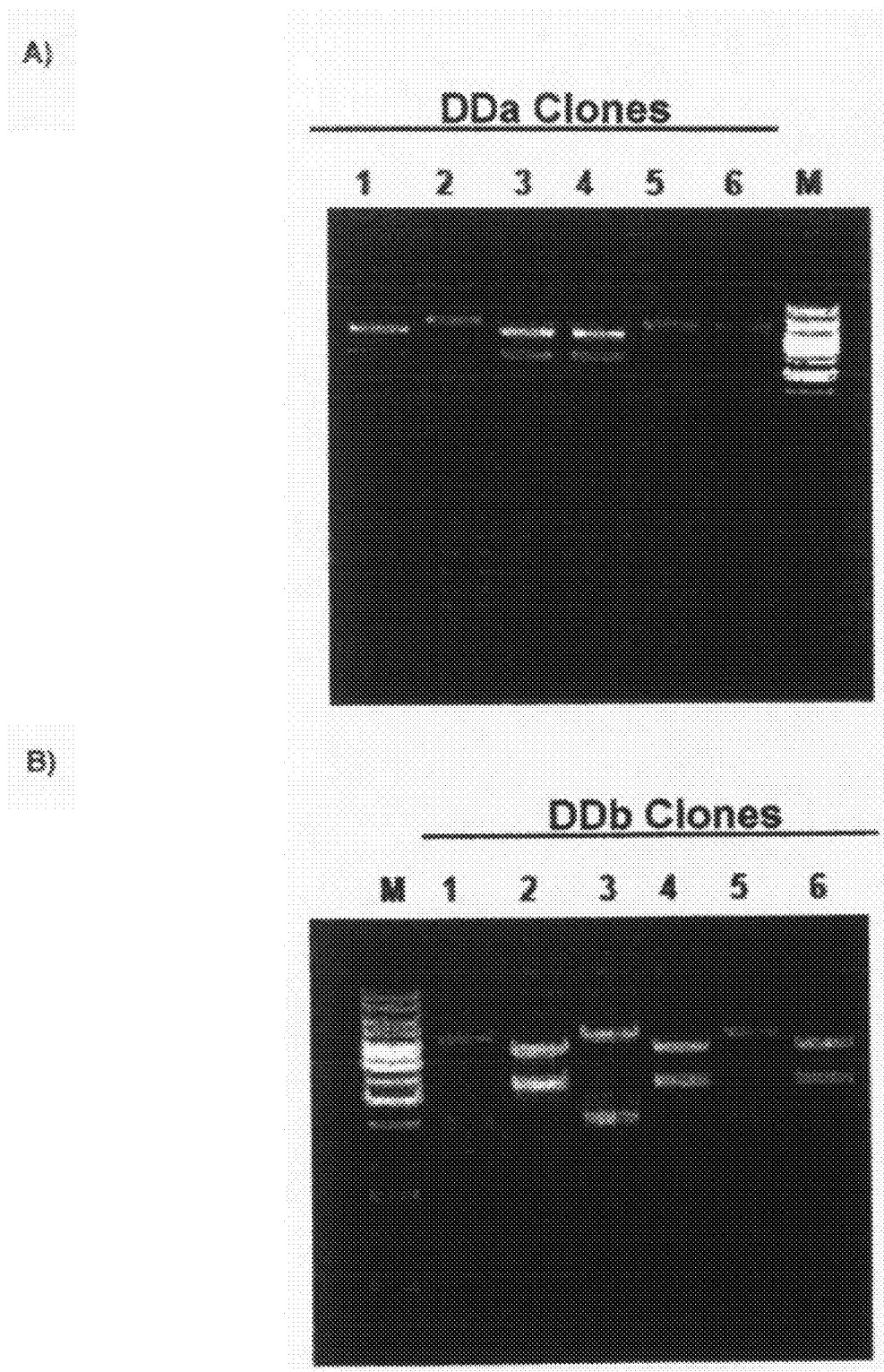
FIG. 19: restriction analysis of randomly selected pDD-cp3*cp8* clones in which the DDa (A) or DDb (B) cassette has been cloned using BglI restriction sites and digested with NheI (cutting at the 3' end of cp3* in the vector) and XbaI (positioned near the BglI restriction site not linked to the functional coat protein) in the DDa and DDb cassettes. Compared to a DNA marker (M), the plasmid DNA extracted from the clones in which the cassette is inserted in-frame with cp3* presents two fragments having more similar length (clones 1, 3, and 4 in panel A; clones 2, 4, and 6 in panel B) than those in which the cassette is inserted in-frame with the shorter cp8* sequence (clones 2, 5, and 6 in panel A; clones 1, 3, and 5 in panel B). This is due to the larger dimension of the cp3* sequence compared to cp*8.

When the DDa cassette and the DDb cassette are cut out from the pDD vector using the restriction site limiting the cassette (i.e. BglI) and the DD cassette is relegated in a pDD vector cut with the same enzyme, the DD cassette is inserted in one of the two possible orientation in each clone transformed with the ligation mixture, as the digestion with a combination of two enzymes, one cutting within the cassette and the other within the backbone (FIG. 19). This result shows also how the insertion events can be analyzed without sequencing the vectors and how the clones may be also grouped before o during the screening procedures.

The DDa and DDb cassettes can be used for constructing a library when they are cloned in pDD or in any other vector. However, the digestion with BglI and the ligation with a pDD vector having compatible ends is instrumental for having the library with the desired features.

Conclusions

The pDD vectors and the compatible DD cassettes can be generated by the series of cloning steps that can be easily followed by sequencing and/or digesting the pDD-based intermediate vectors from clones using plasmid DNA extraction/purification methods.

Once these pDD vectors and DD cassettes are generated, they can be used for generating libraries of sequences that are cloned in one or the other of the possible orientations. For example, a Fab library generated in this way should contain alternative recombinant phage in which the heavy chain fragment is produced and displayed as a fusion protein with either cp3* or cp8*. The same applies for the HA tag peptide or other peptides derived from an antigen.

The vectors outlined above can be efficiently used for the construction and the double display of antibody fragments, peptides or other proteins linked to either one of two coat proteins on the phage surface, allowing the simultaneous screening of sequences displayed in the two forms without a double cloning, transformation, and infection procedure.

The approach of the present invention increases the possibilities of cloning antibodies or other protein sequences whose expression and/or display efficiency is dependent from the context of the fused coat protein. Moreover, the use of different combinations of selection system (specific for the "empty" and the DD cassette containing phagemid vectors) facilitates the identification of clones having the correct structure and sequence.

Example 5

Functional Validation of pDD-Based Recombinant Phage Displaying cp3* or cp8* Fused to a Peptide or an Antibody a) Materials & Methods The amplification of the phagemids, helper phage superinfection, polyethylene glycol (PEG)-mediated phage precipitation, XL-1Blue cells infection with resuspended phage, phage CFU determination, phage-antigen binding assay, and the calculation of phage cfu/µl were performed as described in F.1 and in the literature ("Molecular Cloning: A Laboratory Manual", Sambrook et al., Cold Spring Harbor Press, NY, 1989).

Regarding the condition for cell selection, Tet is used as described above while Ampicillin is substituted with chloramphenicol (Caf; 20 µg/ml and 100 µg/ml) in the experiments including pDDa derivatives and with Zeocin (Zeo; 10 µg/ml and 50 µg/ml) in the experiments including pDDb derivatives.

Electrocompetent E. coli XL1-Blue cells were electroporated (0.2 cm E. coli Pulser cuvette, 2.5 Kv) with 50 ng of the phagemid vector (pRB32, pRIB1-HAcp3*, pRIB2-HAcp8*, pRIB1-e44 cp3*, pRIB2-e44 cp8*, pDDa-HAcp3*, pDDa-HAcp8*, pDDa-e44 cp3*, pDDa-e44 cp8*, pDDb-HAcp3*, pDDb-HAcp8*, pDDb-e44 cp3*, pDDb-e44 cp8*).

The following sets of samples were collected:
Set 1:
OUTPUT pDDa-HAcp3* against anti-HA
OUTPUT pDDa-HAcp3* against BSA
OUTPUT pDDa-HAcp8* against anti-HA
OUTPUT pDDa-HAcp8* against BSA
OUTPUT pRIB1-HAcp3* against anti-HA
OUTPUT pRIB1-HAcp3* against BSA
OUTPUT pRIB2-HAcp8* against anti-HA
OUTPUT pRIB2-HAcp8* against BSA
OUTPUT pRB32 against anti-HA
OUTPUT pRB32 against BSA
Set 2:
OUTPUT pDDa-e44 cp3* against E2
OUTPUT pDDa-e44 cp3* against BSA
OUTPUT pDDa-e44 cp8* against E2
OUTPUT pDDa-e44 cp8* against BSA
OUTPUT pRIB1-e44 cp3* against E2
OUTPUT pRIB1-e44 cp3* against BSA
OUTPUT pRB32 against E2
OUTPUT pRB32 against BSA
Set 3:
OUTPUT pDDa-HAcp3* against anti-HA
OUTPUT pDDa-HAcp3* against BSA
OUTPUT pDDb-HAcp3* against anti-HA
OUTPUT pDDb-HAcp3* against BSA
OUTPUT pRIB1-HAcp3* against anti-HA
OUTPUT pRIB1-HAcp3* against BSA
OUTPUT pDDa-HAcp8* against anti-HA
OUTPUT pDDa-HAcp8* against BSA
OUTPUT pDDb-HAcp8* against anti-HA
OUTPUT pDDb-HAcp8* against BSA
OUTPUT pRIB2-HAcp8* against anti-HA
OUTPUT pRIB2-HAcp8* against BSA
Set 4:
OUTPUT pDDa-e44 cp3* against E2
OUTPUT pDDa-e44 cp3* against BSA
OUTPUT pDDb-e44 cp3* against E2
OUTPUT pDDb-e44 cp3* against BSA
OUTPUT pRIB1-e44 cp3* against E2
OUTPUT pRIB1-e44 cp3* against BSA
OUTPUT pDDa-e44 cp8* against E2
OUTPUT pDDa-e44 cp8* against BSA
OUTPUT pDDb-e44 cp8* against E2
OUTPUT pDDb-e44 cp8* against BSA
OUTPUT pRIB2-e44 cp8* against E2
OUTPUT pRIB2-e44 cp8* against BSA b) Results Recombinant phage based on pDD and expressing cp3*- or cp8*-based fusion proteins were analyzed following the same approach by which pRIB1- and pRIB2-based recombinant phage were functionally compared.

A first set of experiments was intended to verify first that the combination of pDD-cp3*cp8* with a DD cassette expressing a CAF selection marker (pDDa-type phagemids) allows the correct expression and selection of peptides and fabs on either cp3* or cp8* (FIG. 20). Then, a second set of experiments was intended to verify that the combination of pDD-cp3*cp8* with a DD cassette expressing either a CAF (pDDa-type phagemids) or ZEO (pDDb-type phagemids) selection marker allows as well the correct expression and selection of peptides and fabs on either cp3* or cp8* (FIG. 22).

The electroporation efficiency was the same for both the transformation reactions (using the corresponding positive control, cp3-based vector) in all the experiments. The cfu/µl values obtained with pRIB1-based, pRIB2-based, pDDa-based, and pDDb-based vectors were similar (about $10^8$-$10^9$), demonstrating that the modification introduced into cp3 and cp8 using the intermediate phagemids pRIB1 and pRIB2 are not affecting as well the correct phage assembly when pDD-based phagemids containing either the ZEO or CAT selection marker are generated.

A high enrichment in specific pDD-based recombinant phage is obtained, again without any relevant difference between phagemids including the CAF- or the ZEO-based DD cassette, when using a protein or an antibody as target for such phage. This property is reproducibly found in pDD phagemids expressing a peptide using either cp3* or cp8*, while it is significantly lower only when cp8* is used for pDD phagemids expressing an highly specific Fab, still confirming the results obtained in the literature and for pRIB1 and pRIB2 phagemids described above.

c) Conclusions

The pDD-cp3*cp8* phagemid can be combined with a DD cassette comprising either CAF or ZEO as selection marker for expressing and selecting protein sequences in the form of either cp3*- or cp8*-based fusion proteins on the surface of recombinant phage.

Example 6

Construction of pDD-Compatible Vectors for Expressing Sequences Selected Using a pDD-Based Library a) Materials & Methods A cDNA library from human bone marrow was prepared and this library was used as template for PCR reaction in which the DNA encoding the variable region of the light and heavy chains of human IgG1 immunoglobulins were amplified according to the literature (Burioni et al., 1998a; "Phage Display: A laboratory Manual", Burton D R et al., CSHL Press, 2001).

The PCR primers were partially degenerated at the 3' end and contained the restriction sites needed for cloning them into DDb cassette at their 5' end. The amplification products specific for the light chains were first digested with XbaI and ScaI i and purified from agarose gel. Five micrograms of pDDb-HAcp3* were digested with XbaI and ScaI, and the resulting vector backbone was gel-purified, dephosphorilated, and used for the preparation of a ligation mixture with the compatible DNA segments encoding the light chain. After overnight incubation at 4° C., the DNA mixture was precipitated, resuspended in 20 microliters of water and used for transforming competent E. Coli XL1 Blue cells by electroporation. The cells were then incubated in 3 ml of SOC at 37° C. for 1 h. 10 and 100 µl of the culture were plated in order to quantify the number of the clones. The rest of the bacterial culture was then diluted to 10 ml of SB containing Ampicillin (10 µg/ml), (Zeocin 10 µg/ml), and Tetracycline (10 µg/ml). After 1 hour of incubation at 37° C., the cells were diluted in 100 ml of SB medium containing Ampicillin (50 µg/ml), Zeocin (50 µg/ml), and Tetracycline (10 µg/ml), and incubated over night at 37° C. The day after, the cells were harvested and used for DNA purification and extraction.

The resulting pDDb-based library carrying the light chains was digested with XhoI and SpeI and used for the insertion of the heavy chains recovered from the original amplification products that were previously digested with XhoI and SpeI and purified from agarose gel. The ligation reaction was used transforming competent *E. coli* XL1 Blue cells by electroporation as described above.

The resulting pDDb-based library carrying the light and heavy chains was then digested with BglI and the fragments were relegated in the same vector. Aliquots of the library were plated on LB agar with containing Ampicillin (50 µg/ml) and Zeocin (50 µg/ml). The number of clones in the library was evaluated in the order of $10^4$-$10^5$ clones. Colonies were randomly chosen from the plates, grown overnight in culture, and used for both miniprep DNA extraction/purification (followed by digestion with NheI and XbaI and analysis in agarose gel as described above) and for protein analysis in Western blot (using a goat anti-human Fab conjugated to horseradish peroxidise for detection, as described above).

Results

A DNA library derived from human bone marrow cells was used for the cloning of light and heavy chains from either IgG1 into a DDb cassette already cloned within a pDDb vector having HA tag as stuffer DNA between the XhoI-SpeI.

The DNA encoding the light and heavy chains was sequentially cloned in this vector, eliminating the stuffer DNA, and the resulting library was digested with BglI and religated at scope of reinsering the DDb cassette in either one of the two possible orientations, generating in this way a pDDb-based library in which the heavy chains are expressed as fusion protein with cp3* or cp8*.

Colonies of *E. coli* transfomants growing in presence of Zeocin (against which the cells are resistant due to the marker gene in the DDb cassette) were randomly chosen and analyzed at both DNA and protein level (FIG. 22). Such clones have the DDb cassette oriented in either one or the other of the possible orientations, as shown by the restriction analysis of the extracted plasmid DNA, and express human fabs a fusion proteins in which the heavy chain is linked to cp8* or to cp3*. The difference in the molecular weight and the level of expression are consistent with the outcome of the restriction analysis, since the clones having the DDb cassette oriented in the direction allowing the fusion of the heavy chain to cp8*, express smaller recombinant proteins that are produced at higher levels compared to the clones in which having the DDb cassette oriented in the direction allowing the fusion of the heavy chain to cp3*.

Conclusions

The DDb cassette has been used for generating a library of human fabs in which the heavy chains are expressed as either cp3*- or cp8*-containing fusion proteins. This library was achieved by a using a single library based on a pDD-based plasmid that was simply digested with a restriction site in the DIS linker and religated.

This basic process can be applied also for library of sequences that are cloned in a DD cassette within any type of plasmid and then transferred in a pDD-based vector as exemplified in the present example or in the other situation briefly summarized in FIG. 15.

Figure 23:
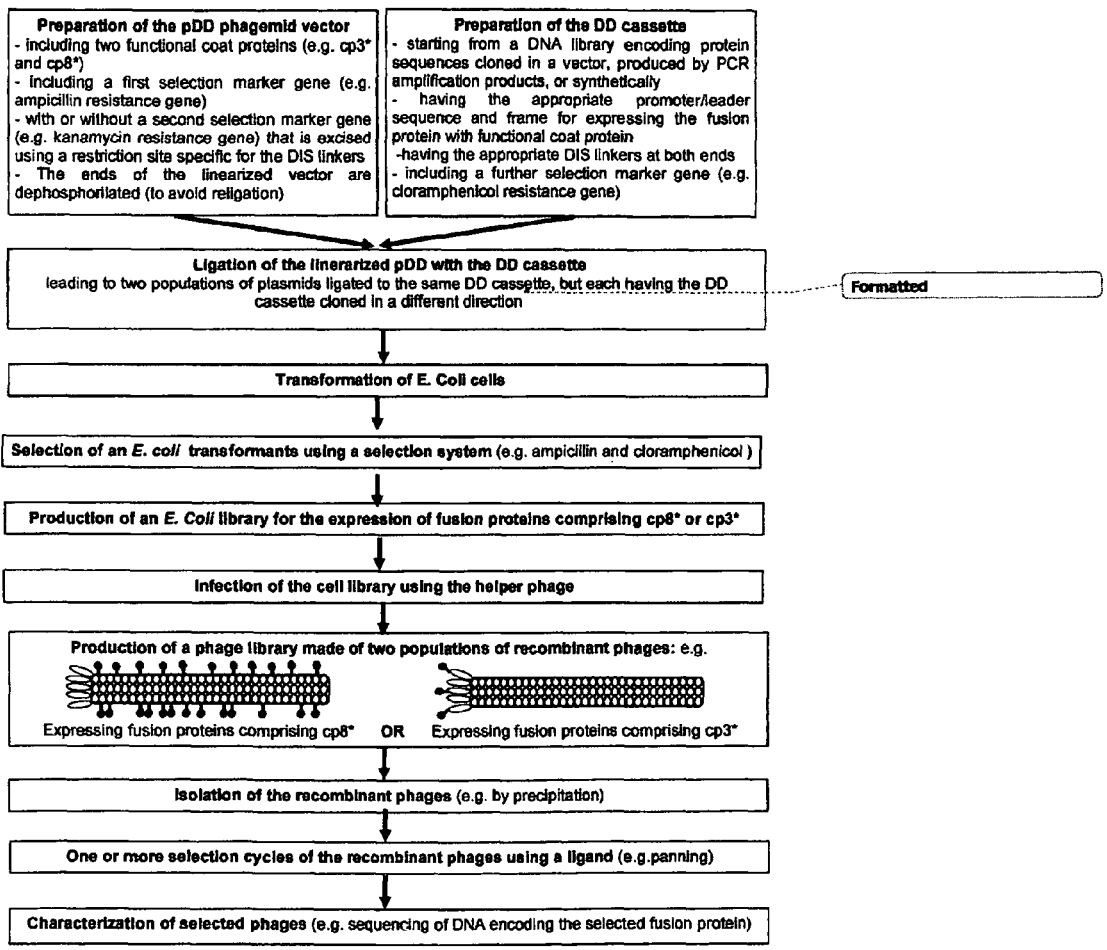
FIG. 23: Flow chart outlining the process for preparing libraries and selecting recombinant phage using the vectors of the invention.

The full process for identifying relevant sequences in a pDD-based system for vector by phage display and affinity-selection can be outlined (FIG. 23). Starting from the appropriate combination of pDD vector and of library of sequences to be analyzed that are cloned into a DD cassette, the ligation and transformation step provides a cell library, selectable by applying the correct antibiotic combination, that encode the two types of fusion proteins (e.g. comprising either cp3* or cp8*). Helper phage infection makes then possible to simultaneously produce a library of recombinant phage in which the proteins to be screened are expressed on two populations of phage mixed in the same library generated using a single pDD vector. This library can be then screened using the approaches reported in the literature in order to isolate, sequence, and characterize relevant proteins and peptides that are expressed and displayed as fusion proteins with either cp3* or cp8*.

TABLE I summary of the PCR primers and oligonucleotides

| Primer Name | SEQ ID NO.: | Primer Sequence |
|---|---|---|
| cp3*FW | 13 | GACAAAACTAGTGGCCAGGCCGGC CAGGGTGGCGGTGGCTCTCCA |
| cp3*RW | 14 | GTGGTGGCTAGCTTAAGACTCCT TATT |
| cp8*FW | 15 | ACTAGTGGCCAGGCCGGCCAGGGT GGCGGTGGCTCTGCTGAGGGTGAC GATCCCGCA |
| cp8*RW | 16 | GTGGTGGCTAGCTCAGCTTGCTTT CGAGGTGAATTT |
| HA tag Linker FW | 17 | TCGAGTATCCATATGATGTTCCAG ATTATGCTA |
| HA tag Linker FW | 18 | CTAGTAGCATAATCTGGAACATCA TATGGATAC |
| LCstuffer FW | 26 | CCAGATGACCCAGTCTCCTTCCAC CCT |
| LCstuffer RW | 27 | CTAGAGGGTGGAAGGAGACTGGGT CATCTGGAGCT |
| Mut BglI A FW | 28 | GCGCGTCCCATTCGACATTCAGGC TGCGC |
| Mut BglI A RW | 29 | GCGCAGCCTGAATGTCGAATGGGA CGCGC |
| Mut BglI B FW | 30 | TTCTGCGCTCGGCACTTCCGGCTG GCT |
| Mut BglI B RW | 31 | AGCCAGCCGGAAGTGCCGAGCGCA GAA |
| pDD Linker FW | 32 | CTGGCTAGCAAAGGCCAGGCCCGC CAAAGAATTCGCTCTTCC |
| pDD Linker RW | 33 | AGCGGAAGAGCGAATTCTTTGGCC GGCCTGGCCTTTGCTAGCCAG |
| pDD Linker2 FW | 35 | GCGCGTAATACGACTCACTATAGG GC |
| pDD Linker2 RW | 36 | CAGCTGGCTAGCATGCTTCCGGCT CGTATGTTGTG |
| deltaBgllinker FW | 37 | CCGGCCAGGGTGGAGGTGGCTCT |
| deltaBgllinker RW | 38 | AGAGCCACCTCCACCCTGGCCGG |
| cp8*FW new | 41 | ATGTACTAGTGGCCAGGCCGGCCA GGG |
| cp8*RW new | 42 | GGAATCCTAGAATTCTCAGCTTGC TTTCGAGGTGAAT |
| BglupdFW | 43 | AATGAGTAGGCCTTGTTGACAATT AATCATCGGCATAGT |
| BglupdRW | 44 | AACTGGATCTAGACATGATAAGAT ACAACATTGATGAGTTTGG |
| Zeo FW | 45 | AATGAGTAGGCCTTGTTGACAATT AATCATCGGCATAGT |

TABLE I-continued summary of the PCR primers and oligonucleotides

| Primer Name | SEQ ID NO.: | Primer Sequence |
|---|---|---|
| Zeo RW | 46 | AACTGGATCTAGACATGATAAGAT ACATTGATGAGTTTGG |
| ZeodeltaBgl FW | 47 | GAGCAGCCGTGGGGACGGGAGTTC GCCC |
| ZeodeltaBgl RW | 48 | GGGCGAACTCCCGTCCCCACGGCT GCTC |

REFERENCES

Adda C et al., Infect Immun 67 (1999) 4679-88.
Al-bukhari T et al., J Immunol Methods 264 (2002) 163-71.
Ames R et al., J Immunol Methods 184 (1995) 177-86.
Baek, H et al., Nucleic Acids Res 30 (2002) e18.
Bai Y and Feng H, Eur J Biochem 271 (2004) 1609-14.
Bandmann N et al., J Biotechnol 93 (2002) 1-14.
Benhar I. Biotechnol Adv 19 (2001) 1-33.
Bhardwaj D et al., J Immunol Methods 179 (1995) 165-75.
Boel E et al., J Immunol Methods 239 (2000) 153-66.
Bonnycastle L e tal., Biol Chem 378 (1997) 509-15.
Bothmann H. and Pluckthun A, Nat Biotechnol 16 (1998) 376-80.
Bradbury, A. R. and Marks, J. D. J Immunol Methods 290 (2004) 29-49.
Bugli, F et al., J Virol 75 (2001) 9986-90.
Burioni R et al., Res Virol 148 (1997) 161-4.
Cebe R et al., Biochem J 352 Pt 3 (2000) 841-9.
Chen L et al., Chem Biol 11 (2004) 1081-91.
Conrad, U. and Scheller, J, Comb Chem High Throughput Screen 8 (2005) 117-26.
Corisdeo S, and Wang B, Protein Expr Purif 34 (2004) 270-9.
Davies J et al., J Allergy Clin Immunol 105 (2000) 1085-92.
De Berardinis P et al., Nat Biotechnol 18 (2000) 873-6.
Den, W et al., J Immunol Methods 222 (1999) 45-57.
Dente L et al., Gene 148 (1994) 7-13.
Di Niro, R et al., Biochem J 388 (2005) 889-94.
Ditzel H, Immunol Res 21 (2000) 185-93.
Dromey, J. et al., J Immunol 172 (2004) 4084-90.
Edwards B et al., J Immunol Methods 245 (2000) 67-78.
Elrick L et al. J Hepatol 42 (2005) 888-96.
Enshell-Seijffers, D et al., Nucleic Acids Res 29 (2001) E50-0.
Faix P et al., Biotechniques 36 (2004) 1018-22, 1024, 1026-9.
Falciani C et al., Chem Biol 12 (2005) 417-26.
Florea B et al., J Drug Target 11 (2003) 383-90.
Gao, C et al., Bioorg Med Chem 10 (2002) 4057-65.
Gao C et al., Proc Natl Acad Sci USA 96 (1999) 6025-30.
Gao, H et al., Gene 228 (1999) 51-9.
Gargir A et al., Biochim Biophys Acta 1569 (2002) 167-73.
Goletz S et al., J Mol Biol 315 (2002) 1087-97.
Grote A et al., Nucleic Acid Res 33)2005) W526-31.
Guttieri M et al., Hybrid Hybridomics 22 (2003) 135-45.
Han Z et al., Comb Chem High Throughput Screen 7 (2004) 55-62.
Heinis C et al., Protein Eng 14 (2001) 1043-52.
Held H and Sidhu S, J Mol Biol 340 (2004) 587-97.
Hennecke F et al., Protein Eng 11 (1998) 405-10.
Hoet R et al. Nat Biotechnol 23 (2005) 344-8.
Hufton et al., J Immunol Methods 231 (1999) 39-51.
Hust, M. and Dubel, S. Trends Biotechnol 22 (2004) 8-14.
Hust M. and Dubel, S, Methods Mol Biol 295 (2005) 71-96.
Iannolo G et al., J Mol Biol 248 (1995) 835-44.
Intasai N et al., Protein Expr Purif 32 (2003) 323-31.
Jacobsson K et al., Biol Proced Online 5 (2003) 123-135.
Jaye D et al. J Immunol Methods 295 (2004) 119-27.
Kirsch M et al., J Immunol Methods 301 (2005) 173-85.
Kramer R et al., Nucleic Acids Res 31 (2003) e59.
Kurokawa, M. S et al. Immunol Lett 80 (2002) 163-8.
Kwasnikowski P et al., J Immunol Methods 307 (2005) 135-43.
Lagerkvist A et al., Protein Sci 10 (2001) 1522-8.
Landon L and Deutscher S, J Cell Biochem 90 (2003) 509-17.
Legendre D and Fastrez J, Gene 290 (2002) 203-15.
Lesniewski, R et al., J Med Virol 45 (1995) 415-22.
Li, Y et al., Nat Biotechnol 23 (2005) 349-54.
Li, Z et al. J Mol Microbiol Biotechnol 6 (2003) 57-66.
Liang M et al., J Immunol Methods 247 (2001) 119-30.
Lou J et al., J Immunol Methods 253 (2001) 233-42.
Mahler S et al., Immunotechnology 3 (1997) 31-43.
Makowski, L. Gene 128 (1993) 5-11.
Malik, P. and Perham, R. N. Nucleic Acids Res 25 (1997) 915-6.
Mancini N et al., New Microbiol 27 (2004) 315-28.
Matsushita S et al., Eur J Immunol 31 (2001) 2395-402.
Meijer P et al., J Mol Biol 358 (2006) 764-72.
Morino K et al., J Immunol Methods 257 (2001) 175-84.
Mutuberria R et al., J Immunol Methods 287 (2004) 31-47.
Nakashima T et al., J Biosci Bioeng 90 (2000) 253-9.
Nakayama G et al., Immunotechnology 2 (1996) 197-207.
Nilsson J et al., Protein Expr Purif 11 (1997) 1-16
Nilsson M et al., Protein Eng 13 (2000) 519-26.
O'Connell, D et al., J Mol Biol 321 (2002) 49-56.
O'Connor K et al., J Immunol Methods 299 (2005) 21-35.
Pastor M et al., Biopolymers 76 (2004) 357-65.
Paus E et al., J Immunol Methods 283 (2003) 125-39.
Persic L et al., Gene 187 (1997) 9-18.
Petrenko, V. A. and Smith, G Vectors and Modes of Display. Taylor & Francis, 2004.
Petrenko V et al., Protein Eng 15 (2002) 943-50.
Pini A et al., Antimicrob Agents Chemother 49 (2005) 2665-72.
Pini A et al., Curr Protein Pept Sci 5 (2004) 487-96.
Ravn P et al., J Mol Biol 343 (2004) 985-96.
Rhyner C et al., Methods 32 (2004) 212-8.
Rodi D et al., J Mol Biol 322 (2002) 1039-52.
Rondot S et al., Nat Biotechnol 19 (2001) 75-8.
Rosander et al., J Microbiol Methods 51 (2002) 43-55.
Roth, T et al. J Mol Biol 322 (2002) 357-67.
Rousch M et al., Br J Pharmacol 125 (1998) 5-16.
Sblattero D and Bradbury A, Nat Biotechnol 18 (2000) 75-80.
Schooltink H and Rose-John S, CombChem High Throughput Screen 8 (2005)173-9.
Schoonbroodt S et al., Nucleic Acids Res 33 (2005) e81.
Sharon J et al., J Cell Biochem 96 (2005) 305-13.
Shukla G. and Krag D, J Drug Target 13 (2005) 7-18.
Sidhu, S. Biomol Eng 18 (2001) 57-63.
Sidhu S et al., Methods Enzymol 328 (2000) 333-63.
Silacci, M et al., Proteomics 5 (2005) 2340-50.
Smith J et al., Faseb J 19 (2005) 331-41.
Soltes G et al., J Immunol Methods 274 (2003) 233-44.
Steukers M et al., J Immunol Methods (2006).
Stratmann, T. and Kang, A. S. Proteome Sci 3 (2005)7.
Strobel H et al., Mol Biotechnol 24 (2003) 1-10.
Suzuki Y et al., Biosci Biotechnol Biochem 69 (2005) 610-9.

Szardenings, M, J Recept Signal Transduct Res 23 (2003) 307-49.
Tsurushita, N et al., Gene 172 (1996) 59-63.
van de Westerlo E et al., Blood 99 (2002) 2427-33.
van Zonneveld, A et al., Gene 167 (1995) 49-52.
Vanhercke T et al., J Biomol Screen 10 (2005) 108-17.
Verhaert R et al., Biochem J 342 (Pt 2) (1999) 415-22.
Wang L et al., Mol Immunol 34 (1997) 609-18.
Watanabe H et al., Biochem Biophys Res Commun 295 (2002) 31-6.
Weiss G et al., J Mol Biol 332 (2003) 777-82.
Weiss G and Sidhu S, J Mol Biol 300 (2000) 213-9.
Weiss G et al. Protein Sci 9 (2000) 647-54.
Yip Y et al., Immunol Lett 79 (2001) 197-202.
Zelenetz, A. D. and Levy, R. Gene 89 (1990) 123-7.
Zhao Y et al., J Immunol 167 (2001) 2130-41.
Zhong G et al., J Ind Microbiol Biotechnol 19 (1997) 71-6.
Zwick M et al., Anal Biochem 264 (1998) 87-97.

The invention claimed is:

1. A phagemid vector for the bidirectional cloning of a DNA coding for an amino acid sequence to be fused at the N-terminus of either one or the other of two functional coat proteins, said phagemid vector comprising:
   a) DNA coding for a first functional coat protein comprising a first DNA linker at its 5' end; and
   b) DNA coding for a second functional coat protein, having the direction of transcription opposite to that of the first functional coat protein, and comprising a second DNA linker at its 5' end;
   wherein the first and second DNA linker comprise at least one identical site for a restriction enzyme not present outside said linker in the phagemid vector, and wherein the phagemid vector does not include sufficient phage genes to produce phage particles.

2. A vector of claim 1 wherein the first or second DNA linker can be transcribed in frame with the 5' end of the DNA coding for the first or second functional coat protein, and with the 3' end of the DNA coding for the amino acid sequence to be fused to and displayed by said first or second functional coat protein.

3. A vector of claim 2 wherein each of the first and second DNA linkers comprises a sequence selected from the group consisting of SEQ ID NO.: 1 and SEQ ID NO.: 2.

4. A vector of claim 2 wherein each of the first and second DNA linkers comprises a sequence selected from the group consisting of SEQ ID NO.: 4 and SEQ ID NO.: 5.

5. A vector of claim 4 comprising cp3*DDcp8* (SEQ ID NO.: 10).

6. A vector of claim 1 comprising a DNA cassette the cloning, expression, and display of at least one protein sequence to be fused at the N-terminus of either one or the other of said functional coat proteins by means of one of said DNA linker.

7. A phagemid vector of claim 6 wherein the protein sequence to be fused at the N-terminus of either one or the other of two functional coat proteins by means of a DNA linker is selected from the group consisting of an antibody, an antibody fragment, an epitope, an epitope-binding region, an antigen, an allergen, a bioactive peptide, an enzyme, an enzyme inhibitor, an enzymatic catalytic site, a DNA-binding protein, an isolated protein domain, a ligand for receptors, a receptor, a growth factor, a cytokine, and contiguous or overlapping fragments of a protein sequence of interest.

8. The vector of claim 1, wherein the DNA coding for the two functional coat proteins are modified cp3 (cp3*, SEQ ID NO.: 6) and cp8 (cp8*, SEQ ID NO.: 8).

9. The vector of claim 6 comprising a DDa cassette (SEQ ID NO.: 11) or a DDb cassette (SEQ ID NO.:12).

10. A phage or a cell library obtained using a vector of claim 1, wherein each protein sequence of said library is fused at the N-terminus of either one or the other of two functional coat proteins by means of a DNA linker.

11. A phage or a cell library of claim 10 wherein the protein sequence to be fused at the N-terminus of either one or the other of two functional coat proteins by means of a DNA linker is an antibody, an antibody fragment, an epitope, an epitope-binding region, an antigen, an allergen, a bioactive peptide, an enzyme, an enzyme inhibitor, an enzymatic catalytic site, a DNA-binding protein, an isolated protein domain, a ligand for receptors, a receptor, a growth factor, a cytokine, and contiguous or overlapping fragments of a protein sequence of interest.

12. A phage or cell library of claim 10 wherein the two functional coat proteins are modified cp3 protein (cp3* protein; SEQ ID NO.: 7) and modified cp8 protein (cp8* protein; SEQ ID NO.: 9).

13. A kit for generating a phage or a cell library wherein each protein sequence of said library is fused at the N-terminus of either one or the other of two functional coat proteins by means of a DIS linker, comprising a vector of claim 1.

14. A method for producing a phage or a cell library wherein each protein sequence of said library is fused at the N-terminus of either one or the other of two functional coat proteins by means of a DNA linker, comprising:
   a) inserting a DNA cassette in correspondence of the DNA linkers of a vector of claim 1; and
   b) transforming bacterial cells with the resulting vectors.

* * * * *